United States Patent [19]

Ichimura et al.

[11] Patent Number: 5,231,464
[45] Date of Patent: Jul. 27, 1993

[54] HIGHLY DIRECTIONAL OPTICAL SYSTEM AND OPTICAL SECTIONAL IMAGE FORMING APPARATUS EMPLOYING THE SAME

[75] Inventors: Tsutomu Ichimura, Dai 2 Green Haitsu-Zuiho 301, 1-1-20, Mukaiyama, Taihaku-ku, Sendai-shi, Miyagi 982; Fumio Inaba, 1-13-1, Yagiyama-Minami, Taihaku-ku, Sendai-shi, Miyagi 982; Masahiro Toida, Sendai, all of Japan

[73] Assignees: Research Development Corporation of Japan; Tsutomu Ichimura; Fumio Inaba, all of Japan

[21] Appl. No.: 672,973

[22] Filed: Mar. 21, 1991

[30] Foreign Application Priority Data

Mar. 26, 1990 [JP] Japan ................................. 2-77689
Mar. 26, 1990 [JP] Japan ................................. 2-77690

[51] Int. Cl.⁵ ................................. G01B 9/02
[52] U.S. Cl. ................................. 356/345; 356/39;
356/354; 356/355; 128/633; 128/634; 359/95;
382/65; 250/227.11
[58] Field of Search .......... 356/39, 40, 41, 355,
356/354, 345; 342/160; 128/633, 634; 359/95;
382/65, 53, 6; 250/227

[56] References Cited

U.S. PATENT DOCUMENTS 4,810,875 3/1989 Wyatt ................................. 128/633

*Primary Examiner*—Samuel A. Turner
*Assistant Examiner*—LaCharles Keesee
*Attorney, Agent, or Firm*—Armstrong, Westerman, Hattori, McLeland & Naughton

[57] ABSTRACT

A light propagation region is divided into a plurality of subregions, each subregion being limited within a minimum spatial resolution unit where an interference occurs between discrete points, and a 0-order diffraction pattern of a Fraunhofer diffraction image is detected If a convex lens and either a pinhole or an optical fiber which is disposed on a focal plane of the convex lens are employed and the diameter of the pinhole or the core diameter of the optical fiber is set to be not greater than the first dark ring of a Fraunhofer diffraction image produced by the convex lens, it is possible to take out the greater part of the energy of a plane wave component that enters the lens from a predetermined direction and remove other components from different directions, i.e., scattering component. If a plurality of optical systems of this type are bundled together, only a plane wave with a one- or two-dimensional intensity distribution can be taken out with high brightness and high resolving power. Since the scattering component attenuates and only an information light component carried by the plane wave can be detected, it is possible to obtain information about an absorber even when the scattering component is greater than the information light component as in the case of light transmitted by a human body. Thus, it is possible to obtain great advantages in application to optical CT or the like.

28 Claims, 63 Drawing Sheets

FIG. 9(a)
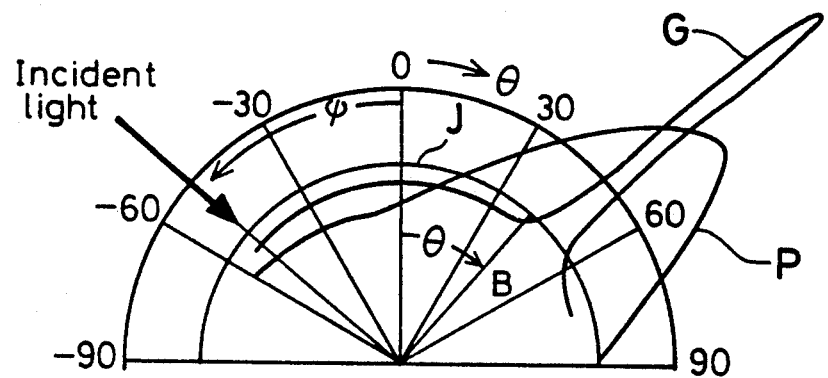
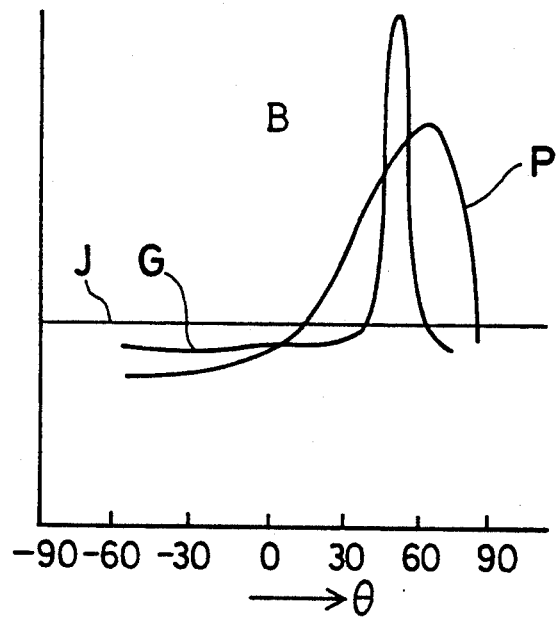
FIG. 9(b)

GL Granded-index lens

P Pinhole

Ob Objective lens    SM Single-mode fiber

N.A ≑ 0.1    N.A ≑ 0.1

GL    SM

P Pinhole

P Pinhole

PM  501  500

501  500

LU

FD

FIG. 82
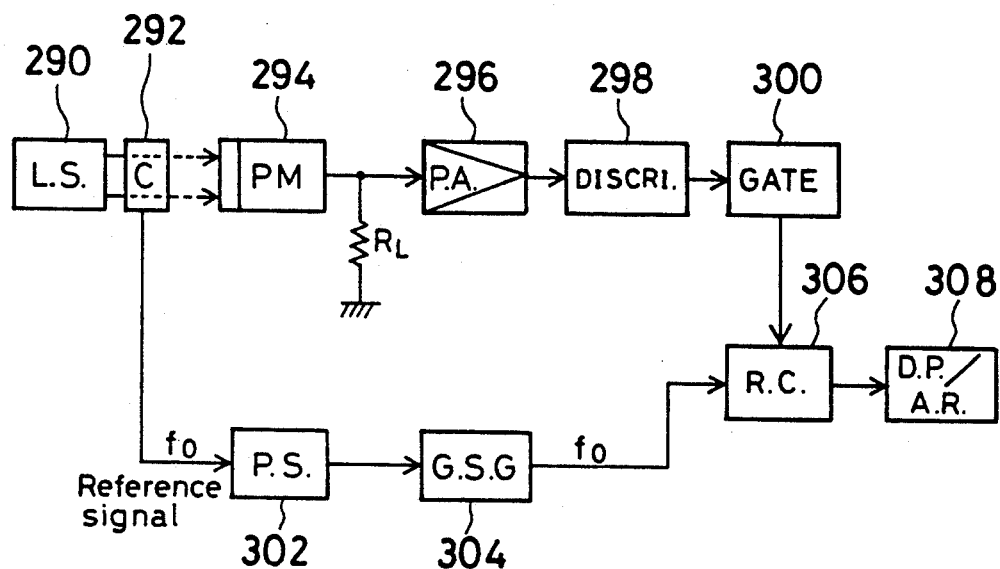
FIG.83(a)
FIG.83(b)    Add gate
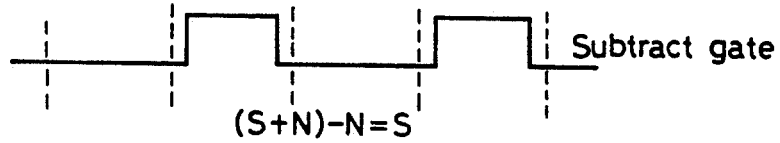
FIG.83(c)    Subtract gate
(S+N)−N=S

HIGHLY DIRECTIONAL OPTICAL SYSTEM AND OPTICAL SECTIONAL IMAGE FORMING APPARATUS EMPLOYING THE SAME

BACKGROUND OF THE INVENTION

The present invention relates to a highly directional optical system which is capable of separatively detecting a plane wave with a two-dimensional intensity distribution that enters it from a predetermined direction, and which is suitable for detecting absorption distribution in a scattering object, for example, a living body. The present invention also relates to an optical sectional image forming apparatus which is capable of imaging with high resolution information light that is wrapped obscurely in scattered light.

Since the discovery of X-rays, techniques of externally observing the inside of a living body (e.g., human body) without damaging it (i.e., a bloodless or non-destructive measuring method) have been strongly demanded and developed in the field of biology, particularly in the medical field. These techniques employ gamma rays and X rays, which have the shortest wavelengths among the electromagnetic waves, and radio waves, which have the longest wavelengths among them. The technique that employs the former has already been put to practical use as X-ray CT, and the technique that employs the latter as NMR-CT (Magnetic Resonance Imaging, i.e., MRI).

On the other hand, fewer attempts have been made to apply spectroscopy that deals with the measurement and analysis of ultraviolet, visible, near infrared and infrared spectra, which is widely employed in the fields of physics and chemistry, to in vivo measurement. This is because biometry that employs light, particularly the one that utilizes the process of absorption or emission of light has many problems left unsolved in terms of "quantitativeness", which is the most basic matter. This is the reason why reproducibility is inferior and reliability is low in regard to the absolute values obtained in measurement that is conducted at the present time by using, for example, an apparatus that measures reflected spectra with a solid-state device, or a highly sensitive TV camera.

In a case where light is applied to a scattering object such as an organic tissue, if the light is received face to face at 180°, it is possible to take out rectilinearly propagating light to some extent. However, the spatial resolving power is not very high in the present state of art.

The difference in the spatial resolving power between X-rays and light cannot be made up in the present state of art. However, employment of light rays, particularly near infrared rays will enable imaging of a tissue oxygen concentration from the hemoglobin in the blood. These light rays will give information which is different from that obtained by other techniques such as NMR-CT and X-ray CT.

For example, if an object O in FIG. 1 is a substance which does not contain a large amount of scattering matter and which has relatively high transparency, it is possible to conduct observation in such a way that a light component of a specific wavelength is selected through a filter 340 and applied to the object O from a ring-shaped slit 341 that is placed at a focal point of a lens $L_1$ and an enlarged image is formed on a plane P through an objective lens $L_2$. The use of the ring-shaped slit 341 that is placed at the focal point of the lens $L_1$ enables application of light to the object O from various directions and hence permits observation of images $I_1$, $I_2$... of the object O as viewed from various directions at a time, as shown in FIG. 2.

As for relatively thin tissues with a thickness of 3 to 5 cm, it is possible to detect light transmitted thereby. This means that "photo-roentgenography" can be used for diagnostic purposes. The women's breasts have relatively homogeneous tissues and hence readily transmit light, and it is easy to detect the light transmitted thereby (thickness: up to about 3 cm) owing to the configuration. For this reason, "photo-roentgenography" has been employed for a medical examination for breast cancer for a long time under the name of "diaphanography (lightscanning)". A conventional diagnostic apparatus for such diaphanography will be explained below with reference to FIG. 3.

FIG. 3 is a block diagram of a conventional apparatus for obtaining a light absorption distribution image. In the figure, reference numeral 401 denotes a scan head, 403 a human body, 405 a video camera, 407 an A/D converter, 409 a near infrared frame memory, 411 a red frame memory, 413 a processor, 415 a color conversion processing unit, 417 an encoder keyboard, 419 a D/A converter, 421 a printer, 423 a monitor, and 425 a video tape recorder.

Red light (strongly absorbed mainly by the hemoglobin in the blood) and near infrared light (absorbed by the blood, water, fat and so forth) are alternately applied to a part of the human body which is an object of measurement, for example, the breast, by the scan head 401 through a light guide to thereby scan the object. In the figure, light is applied upwardly from the lower side of the object. As a result, the whole breast is brightly lit up, and an image of the transmitted light is picked up by the video camera 405 and converted into a digital signal in the A/D converter 407, from which near infrared light and red light are fetched into the respective frame memories 409 and 411 through a digital switch. An intensity ratio of near infrared light to red light is computed in the processor 413 on the basis of data from the two frame memories 409 and 411. Further, color conversion and D/A conversion are executed successively, and the resulting light absorption distribution image is observed through the printer 421, the monitor 423 or the video tape recorder 425.

In this apparatus, the light rays from the scan head 410 are not parallel rays but divergent rays that diverge in the tissue (breast) as if the object were illuminated with a flashlight, and these divergent rays are received by a two-dimensional detector, i.e., a video camera; therefore, the resolving power is not very good.

One example of a system in which collimated rays are applied and received to improve the resolving power will be explained below with reference to FIG. 4.

FIG. 4 is a block diagram of a conventional apparatus that uses a collimated light applying and receiving system to obtain a light absorption distribution image.

In this example, laser light, which is used as a light source, is guided through an optical fiber 433 to illuminate an object 435 of measurement, and the transmitted light is picked up by a fiber collimator 437 and converted into an electrical signal in a detector 443, which is then sent through a pre-processing circuit 445, an A/D converter 447 and an interface 449 to a computer 451 where signal processing is executed. In this case, the optical fiber 433 for illumination and the fiber collimator 437 for detection are synchronously moved to scan the object 435 by a motor 439, thereby obtaining a light absorption distribution image of each part of the object 435 and observing it on a monitor 453.

As for the light source, a He-Ne laser of 633 nm and a semiconductor laser of 830 nm are employed for red light and near infrared light, respectively. With this diagnostic apparatus, Jobsis et al. succeeded in 1977 in detecting near infrared light transmitted by the cat's head or the human head and reported that the quantity of transmitted light varies with the respiratory condition of animals. If the size of a tissue which is to be measured is on the order of that of the cat's head, near infrared rays with wavelengths of 700 to 1500 nm enable the transmitted light to be detected satisfactorily with an illuminating light quantity of about 5 mW. This light quantity is less than 1/50 of the existing safety criterion for laser, and it is about 1/10 of near infrared rays to which we are usually exposed on the beach. The procedure is therefore considerably safe.

Incidentally, when light is applied to a living body or the like, the transmitted light is subjected to absorption and scattering by the specimen.

FIG. 5 is a graph showing Twersky's curve of scattering theory, in which the relationship between the absorbance of a red blood cell suspension and the hematocrit is determined. The graph shows the intensity of transmitted light, together with the scattering component and absorbance component of the transmitted light, obtained on illumination with laser light with a wavelength of 940 nm.

As will be understood from FIG. 5, the transmitted light involves a large scattering component superposed on the absorbance component. Since the scattering component is lacking in directivity, it includes light rays scattered from various regions, so that the resulting optical sectional image is blurred. Owing to the scattering component, the absorbance component, which is the necessary information, cannot therefore be detected with high accuracy simply by detecting the transmitted light.

FIG. 6 is a view for explanation of the optical properties of a specimen such as a living body.

In the example shown in FIG. 1, the object O contains no scattering component, that is, an object which is visual by nature is observed. In actual practice, however, a specimen 460, which is an object of observation, can be considered to be equivalent to a combination of a Rayleigh scattering object 460a which is sufficiently large in comparison to the wavelength of light, a Mie scattering object 460b which is on the wavelength order, a light transmitting information object 460c which is an object of observation and which causes the desired light absorption, a diffusing object 460d which diffuses light, a diffraction grating 460e which causes random diffraction, etc. Light that emerges from such a specimen when illuminated with a coherent plane wave through a laser optical system 461 includes Rayleigh scattered light, Mie scattered light, diffused light, random diffracted light, etc., in addition to the transmitted light, and it has heretofore been impossible to detect only the light transmitted by the information object 460c from these light rays.

FIG. 7 shows a Fresnel diffraction wave that is generated by a sinusoidal grating with a finite aperture.

When a plane wave is applied to a finite aperture, sidebands 471 and 472 are generated outside the transmitted light 470. Accordingly, it is difficult to detect the transmitted light 470 with high sensitivity for observation due to the effect of the sidebands 471 and 472.

FIG. 8 shows a luminance distribution on a plane of view that is disposed at the side of a random scattering object 480 which is remote from a light source when coherent light is applied to the object 480.

If coherent light such as laser light is applied to a scattering object such as a living body, a random diffraction image appears on the plane of view, as shown in FIG. 8(a). If the transmitted light from the scattering object 480 is focused through a lens L, as shown in FIG. 8(b), the random diffraction image makes it impossible to view an image of a region of a living body, for example, which is desired to observe with high resolving power.

FIG. 9 shows a luminance distribution of reflected rays in accordance with the condition of a plane of diffuse reflection, in which FIG. 9(a) represents it in polar coordinates, and FIG. 9(b) in rectilinear coordinates.

In the figures, reference symbol J denotes a luminance distribution of reflected rays from a plane of perfect diffusion, G a luminance distribution of reflected rays from a glossy plane, and P a luminance distribution of reflected rays from a dull plane. It will be understood from the figures that with a glossy plane a sharp peak with no expansion can be obtained in a predetermined direction, whereas with a dull plane the luminance distribution expands, and that the luminance distribution changes with the condition of the plane of reflection and hence the observation that utilizes reflected rays is greatly dependent on the condition of the plane of reflection.

As has been described above, when a sectional image is viewed by use of coherent light, the required information light is wrapped obscurely in light rays scattered by various scattering objects, so that it has heretofore been impossible to view images with high resolving power.

SUMMARY OF THE INVENTION

It is an object of the present invention to provide a highly directional optical system which is capable of reliably eliminating scattering components and detecting only the necessary information light even when the information light is wrapped obscurely in many scattering components.

It is another object of the present invention to provide a highly directional optical system which is capable of taking out substantially the whole energy of a 0-order diffraction pattern of a Fraunhofer diffraction image even when the diameter of the exit aperture is the same as the diameter of the entrance aperture.

It is still another object of the present invention to provide a highly directional optical system which comprises a multiple beam highly directional optical system and a one- or two-dimensional photodetector.

It is a further object of the present invention to provide an optical sectional image forming apparatus which is capable of detecting only information light that is wrapped obscurely in scattering components and obtaining a sectional image of high resolution.

The present invention provides a highly directional optical system comprising a light-receiving element that divides a light propagation region into a plurality of subregions so that a space region where an interference occurs between discrete points at the exit end of the light-receiving element is limited within a minimum spatial resolution unit, thereby detecting information light that is wrapped obscurely in scattered light.

Preferably, the minimum spatial resolution unit is determined by detecting a 0-order diffraction pattern of a Fraunhofer diffraction image at the exit end of the light-receiving element.

The light-receiving element may comprise a thin tube having a pinhole at each of the entrance and exit ends thereof, or a hollow thin tube having its wall surface coated with a light absorbing material, or an optical fiber in which the refractive index of the core portion is smaller than that of the cladding portion. The light-receiving element may have a long focus lens which has front and back focal points at the entrance and exit ends, respectively, or a combination of an objective lens whose front focal point is positioned at a specimen and an eyepiece whose front focal point is positioned at the back focal point of the objective lens.

In addition, the present invention provides a highly directional optical system comprising a convex lens and a pinhole which is disposed on a focal plane of the convex lens, the pinhole having a diameter which is not greater than the first dark ring of a Fraunhofer diffraction image produced by the convex lens, thereby taking out only a plane wave component that enters the convex lens from a predetermined direction.

In this case, the arrangement may be such that a second convex lens, which is substantially the same as the convex lens, is disposed at the exit side of the pinhole such that the front focal plane of the second convex lens is coincident with the plane of the pinhole, whereby a light component passing through the pinhole is taken out after being converted into a plane wave.

In addition, the present invention provides a highly directional optical system comprising a convex lens and an optical fiber which is disposed on a focal plane of the convex lens, the optical fiber having a core with a diameter which is not greater than the first dark ring of a Fraunhofer diffraction image produced by the convex lens, thereby taking out only a plane wave component that enters the convex lens from a predetermined direction.

In this case also, the arrangement may be such that a second convex lens, which is substantially the same as the convex lens, is disposed at the exit side of the optical fiber such that the front focal plane of the second convex lens is coincident with the exit end face of the optical fiber, whereby a light component passing through the optical fiber is taken out after being converted into a plane wave.

The above-described convex lens may comprise any of the following lenses: an objective lens, a graded-index lens, and a plate microlens.

In addition, the present invention provides a highly directional optical system comprising: a multiple beam highly directional optical system which comprises a bundle of highly directional optical elements each comprising a convex lens and a pinhole which is disposed on a focal plane of the convex lens, the pinhole having a diameter which is not greater than the first dark ring of a Fraunhofer diffraction image produced by the convex lens, thereby taking out only a plane wave component that enters the convex lens from a predetermined direction; and a one- or two-dimensional photodetector which is disposed at the exit side of the multiple beam highly directional optical system, thereby detecting only a plane wave with a one- or two-dimensional intensity distribution which enters from a predetermined direction.

In this case, if each of the highly directional optical elements has a second convex lens, which is substantially the same as the convex lens, the second convex lens being disposed at the exit side of the pinhole such that the front focal plane of the second convex lens is coincident with the plane of the pinhole, whereby a light component passing through the pinhole is taken out after being converted into a plane wave, then the light that emerges from the multiple beam highly directional optical system becomes a plane wave, so that, even when the one- or two-dimensional photodetector is disposed at a certain distance from the multiple beam highly directional optical system, the intensity distribution of the incident plane wave can be detected with high resolution.

In addition, the present invention provides a highly directional optical system comprising: a multiple beam highly directional optical system which comprises a bundle of highly directional optical elements each comprising a convex lens and an optical fiber which is disposed on a focal plane of the convex lens, the optical fiber having a core with a diameter which is not greater than the first dark ring of a Fraunhofer diffraction image produced by the convex lens, thereby taking out only a plane wave component that enters the convex lens from a predetermined direction; and a one- or two-dimensional photodetector which is disposed at the exit side of the multiple beam highly directional optical system, thereby detecting only a plane wave with a one- or two-dimensional intensity distribution which enters from a predetermined direction.

In this case also, if each of the highly directional optical elements has a second convex lens, which is substantially the same as the convex lens, the second convex lens being disposed at the exit side of the optical fiber such that the front focal plane of the second convex lens is coincident with the exit end face of the optical fiber, whereby a light component passing through the optical fiber is taken out after being converted into a plane wave, then the light that emerges from the multiple beam highly directional optical system becomes a plane wave, so that, even when the one- or two-dimensional photodetector is disposed at a certain distance from the multiple beam highly directional optical system, the intensity distribution of the incident plane wave can be detected with high resolution.

In addition, the present invention provides a highly directional optical system comprising a one- or two-dimensional convex lens array and a one- or two-dimensional photodetector which is disposed on a focal plane of the lens array, the photodetector being arranged to sample and separatively read out only a zero-order diffraction pattern of a Fraunhofer diffraction image produced by each convex lens, thereby detecting only a plane wave with a one- or two-dimensional intensity distribution which enters from a predetermined direction.

The above-described convex lens may comprise any of the following lenses: an objective lens, a graded-index lens, and a plate microlens.

In addition, the present invention provides an optical sectional image forming apparatus comprising: a laser light source for illuminating an object of measurement with laser light directly or through a lens system; a high resolution light-receiving system comprising a plurality of light-receiving elements each receiving the transmitted light from the object illuminated with the laser light and dividing a light propagation region into a plurality of subregions so that a space region where an interference occurs between discrete points at the exit end is limited within a minimum spatial resolution unit; photoelectric detecting means for detecting emergent light rays from the high resolution light-receiving system and converting them into electrical signals; and means for arithmetically processing the detected signals from the photoelectric detecting means, thereby determining a light absorption distribution of the object, and thus obtaining an optical sectional image.

The arrangement may be such that the transmitted light from the object of measurement is received through a chopper, and the detected signal by the photoelectric detecting means is subjected to synchronous detection to remove the background component. The arrangement may also be such that an object of measurement is alternately illuminated with laser light of different wavelengths, and the transmitted light from the object is received through a sector and subjected to synchronous detection, and then a light absorption distribution is obtained from a signal corresponding to each wavelength. The arrangement may also be such that a sector capable of obtaining optical signals of two wavelengths and a dark signal is employed to determine the sum of and difference between the detected signal for each wavelength and the dark signal, thereby removing the background component.

BRIEF DESCRIPTION OF THE DRAWINGS

FIGS. 9(a-b) show reflection patterns at diffusing planes;

FIGS. 82 and 83(a–c) are views for explanation of an extremely feeble light measuring method;

DESCRIPTION OF THE PREFERRED EMBODIMENTS

First of all, the basic principles of the present invention will be explained.

Figure 1:
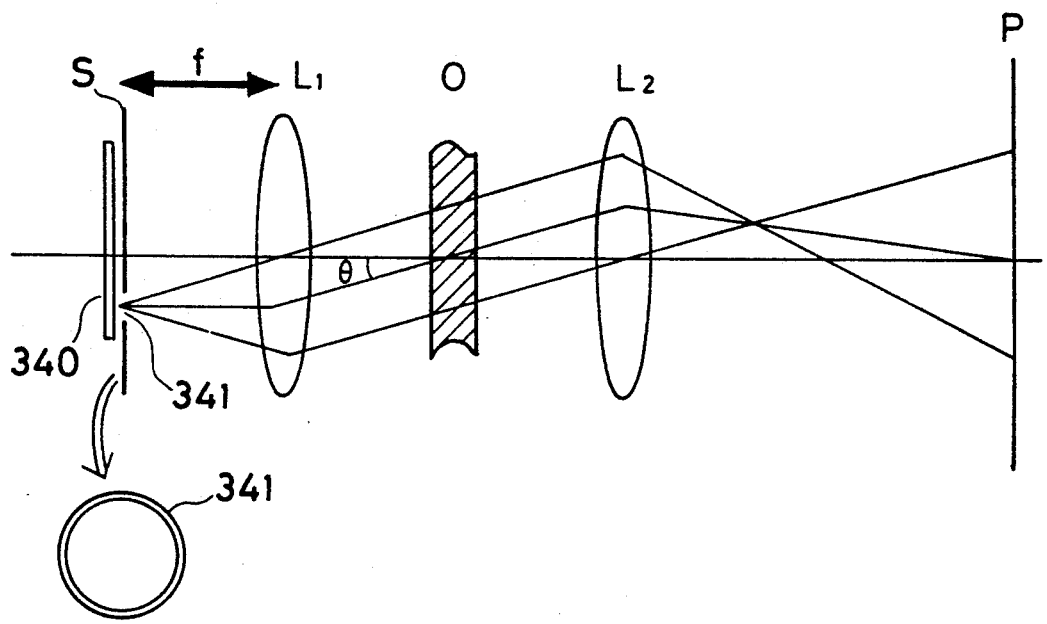
FIGS. 1 and 2 are views for explanation of a conventional optical CT image observation method.
Figure 2:
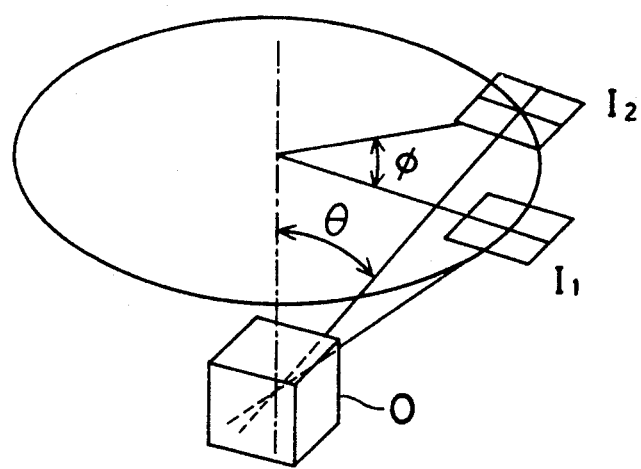
Figure 3:
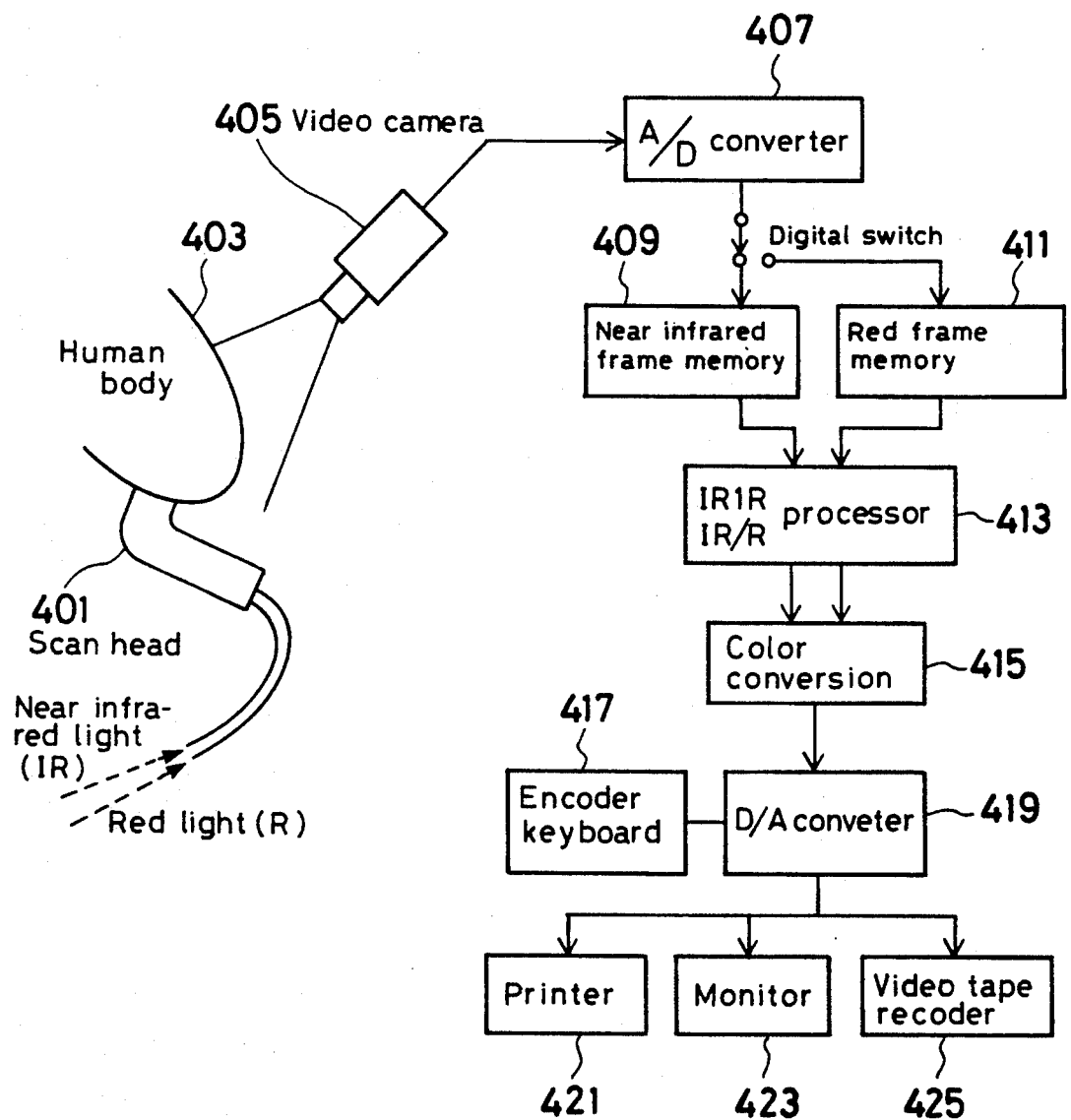
FIG. 3 shows the arrangement of a conventional apparatus for obtaining a light absorption distribution image.
Figure 4:
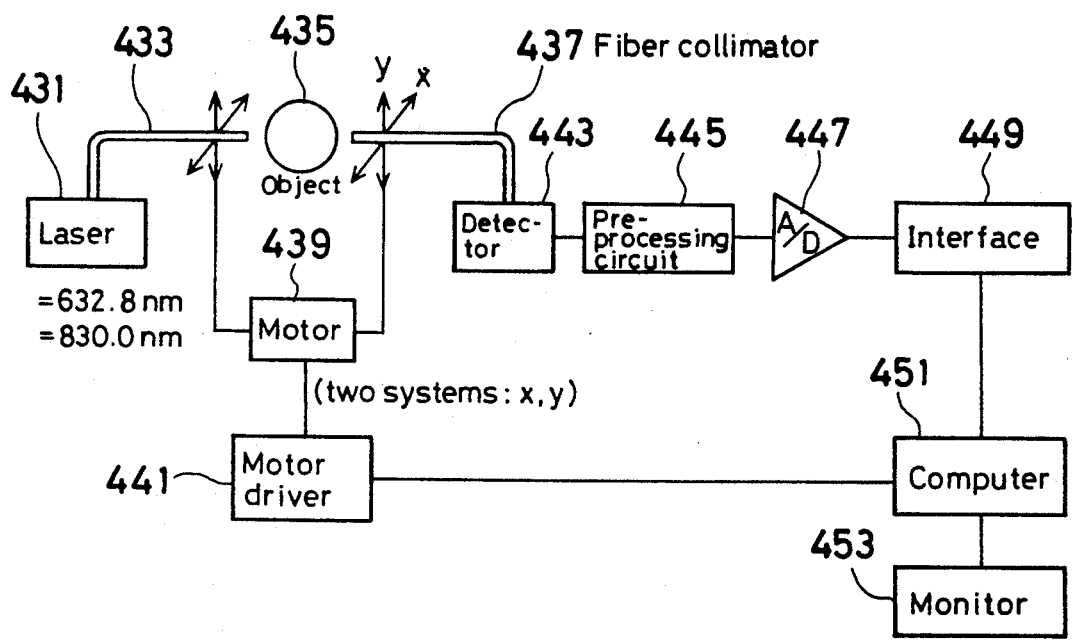
FIG. 4 shows the arrangement of another conventional apparatus for obtaining a light absorption distribution image.
Figure 5:
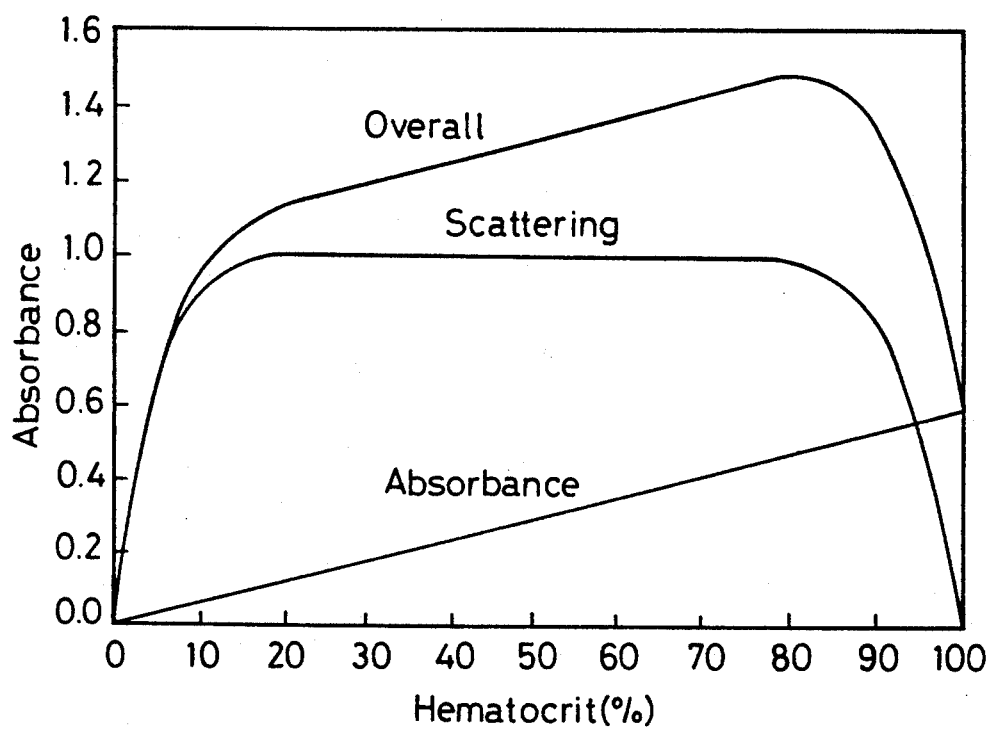
FIG. 5 is a graph showing Twersky's curve of scattering theory.
Figure 6:
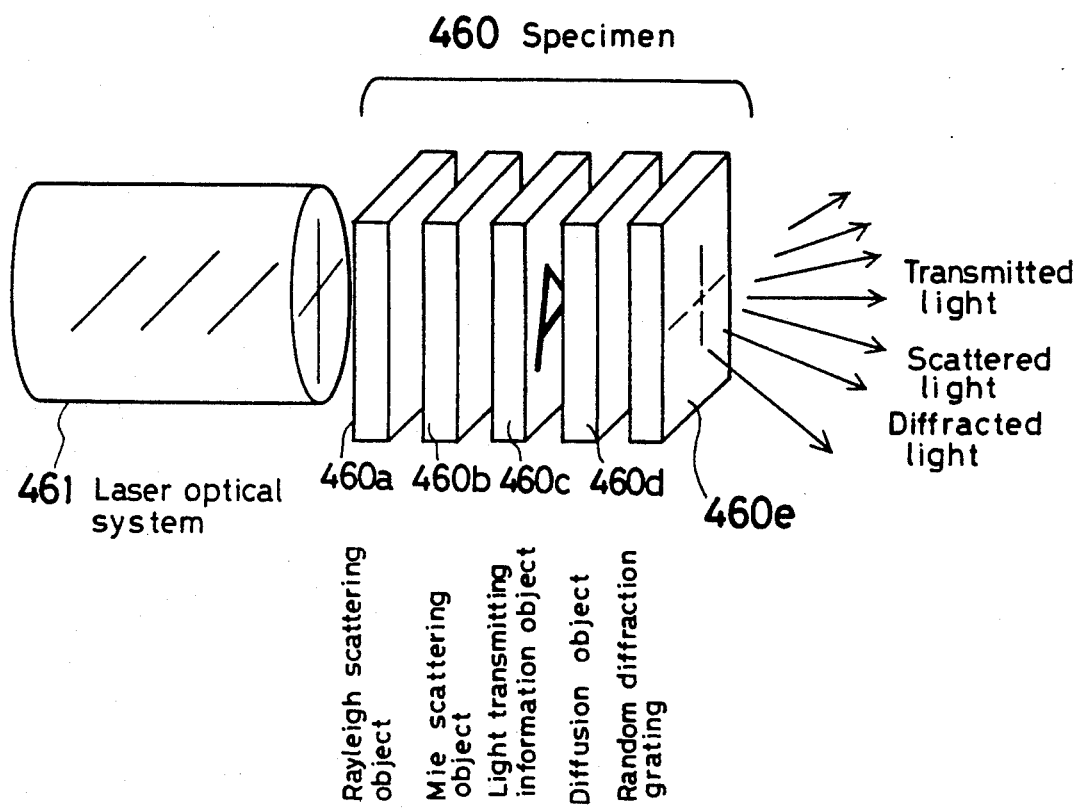
FIG. 6 is a view for explanation of the optical properties of a specimen.
Figure 7:
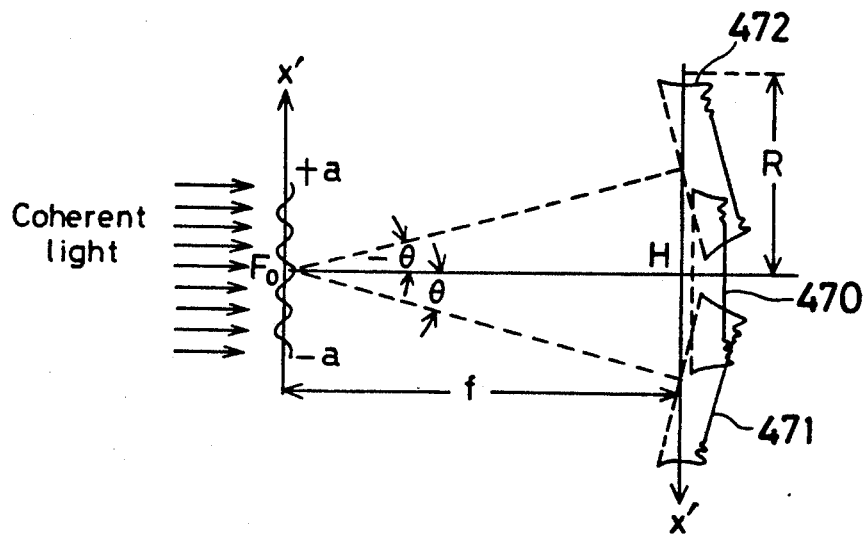
FIG. 7 is a view for explanation of a diffraction pattern produced by a finite aperture.
Figure 8A:
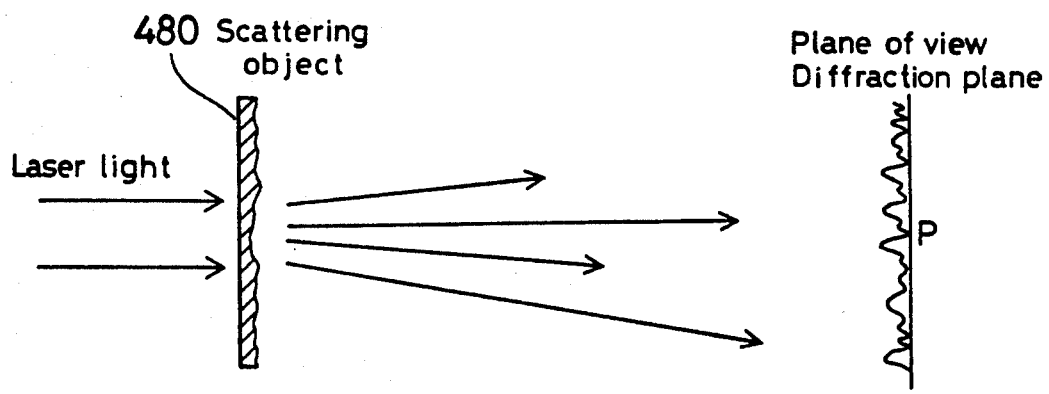
FIGS. 8(a-b) are views for explanation of a random diffraction pattern produced by a scattering object.
Figure 8B:
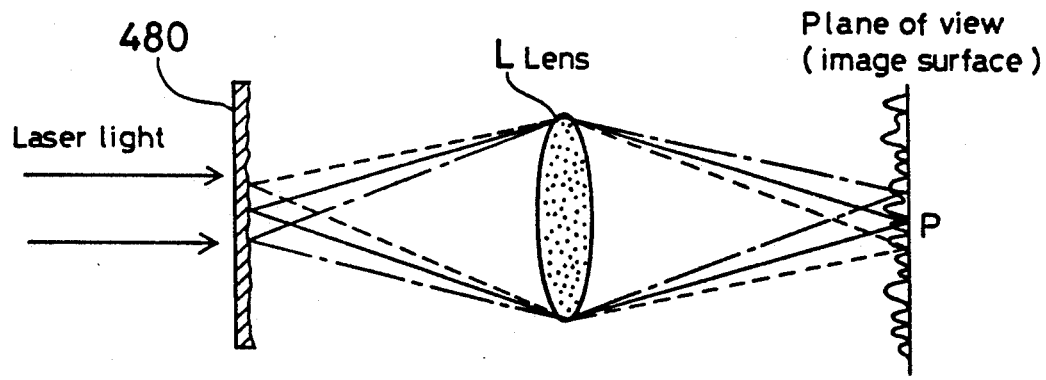
Figure 10:
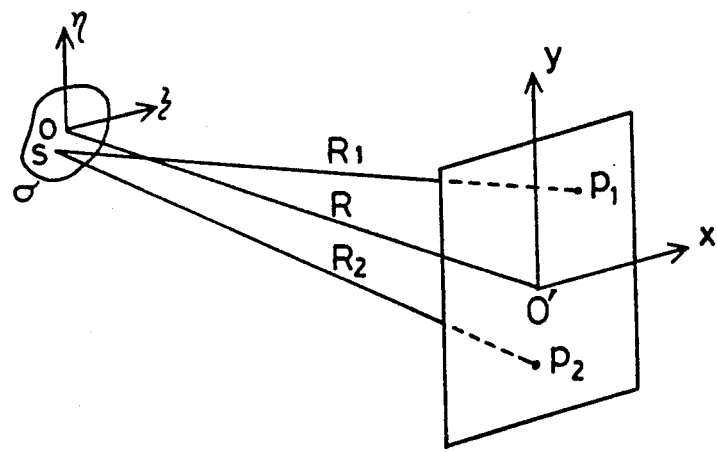
FIGS. 10 and 11(a-b) are views for explanation of the principle of image formation.

Referring to FIG. 10, the degree of coherence (complex degree of coherence) that describes the correlation between vibrations at a pair of fixed and movable points $P_2$ and $P_1$ on a plane illuminated by a quasi-monochromatic light source $\sigma$ with a finite size is equal to a normalized complex amplitude at the corresponding point $P_1$ in a diffraction pattern that is centered at $P_2$, the diffraction pattern being formed when the light source is replaced with a diffraction aperture which has the same size and the same configuration as those of the light source and the aperture is filled with a spherical wave which converges on $P_2$ and whose amplitude on the wavefront is proportional to the intensity of the light source. This is known as van Cittert-Zernike theorem. On the basis of this theorem, an imagery equation is induced.

Figure 11A:
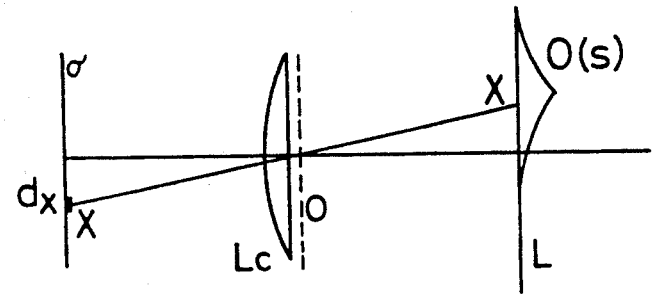
Figure 11B:
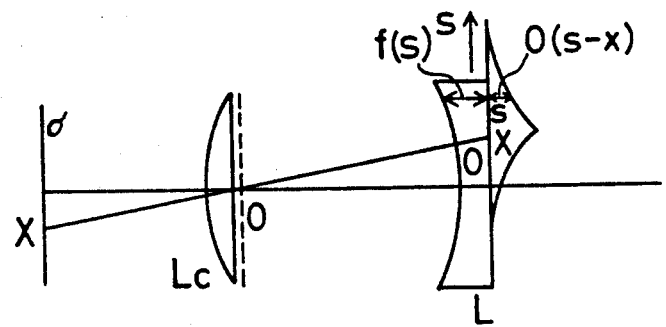

For simplification, the following matter will be treated two-dimensionally. Assuming that a minute light source $d_x$ is present at the point X on $\sigma$, as shown in FIG. 11(a), and the light from $d_x$ is coherent, the light passes through a lens $L_c$ and an object O to form a spectrum O(s) on L which is centered at X (0 frequency). Since $\sigma$ and L are represented in the same coordinates X and the origin of O(s) is at X, a component that can pass through L is a part of it. Next, assuming that the pupil function is f and the absorption and wavefront aberration of the lens are a(s) and W(s), respectively, as shown in FIG. 11(b), the following expression is given:

$$f(s) = a(s)e^{-i(2\pi/\lambda)W(s)} \quad (|s| \leq 1) \quad (1)$$

In Eq. (1), the origin of f(s) is at the intersection O of the pupil and the optical axis. Accordingly, a spectrum that can pass through f(s) is O(s−X)f(s). If the intensity at the point X is 1, the spectrum passing through the pupil is subjected to Fourier inverse transformation through the lens L, that is, the complex amplitude of the image on the image plane is given by $$o'(u') = \int O(s-k)f(s)e^{2\pi i u's}ds \quad (2)$$

Accordingly, the intensity that is produced on the image plane by $d_x$ is given by $$i(u')dX = |\int O(s-X)f(s)e^{2\pi i u's}ds|^2 \quad (3)$$

Eq. (3) may also be interpreted as follows. That is, the complex amplitude $o'(u')$ of the image on the image plane is given by $$o'(u') = \int_{-\infty}^{+\infty} O(s' - X)f(s')e^{2\pi i u's'}ds' \quad (4)$$

In Eq. (4), the variable s is changed to s'. Although the pupil function is finite, it is 0 in the other cases; therefore, the upper and lower limits of the integral are determined to be $+\infty$ and $-\infty$. If $s'-X=f'$ in Eq. (4), $ds'=df'$; therefore, $o'(u')$ is given by $$o'(u') = \int_{-\infty}^{+\infty} O(f')f(f' + X)e^{2\pi i u'(f'+X)}df' \quad (5)$$
$$= e^{2\pi i u'X} \int_{-\infty}^{+\infty} O(f') \times f(f' + X)e^{2\pi i u'f'}df'$$

If the variable is rewritten to s'' and $s''-X=f''$ in the same way as the above and the complex conjugate of $o'(u')$ is represented by $o'^*(u')$, it is given by $$o'^*(u') = e^{-2\pi i u'X} \int_{-\infty}^{+\infty} O^*(f'') \times f^*(f'' + X)e^{-2\pi i u'f''}df'' \quad (6)$$

$$i(u')dX = o'(u')o'^*(u')dX \quad (7)$$

If this is integrated over the whole effective light source $\sigma(X)$:

$$I(u') = \int_{-\infty}^{+\infty} \sigma(X)i(u')dX \qquad (8)$$

If Eqs. (5) and (6) are substituted into Eq. (7) and this is substituted into Eq. (8):

$$\begin{aligned}I(u') &= \int \sigma(X)dX \int \int O(f')O^*(f'') \times \\ &\quad f(f'+X)f^*(f''+X)e^{2\pi i u'(f'-f'')}df'df'' \\ &= \int \int \int \sigma(X)f(f'+X)f^*(f''+X) \times \\ &\quad O(f')O^*(f'')e^{2\pi i u'(f'-f'')}df'df''dX\end{aligned} \qquad (9)$$

Here, if the integral containing X is separated:

$$\int \sigma(X)f(f'+X)f^*(f''+X)dX = T(f',f'') \qquad (10)$$

T is called cross modulation coefficient. If this is substituted into Eq. (9), the following imagery equation is obtained:

$$\begin{aligned}I(u') &= \int \int_{-\infty}^{+\infty} T(f',f'')O(f')O^*(f'') \times e^{2\pi i u'(f'-f'')}df'df'' \\ &= \int \int_{-\infty}^{+\infty} \sigma(X)f(f'+X)f^*(f''+X)O(f') \times \\ &\quad O^*(f'')e^{2\pi i u'(f'-f'')}df'df''dX\end{aligned} \qquad (11)$$

Eq. (11) means that, when the object spectrum is represented by O(s), the image I(u') is equal to the integration over all frequencies of the product of interference fringes produced by beating of spectra O(f') and O*(f'') and the weight T(f',f''). T(f',f'') is not a function of f'−f'' only. Even if f'−f'' is the same, f' and f'' differ depending upon the position. That is, even if the beat frequency f'−f''=f is the same, T(f',f'') depends on f' and f'' and hence the imagery equation is a non-linear mapping system in which the same T(f',f'') cannot be employed; therefore, it is, in general, difficult to make an imagery analysis.

Figure 12:
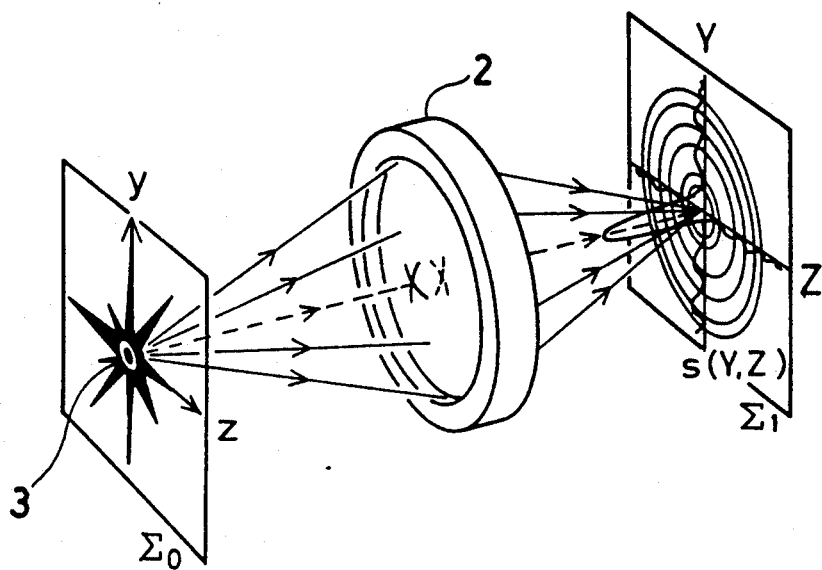
FIG. 12 is a view for explanation of image formation by coherent light.
Figure 13:
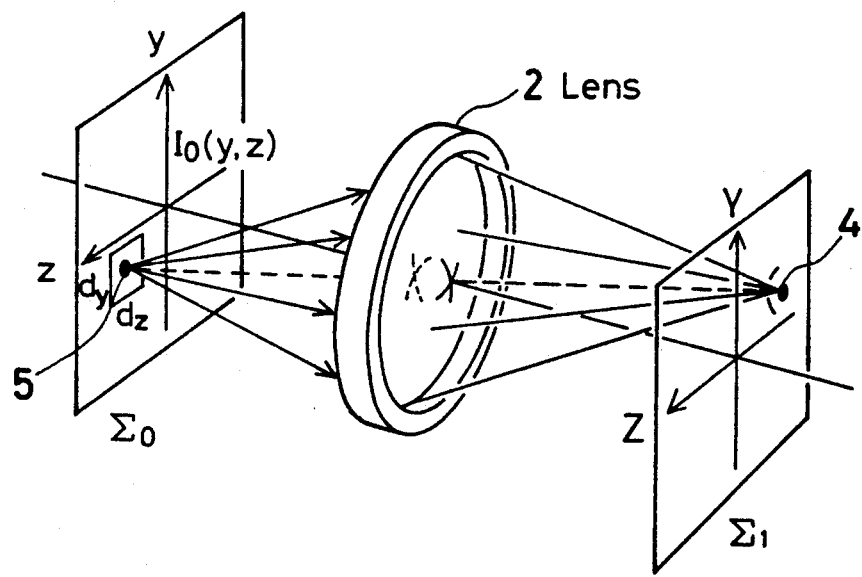
FIG. 13 is a view for explanation of image formation by incoherent light.

For example, assuming that light is transmitted through a minute hole 3 in an object plane $\Sigma_o$, as shown in FIG. 12, the light is applied through a lens system 2 to an imagery plane $\Sigma_i$ where it presents a light intensity distribution with a skirt spread in a ring-like shape about a certain point, so that light rays from various points on the object interfer with each other on the imagery plane. Thus, no image analysis can be made unless all the influences of the interference are integrated.

The imagery equation can be solved in the following cases.

(a) When $\sigma(X)$ is infinite in a coherent system:

T(f',f'') is a function of f=f'−f'' only and the system is therefore linear. T(f) in this case is called response function. In incoherent image formation, an image of a minute region 5 on the object plane $\Sigma_o$ is formed at a point 4 on the imagery plane $\Sigma_i$ through the lens system 2. At this time, the light intensity forms a sharp peak at the point 4 on the imagery plane $\Sigma_i$ without showing a spread intensity distribution. Accordingly, images of various points on the object are independently formed on the imagery plane without interfering with each other.

(b) When $\sigma(X)$ is a point source in a coherent system:

In this case, T(f',f'')=const. The imagery equation (11) can therefore be solved. T(f) in this case is called response function.

(c) In the case of a approximate linear system:

In a case where the system is partially coherent and the greater part of the object is transparent and the object contains scattered pale images or minute object points, the greater part of illuminating light passes straight through the object. Accordingly, only the zero-order spectrum is large, whereas other higher-order spectra are very small, so that the beat frequency (f=f'−f'') component can be ignored. Since an image is formed mainly of the beat components of only the spectrum of f''=0 and the spectrum of f', f'=f is valid. Thus, the mapping characteristics of the system can be approximately described only by f.

Figure 14A:
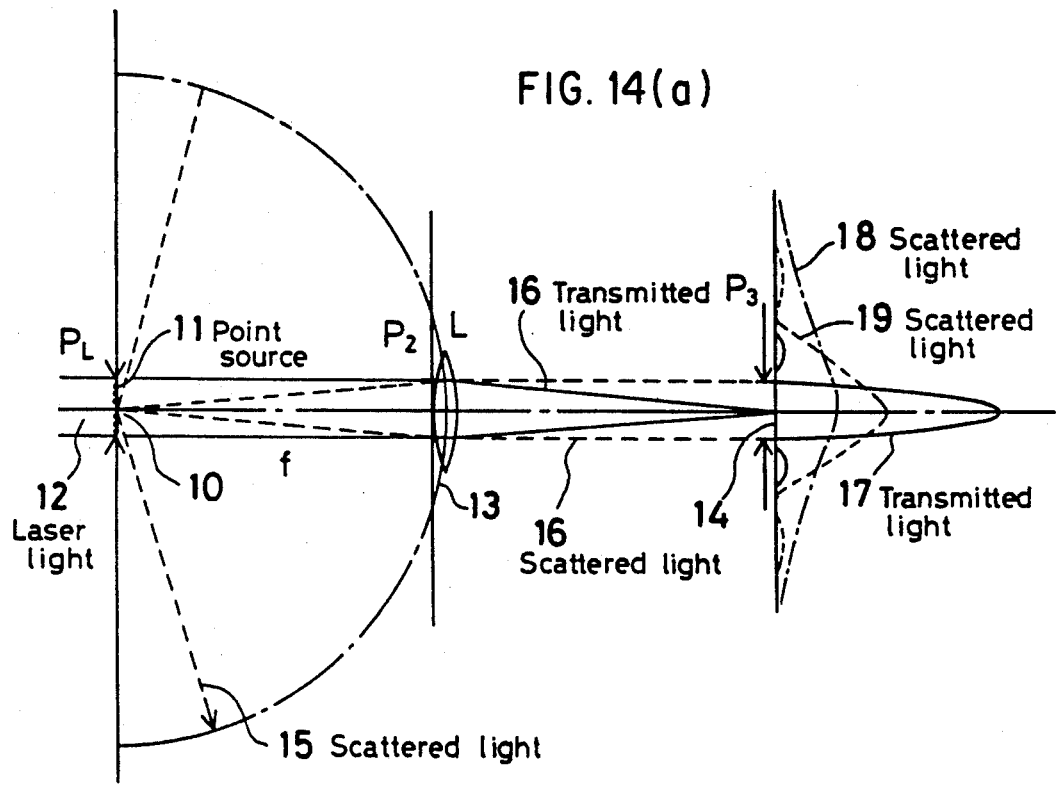
FIGS. 14(a-b) is a view for explanation of Fraunhofer diffractions of plane and spherical waves.
Figure 14B:
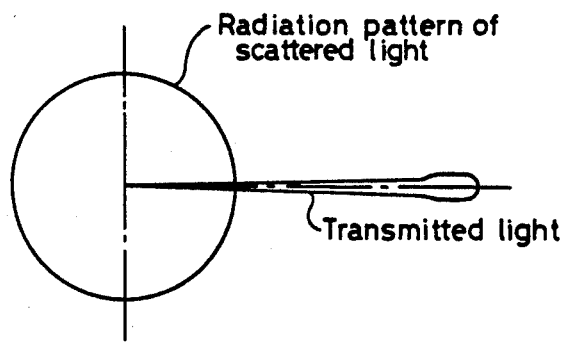

Incidentally, when laser light is passed through an aperture 10, as shown in FIG. 14(a), it is possible to consider that innumerable point sources 11 are present in the aperture 10. Hence, the light spreads in the form of a plane wave, which travel in the same direction as that of the incident light, and a spherical wave. More specifically, the radiation pattern of the scattered light is spherical, whereas the radiation pattern of the transmitted light that propagates in the form of a plane wave has an acute directivity, as shown in FIG. 14(b). On a plane $P_3$ which is at a sufficiently long distance, a Fraunhofer diffraction image is observed, and the plane wave shows an intensity distribution in which the 0-order spectrum is extremely large, while higher-order spectra are small, as shown in the form of transmitted light 17. On the other hand, scattered light 18 resulting from the spherical wave shows a flat intensity distribution, as illustrated. However, when a lens 13 is disposed halfway, the scattered light 19 also form a diffraction pattern in which the 0-order spectrum is relatively large. At the position where the Fraunhofer diffraction image is available, the scattered light has sufficiently attenuated, so that the 0-order spectrum of the plane wave is satisfactorily large, as will be understood from FIG. 14(a).

Figure 15:
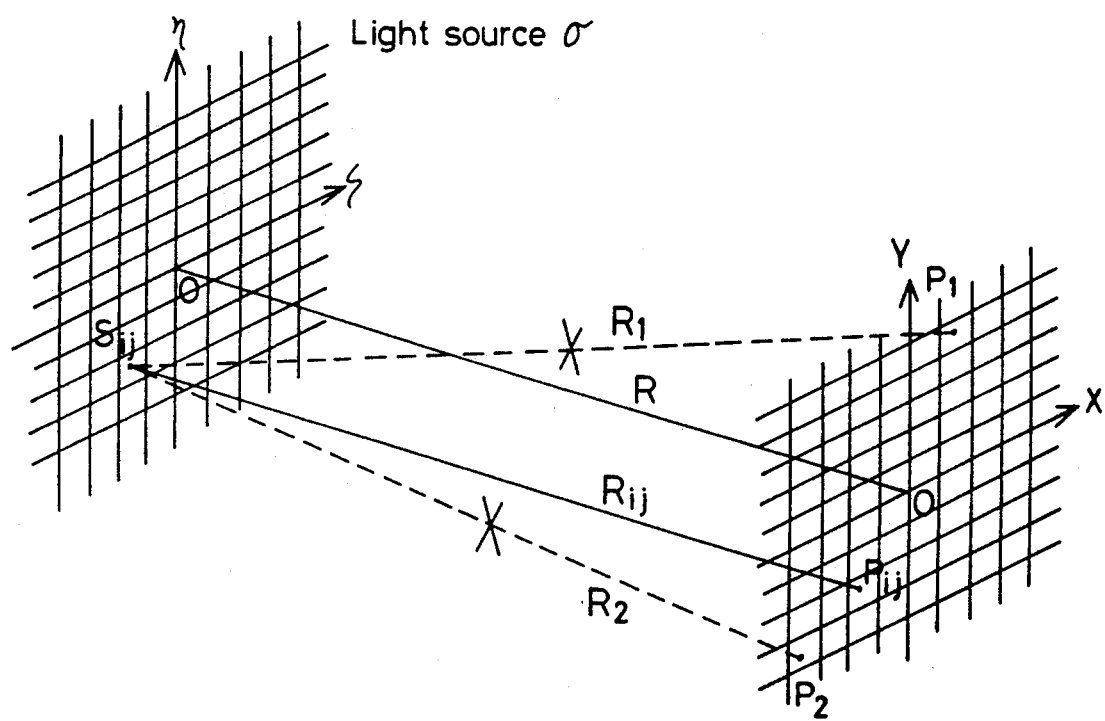
FIG. 15 is a view for explanation of the image formation me according to the present invention.

The present invention was made by noting this point. That is, if the 0-order spectrum of the Fraunhofer diffraction image alone is observed, since the intensity of the spectrum is high, information about the object of observation can be obtained satisfactorily and almost all the scattering component can be eliminated. In addition, since there is no possibility of the higher-order spectra of the plane wave producing an effect on other positions, the above-mentioned response function can be linearized to simplify the imagery analysis. More specifically, on a plane P which is at a distance R away from a light source $\sigma$ and where a Fraunhofer diffraction image can be observed, as shown in FIG. 15, the light intensity on the plane O by a minute light source $S_{ij}$ is detected only at a position $P_{ij}$ which corresponds to the minute light source $S_{ij}$ in the direction of the optical axis, but it is not detected at other positions $P_1$, $P_2$, etc.

FIG. 16 is a view for explanation of the principle of the highly directional optical system according to the present invention, in which reference numeral 1 denotes a slit, and 1a a pinhole. The solid-line waveform represents a field intensity, and the chain-line waveform a light intensity.

Figure 16A:
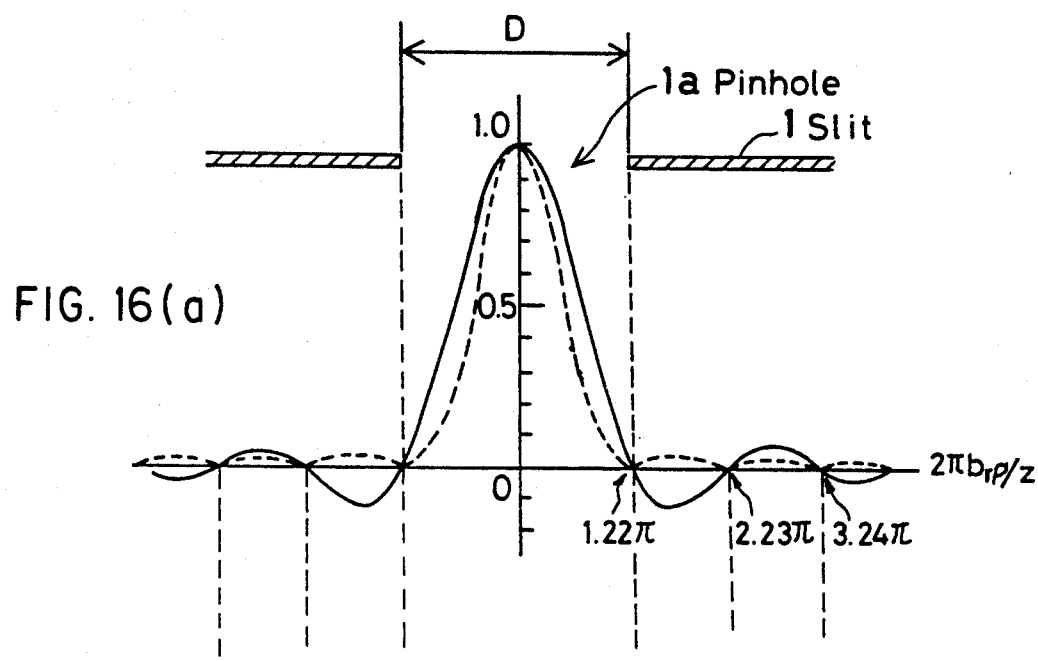
FIGS. 16(a-b) is a view for explanation of the detection principle of an optical system according to the present invention.
Figure 16B:
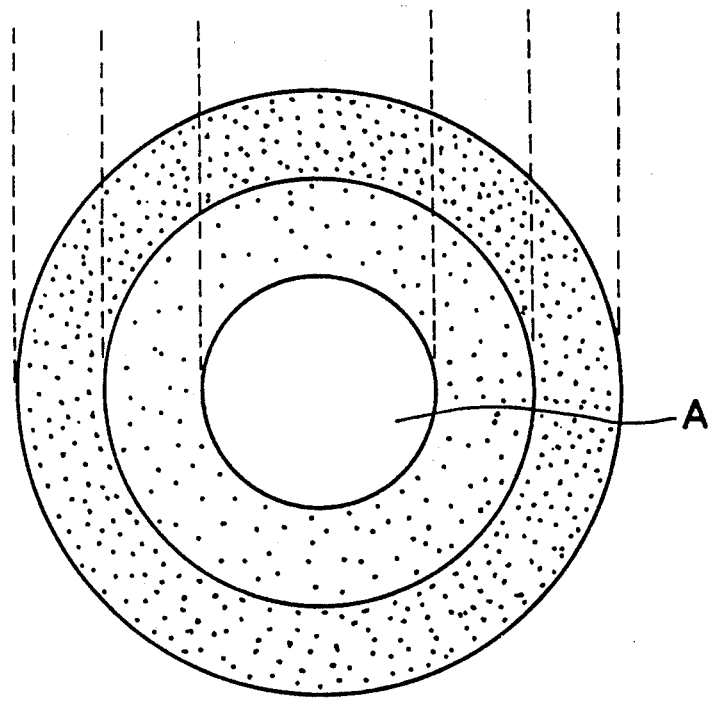

In the case of a pinhole with a circular aperture, a Fraunhofer diffraction image such as that shown in FIG. 16(a) can be observed at a position which is at a sufficiently long distance therefrom. The diffraction image, known as Airy's disk, comprises a plurality of dark rings and a bright region between each pair of adjacent dark rings, as shown in FIG. 16(b). The region A inside the first dark ring, that is, the portion of the 0-order spectrum, is the brightest region. Therefore, if the slit 1 having a pinhole with a diameter which is equal to the width of the 0-order spectrum, that is, the diameter of the first dark ring, is disposed to conduct image observation, it is possible to detect the 0-order spectrum only and eliminate the other higher-order spectra. If this detection is effected for each point, no interference between different positions occurs. That is, it is possible to prevent the influence of the van Cittert-Zernike theorem from extending to the image formation. Accordingly, when minute information light is contained in the scattered light as in the case of optical CT, only the information light can be separatively detected from the scattered light. Although the van Cittert-Zernike theorem is valid within the pinhole, as a matter of course, in the optical system according to the present invention the region where this theorem is valid is limited within the smallest unit of spatial resolution.

In the case of a plane wave, the condition in which a Fraunhofer diffraction image is formed may be expressed as follows:

$$z >> r^2_{max}/2\lambda \tag{12}$$

where r is the aperture diameter of the light source and z is the propagation distance.

Accordingly, it is only necessary to set a distance which satisfies Eq. (12) to form a Fraunhofer diffraction image and then detect only the 0-order spectrum therefrom.

The diffraction image of a pinhole with a circular aperture may be expressed as follows:

$$I(\rho) = \left(\frac{\pi Dr^2}{\lambda z}\right)^2 \left[\frac{2J_1(2\pi Dr\rho/\lambda z)}{2\pi Dr\rho/\lambda z}\right]^2$$

where Dr is the diameter of the pinhole, $J_1$ is Bessel function, $\lambda$ is the wavelength, and z is the length on the optical axis.

The radius $\Delta\rho$ of the first dark ring of Airy's disk may be expressed as follows:

$$\Delta\rho = 0.61 \times \lambda z/Dr$$

Thus, the region within the first dark ring contains 84% of the entire light quantity. It is therefore possible to detect the plane wave at a loss of 16% by taking in light within the first dark ring formed by the pinhole. On the other hand, the spherical wave attenuates in inverse proportion to the square of the distance. Therefore, it is possible to perform image observation with high resolution by taking in only the 0-order spectrum of the Fraunhofer diffraction image.

Figure 17:
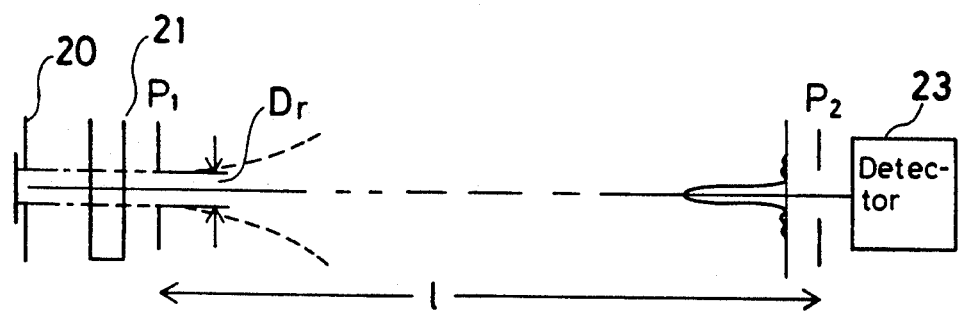
FIG. 17 shows an optical system for detecting a 0-order spectrum with two pinholes.

FIG. 17 shows one embodiment of the highly directional optical system according to the present invention which is designed to detect a 0-order Fraunhofer diffraction pattern with two pinholes.

Laser light from a light source 20 is applied to a specimen 21, and the transmitted light is passed through a slit $P_1$ and further through a slit $P_2$ which is spaced apart from the slit $P_1$ by a distance l which satisfies Eq. (12) to detect a 0-order beam of light with a detector 23.

Assuming that the pinhole diameters of the slits $P_1$ and $P_2$ are Dr and D, respectively, the wavelength of the laser light is $\lambda$ and the radius $\Delta\rho$ of the first dark ring, the following relationship holds:

$$D = 2\Delta\rho = 1.22 \times \lambda l/Dr \tag{13}$$

If $\lambda = 500$ nm, $l = 6$ m and $Dr = 1$ mm, then $D = 7.32$ mm.

Figure 18:
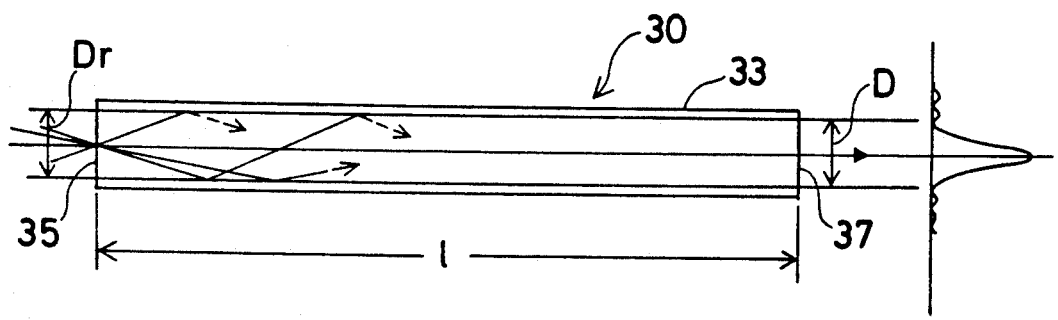
FIG. 18 shows a highly directional optical system the inner surface of which is coated with an absorber.

FIG. 18 shows another embodiment of the present invention that utilizes a highly directional optical system (this term being used in the same sense as high-resolution light-receiving system).

In the figure, reference numeral 30 denotes a highly directional optical element, 33 a light absorbing material, 35 a core, and 37 a cladding.

Referring to FIG. 18, the highly directional optical element 30 comprises, for example, a hollow, straight, long and thin glass fiber the inner wall surface of which is coated with a light absorbing material, e.g., carbon.

Assuming that light enters the optical element 30 from an entrance end face 35, rays which are parallel to the optical axis of the optical element 30 travel in straight lines and emerge from an exit end face 37, but rays which are at angles to the optical axis impinge upon the wall surface and are absorbed by the absorbing material 33 without emerging from the exit end face 37. Assuming that the aperture diameter and length of the highly directional optical element 33 are D and l, respectively, and the wavelength of the incident light is $\lambda$, the length l with which light components which are not parallel to the optical axis are absorbed and a Fraunhofer diffraction image is formed at the exit end face 38 completely by the plane wave is expressed by the following relationship:

$$l \propto Dr^2/\lambda$$

In other words, the length l is a distance at which a Fraunhofer diffraction can be observed.

For example, in the case of $\lambda = 6328$ Å: when Dr = 10 mm, l = 600 m; when Dr = 1 mm, l = 6 m; when Dr = 0.1 mm, l = 6 cm; when Dr = 0.01 mm, l = 0.6 mm; when Dr = 1 $\mu$m, l = 6 $\mu$m; and when Dr = 0.5 $\mu$m, l = 1.25 $\mu$m.

Accordingly, if the aperture diameter and length of the highly directional optical element are properly set in accordance with the object of measurement and the optical element is sufficiently long in comparison to the entrance aperture diameter, among light rays entering the highly directional optical element only the plane wave that is parallel to the optical axis can be taken out from the exit end face. However, the diameter of the optical element needs to be sufficiently large in comparison to the wavelength of the incident light to propagate the plane wave. If the diameter is on the order of the wavelength of the incident light, the effect of diffraction is large, so that the light quantity that can be taken out from the exit end face is extremely small. When only a 0-order Fraunhofer diffraction pattern is to be detected, the degree of separation of incoherent scattered light from a plane wave as a signal light is given by $$\frac{\text{scattering intensity}}{\text{transmitted plane wave intensity}} \approx \left(\frac{\lambda}{Dr}\right)^2$$

In other words, the larger the entrance aperture diameter Dr of the highly directional optical element in comparison to the wavelength $\lambda$, the more the scattered light attenuates, and the more the scattered light can be separated from the plane wave.

Figure 19:
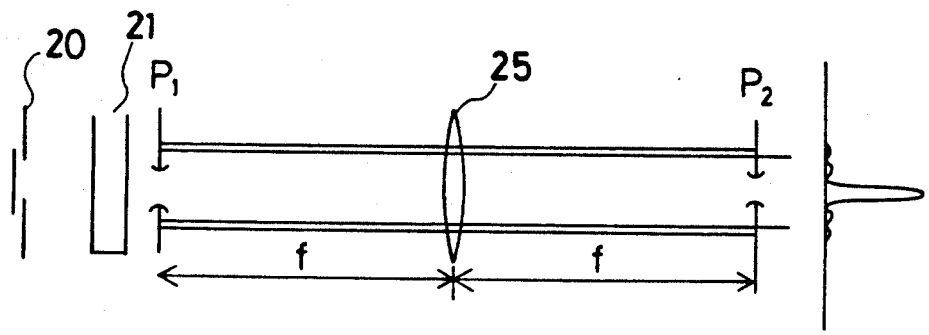
FIGS. 19 and 20 show one embodiment of the present invention in which a 0-order spectrum is detected with a long focus lens.
Figure 20:
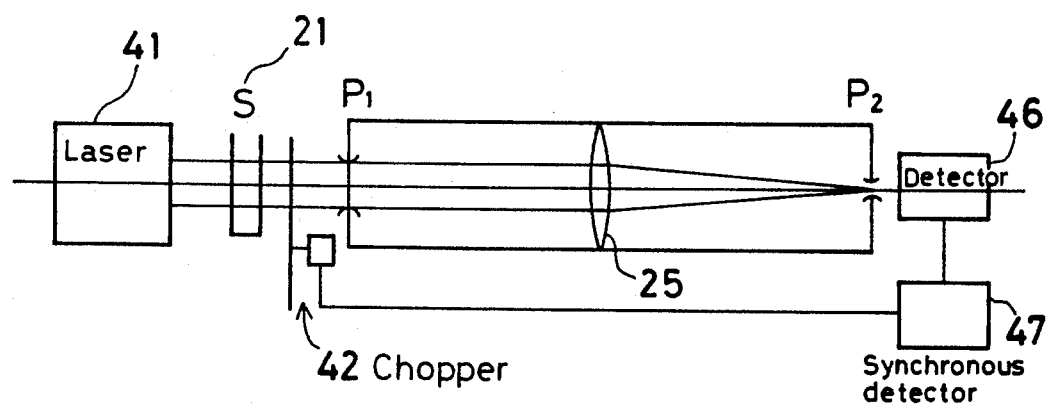

FIGS. 19 and 20 show other embodiments of the present invention which employ a long focus lens (telescope).

Referring to FIG. 19, a long focus lens 25 is used to form on the back focal plane a Fraunhofer diffraction image produced by an aperture on a front focal plane, thereby enabling a reduction in the distance. In the case where such a lens is employed also, the aperture diameter D can be obtained in the same way as in the case of Eq. (13). In the case of $\lambda = 500$ nm, when the focal length $f = 1$ m and $Dr = 1$ mm, $D = 1.22$ mm; and when the focal length $f = 5$ m and $Dr = 5$ mm, $D = 1.22$ mm.

In the embodiment shown in FIG. 20, a specimen 21 is illuminated with a laser light source 41. The transmitted light is interrupted by a chopper 42 and detected by a detector 46 synchronously with the switching period of the chopper 42 to thereby remove slow drifts such as power source variations, temperature variations, etc.

The following is a description of a detector which is suitable for an optical system for use in a microscopic optical CT.

Figure 21:
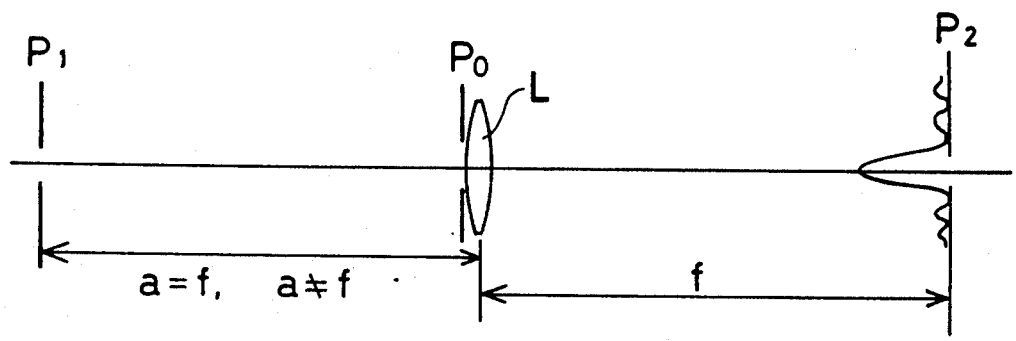
FIG. 21 is a view for explanation of the basic principle of a highly directional optical element that employs a lens.

As shown in FIG. 21, this embodiment is arranged such that a diffraction wave that is produced by an entrance aperture $P_1$ is made incident on a convex lens L and a pinhole $P_2$ with a diameter which is approximately equal to the first dark ring of the diffraction image is disposed on a focal plane of the lens L to thereby take out the greater part of the 0-order diffraction pattern. More particularly, the diameter of the pinhole $P_2$ is set to be not greater than the entrance aperture $P_1$. In this case, the entrance aperture $P_1$ may be the aperture $P_0$ of the lens L itself. First, the relationship between the size of the 0-order diffraction pattern and the aperture $P_1$ is determined. The diameter D of the first dark ring of Airy's disk produced when a diffraction image is formed by the lens is given by:

$$D = 2.44 \lambda \cdot f / D_r \quad (14)$$

where $D_r$ is the diameter of the aperture $P_1$ and f is the focal length of the lens L. The condition in which the aperture diameter $D_r$ exceeds the first dark ring diameter D are given by:

$$D_r^2 \geq 2.44 \lambda \cdot f \quad (15)$$

It is extremely easy to form a highly directional optical element that satisfies the above condition by use of a convex lens. Let us give numerical examples. When light with a wavelength $\lambda$ of 500 nm is employed, if a convex lens with a focal length f of 5 cm is employed for an aperture diameter Dr of 1 mm, the diameter D of the first dark ring of Airy's disk is $6.1 \times 10^{-2}$ mm, and if a convex lens with a focal length f of 10 cm is employed, the diameter D of the first dark ring is $1.22 \times 10^{-1}$ mm. Thus, it will be understood that these convex lenses satisfy the condition of Eq. (15). If a highly directional optical element that satisfies the condition of Eq. (15) is employed as a unit, even when a large number of highly directional optical elements are densely arranged adjacent to each other to take in all incident plane waves, there is no fear of adjacent elements interferring with each other, so that it is possible to detect with high resolving power, for example, an absorption image that is carried by a two-dimensional plane wave which varies in intensity with the position.

Figure 22:
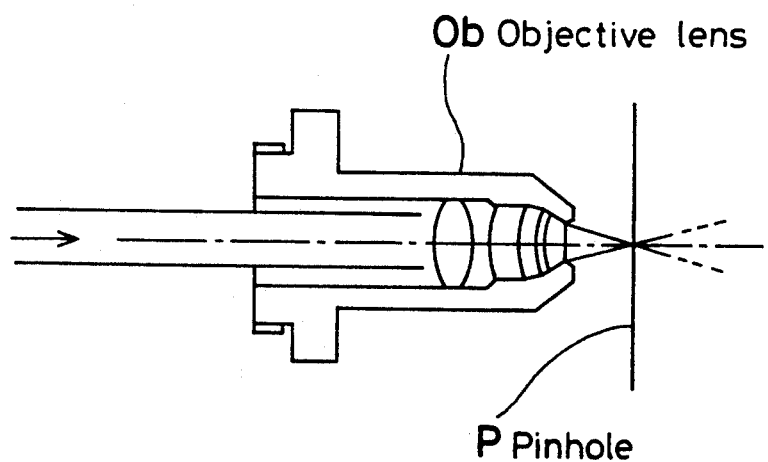
FIGS. 22 and 23(a-b) illustrate one embodiment of a highly directional optical element; 5
Figure 23A:
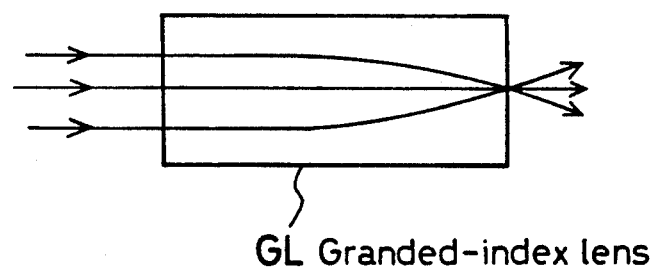
Figure 23B:
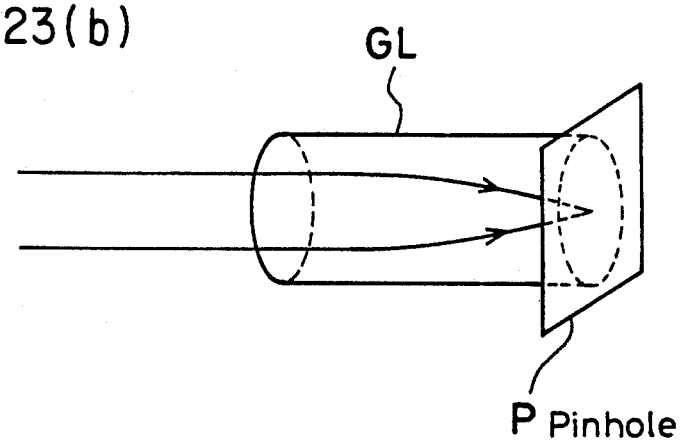

One specific example of highly directional optical elements will next be explained. FIG. 22 shows a highly directional optical element which comprises an objective lens Ob, e.g., a microscope objective lens, which satisfies the relationship of Eq. (15), and a pinhole P that is disposed on a focal plane of the lens Ob, the pinhole P being adapted to pass only a 0-order Fraunhofer diffraction pattern formed by the objective lens Ob. FIG. 23(a) shows another form of convex lens GL, which is known as SELFOC lens (trade name) and which is also called graded-index lens. The lens GL, in which the refractive index gradually lowers from the central axis toward the periphery, performs a condensing function in the same way as in the case of a convex lens. By properly selecting the length of the lens GL, the focal plane can be made coincident with an end face of a circular cylinder. A pinhole P which is similar to that shown in FIG. 22 is disposed on the focal plane at one end of the graded-index lens GL, as shown in FIG. 23(b), thereby making it possible to pass only a 0-order diffraction pattern produced by Fraunhofer diffraction.

Figure 24:
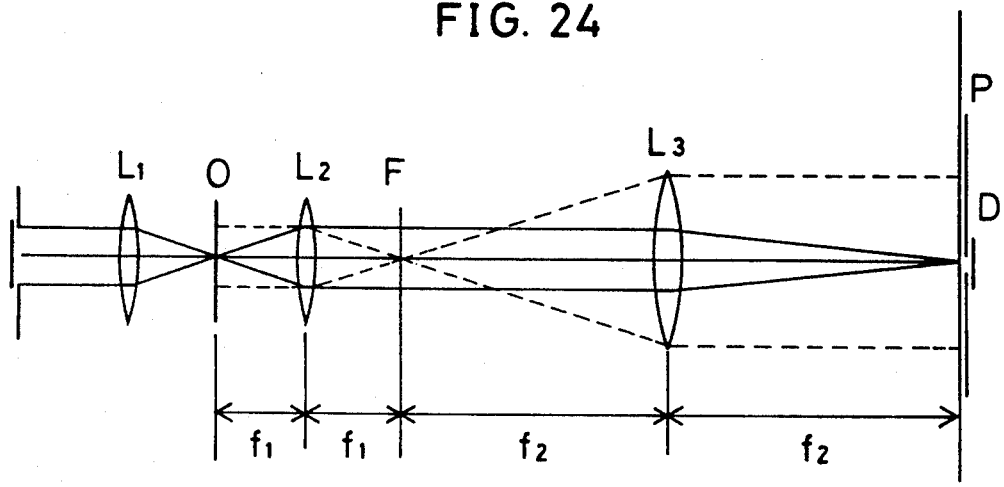
FIGS. 24 and 25 show one embodiment of an optical system for microscopic optical CT.
Figure 25:
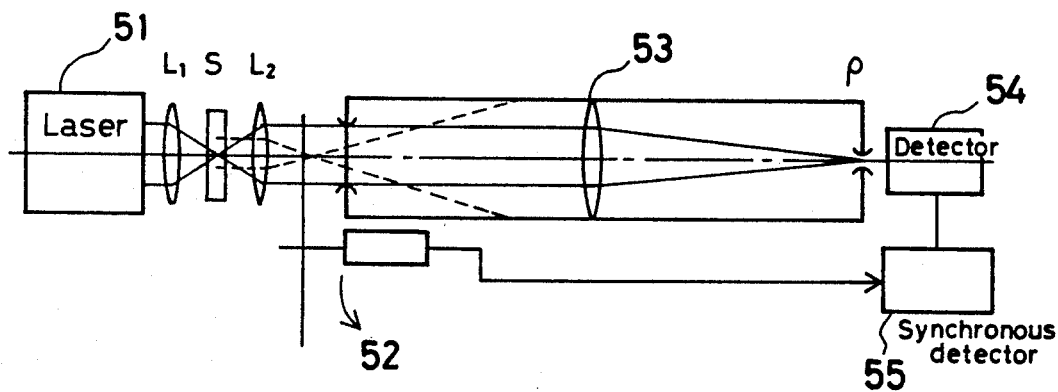

FIGS. 24 and 25 respectively show embodiments of optical systems for microscopic optical CT.

Referring to FIG. 24, laser light is applied to a specimen O after being narrowed down through a condenser lens $L_1$. The specimen O is set in the vicinity of the front focal point of an objective lens $L_2$ so that an enlarged image thereof can be observed. The image of the specimen O is enlarged through an eyepiece $L_3$ whose front focal point is at the position of the back focal point of the objective lens $L_2$, and the enlarged image is detected through a pinhole in a plane P. Each focal length $f_1$ of the objective lens $L_2$ and each focal length $f_2$ of the eyepiece $L_3$ are set to be $f_2 >> f_1$ so that a Fraunhofer diffraction image can be observed. In this embodiment, the entire image of the specimen can be observed by scanning the specimen surface with laser light. It should be noted that the chain line in the figure represents the optical path of scattered light, which diffuses and attenuates in the form of a spherical wave.

In the embodiment shown in FIG. 25, laser light is applied to a specimen O after being narrowed down through a condenser lens $L_1$, and an enlarged image of the specimen O is formed through an objective lens $L_2$. Then, while the scattering component is attenuated through a long focus lens (telescope) 53, a 0-order diffraction pattern is observed. It should be noted that light that is to be taken in is interrupted by a chopper 52 and detected synchronously with the chopper action, thereby removing slow drifts such as power source variations, temperature variations, etc., and thus enabling an improvement in the resolution.

Figure 23:
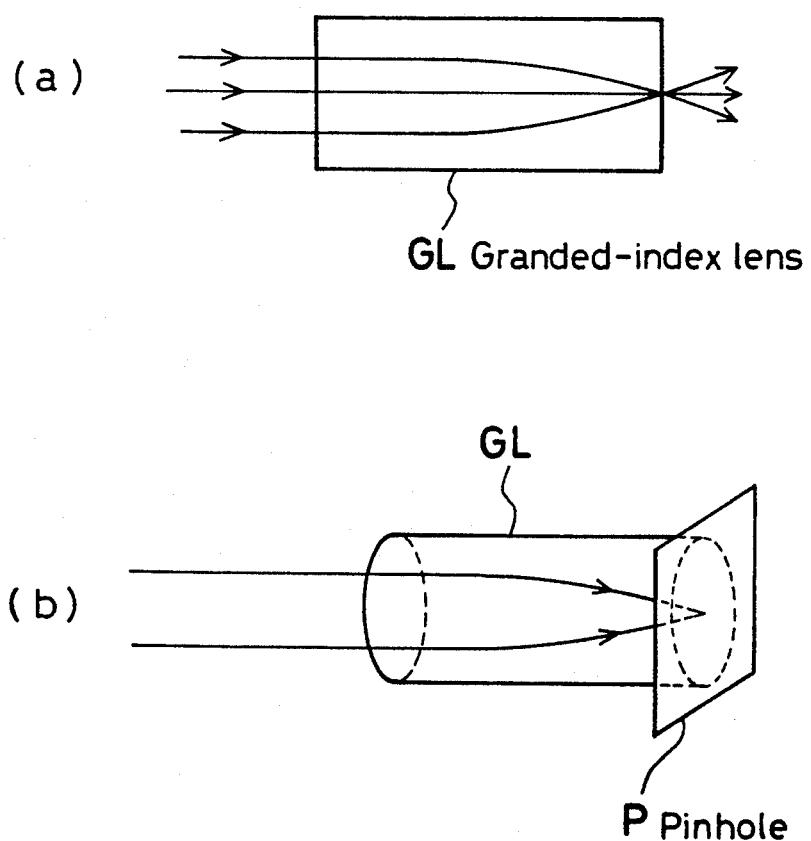

Among known optical fibers are multimode fiber, graded-index fiber, single-mode fiber, etc. Among them, the single-mode fiber has an extremely small core diameter and passes only light that enters the core end face at the entrance end, but does not light which is at a large angle to the axis. Such a single-mode fiber can be employed in place of the pinhole P in FIGS. 22 to 23(b). Moreover, since the aperture of the single-mode fiber is coincident with the first dark ring of a Fraunhofer diffraction image produced by the objective lens Ob or the graded-index lens GL, the single-mode fiber is conveniently employed to transmit efficiently only a 0-order diffraction pattern produced by Fraunhofer diffraction. In addition, since such an optical fiber is employed as an exit part, the light detected can be led to any desired place, which is advantageous from the viewpoint of arrangement.

Figure 26:
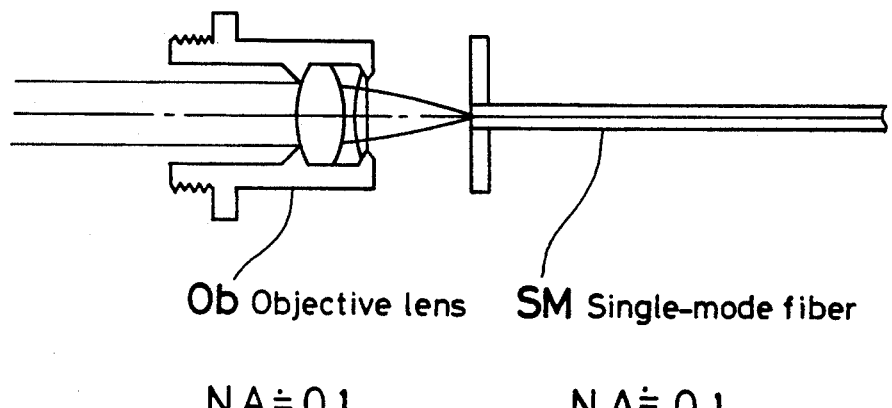
FIG. 26 to 31 illustrate embodiments of the highly directional optical element according to the present invention.
Figure 27:
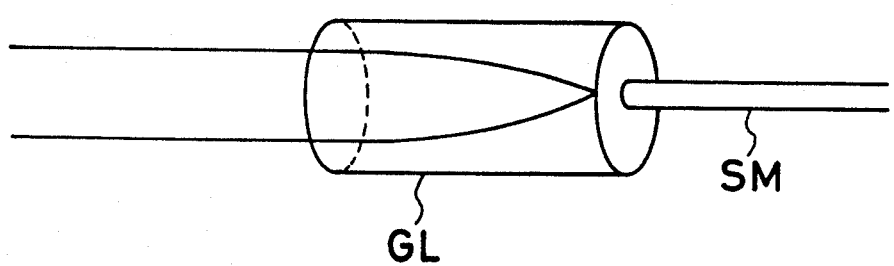
Figure 28:
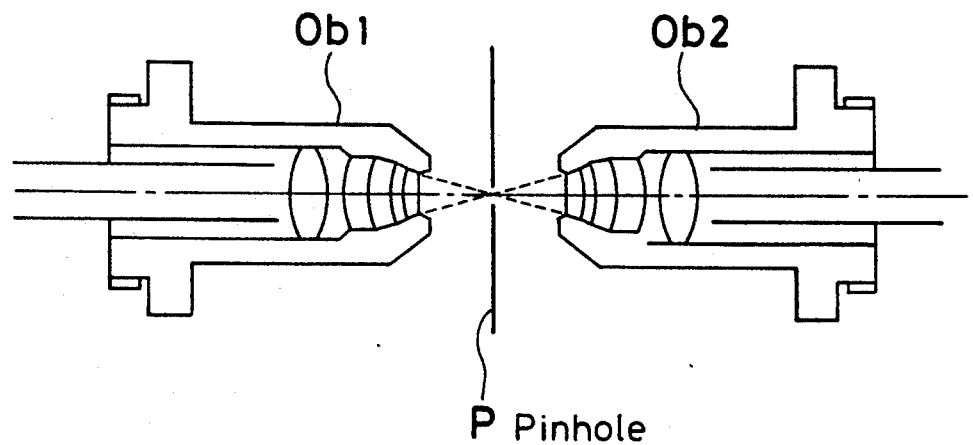

FIG. 26 shows an embodiment of the highly directional optical element which comprises an objective lens Ob and a single-mode fiber SM that is disposed at a focal point of the lens Ob. FIG. 27 shows an embodiment of the highly directional optical element which comprises a graded-index lens GL and a single-mode fiber SM that is disposed at the focal point of the lens GL at one end thereof. In the case of an eyepiece or the like, it is possible to make the first dark ring of a Fraunhofer diffraction image equal to the aperture of a multimode fiber. For example, by inserting a small aperture in front of the lens, the first dark ring can be made coincident with the aperture of a multimode fiber. In such a case, a multimode fiber can also be used.

The plane wave that has passed through the above-described highly directional optical element emerges from the element in the form of a divergent spherical wave. In a case where a photodetector is disposed in the back of the pinhole P to measure absorbance, for example, the emergent light may be divergent. However, in a case where a large number of highly directional optical elements are bundled together to detect a distribution image of an absorbent object, it is preferable to arrange the optical elements so that the light emerges therefrom in the form of a plane wave.

FIGS. 28 to 31 show some embodiments of such arrangement. In the embodiment shown in FIG. 28, an objective lens Ob2 which is similar to an objective lens Ob1 at the entrance side is disposed at the exit side such that the focal point of the lens Ob2 is coincident with a pinhole P that is disposed halfway between the two lenses, so that a 0-order diffraction pattern passes through the pinhole P to become a spherical wave, which is converted back to a plane wave through the objective lens Ob2. In the embodiment shown in FIG. 29, a graded-index lens GL1 is disposed in front of a pinhole P in the same way as in FIG. 23(b) and a graded-index lens GL2 which is similar to the lens GL1 is disposed in a confocal manner. In the embodiment shown in FIG. 30(a), a single-mode fiber SM is employed in place of the pinhole P shown in FIG. 28. It should be noted that either one of the pair of objective lenses Ob1 and Ob2 may be replaced with a graded-index lens GL, as shown in FIG. 30(b). In this case, it is necessary that the first dark ring of a Fraunhofer diffraction image produced by the graded-index lens GL be approximately coincident with the first dark ring by the objective lens Ob1 or Ob2. In the embodiment shown in FIG. 31, a single-mode fiber SM is employed in place of the pinhole P shown in FIG. 29.

Any of the highly directional optical elements described above cannot simultaneously detect all the regions of a plane wave having a two-dimensional distribution. Therefore, a large number of highly directional optical elements are arranged two-dimentionally to form a multiple beam highly directional optical system.

Figure 32:
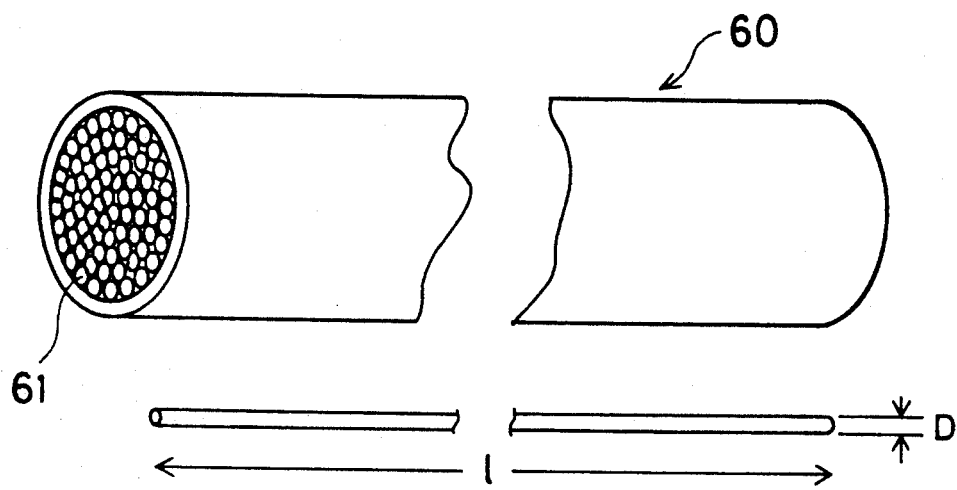
FIG. 32 shows on embodiment of a highly directional optical system which comprises a bundle of optical systems according to the present invention.

FIG. 32 shows an embodiment of a high-resolution optical system which comprises a plurality of optical systems of the present invention which are bundled together to enable an overall image of a specimen to be observed at a time.

An optical device 60 comprises highly directional optical elements 61 such as those described above. The distance l is set at a length which fulfills Eq. (12), and D is a diameter which enables a 0-order diffraction pattern to be taken out. The use of such optical elements enables observation of a clear object image since the exit ends of the optical elements are independent of each other and hence no interference occurs between the positions corresponding to the adjacent elements.

Figure 33:
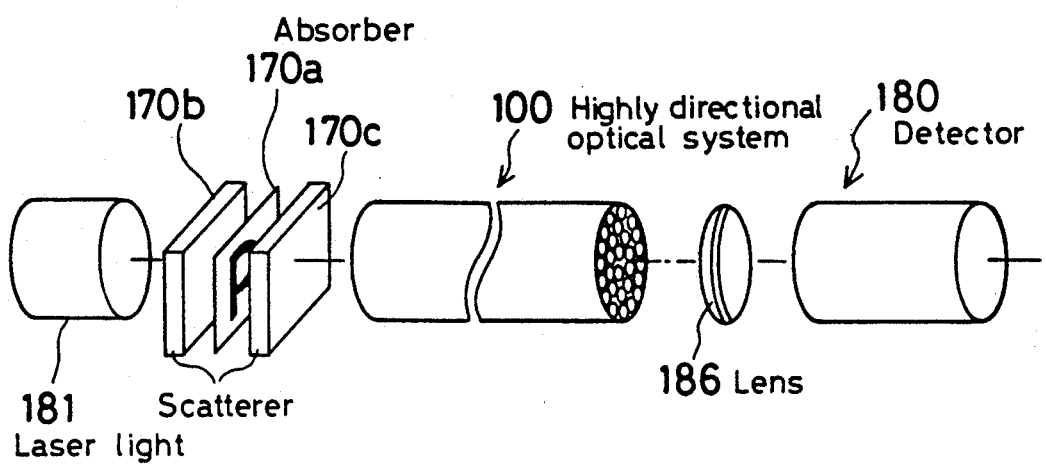
FIG. 33 is a conceptual view showing a detection system of the present invention.

FIG. 33 shows the concept of the detection method according to the present invention. In the figure, reference numeral 100 denotes a highly directional optical system, 181 a laser light source, 170 an absorber, 170b and 170c scatterers, and 186 a lens.

As is illustrated, an object of measurement, e.g., a living body, comprises the scatterers 170b, 170c and the absorber 170a which coexist with each other. By illuminating the object with laser light and detecting the transmitted light with the optical system of the present invention, the scattering component generated by the scatterers 170b and 170c is eliminated, so that only the absorption component generated by the absorber 170a can be detected.

Figure 34A:
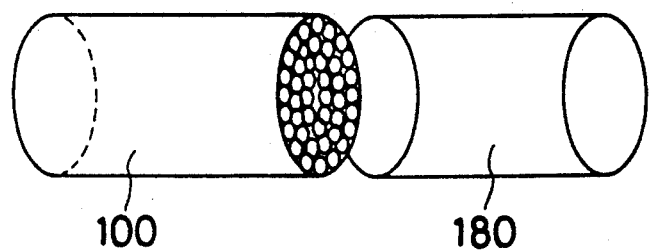
FIGS. 34(a-b) and 35(a-c) are views for explanation of detection methods by the highly directional optical system according to the present invention.
Figure 34B:
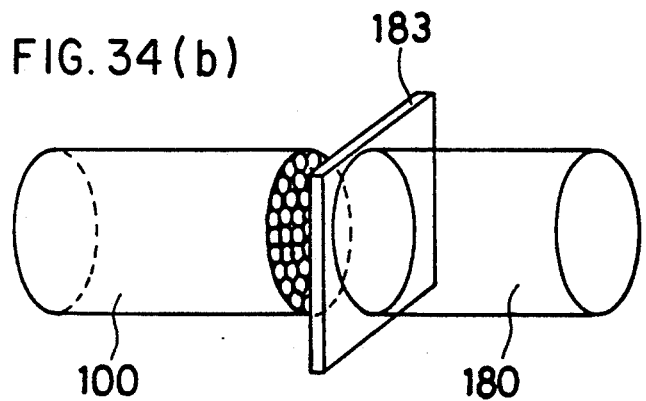

The detection by the optical system of the present invention may be effected directly by a detector 180, as shown in FIG. 34(a). Alternatively, opal glass 183 may be inserted in between the optical system 100 and the detector 180 to smooth an image observed in the form of a group of discontinuous rays of light into a clear image, as shown in FIG. 34(b).

Figure 35A:
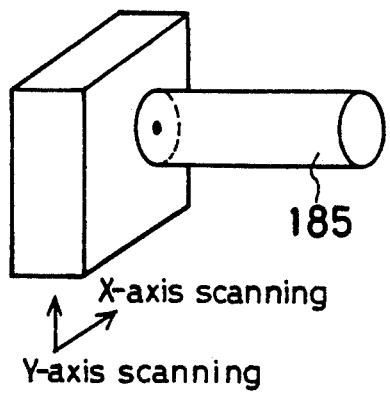
Figure 35B:
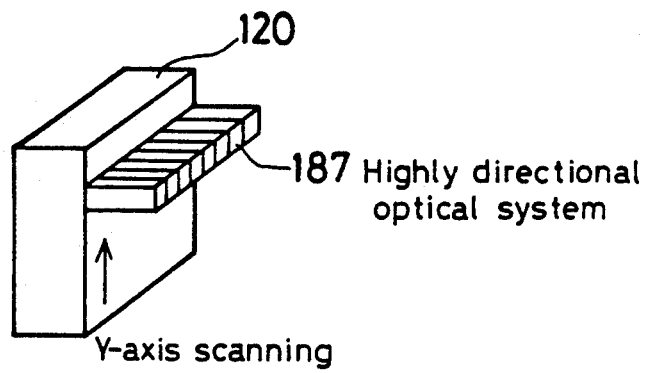
Figure 35C:
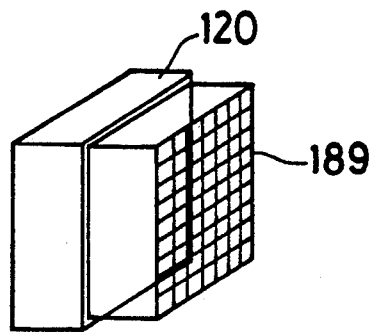

The detection of output light from the optical system may be effected by scanning the optical system with a point detector 185 in the X- and Y-axis directions, as shown in FIG. 35(a). Alternatively, as shown in FIG. 35(b), the output light may be detected by scanning the optical system 120 with a one-dimensional array detector 187 in one direction, e.g., in the Y-axis direction in the figure. It is also possible to detect the output light rays simultaneously with a two dimensional detector 189, as shown in FIG. 35(c).

In the present invention, laser light from a continuous dye laser, pulsed dye laser, YAG laser, semiconductor laser, etc., may be used. Examples of detectors usable in the present invention are semiconductor detectors which are capable of detecting light rays in the visible and near infrared regions, such as a photodiode, photodiode array, MOS array, CCD sensor, etc., and photoelectric emission type detectors such as an image orthicon, vidicon, etc. Examples of detectors with multiplier function which is usable in the present invention are a combination of a dynode or avalanche diode and a secondary-electron detector, a detector in which secondary electron multiplication is effected by a microchannel plate and a fluorescent image on a fluorescent screen is detected by a diode array, vidicon, image orthicon or the like, and so forth.

FIG. 36 shows a highly directional optical element that is used in the optical sectional image forming apparatus according to the present invention. In the figure, reference numeral 100 denotes a highly directional optical element, 103 a light absorbing material, 105 a core, and 107 a cladding.

Figure 36A:
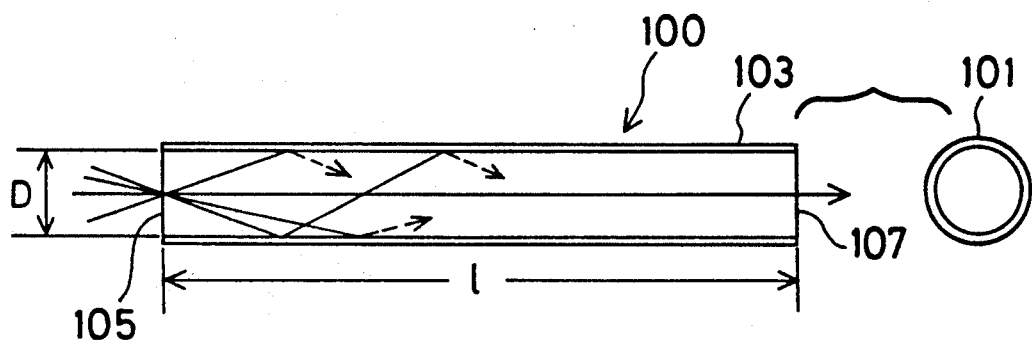
FIGS. 36(a-b) shows a highly directional optical system according to the present invention.

Referring to FIG. 36(a), which shows an arrangement that is equivalent to that shown in FIG. 18, the highly directional optical element 100 comprises, for example, a hollow, straight, long and thin glass fiber the inner wall surface of which is coated with a light absorbing material, e.g., carbon. Rays which are parallel to the optical axis of the optical element 100 travel in straight lines and emerge from an exit end face 107, but rays which are at angles to the optical axis impinge upon the wall surface and are absorbed by the absorbing material 103 without emerging from the exit end face 107.

Figure 36B:
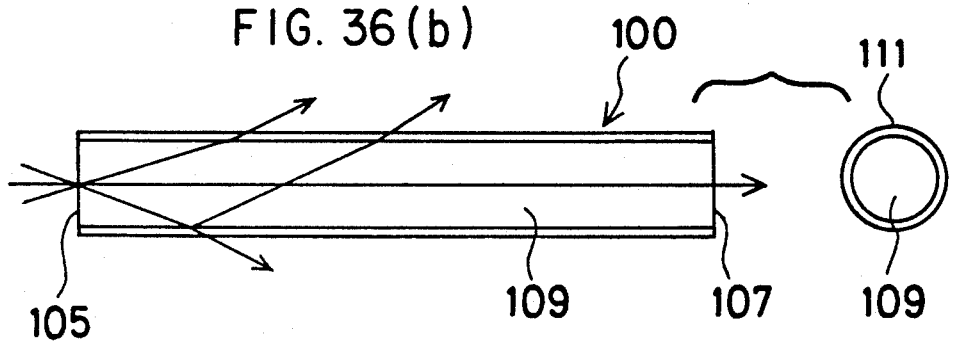

FIG. 36(b) shows an arrangement in which, contrary to ordinary optical fibers, the refractive index of a core 109 is smaller than that of a cladding 111. Thus, rays which are not parallel to the optical axis are scattered and lost without being totally reflected by the cladding 111. Even if such rays are partially reflected, all the rays which are not parallel to the optical axis are lost outside the optical element while repeating the reflection some times. Eventually, a plane wave that is parallel to the optical axis alone can be taken out from the exit end face 107. The arrangements shown in FIGS. 36(a) and 36(b) may be combined together, that is, the inner surface of the cladding 111 may be coated with a light absorbing material.

Figure 37:
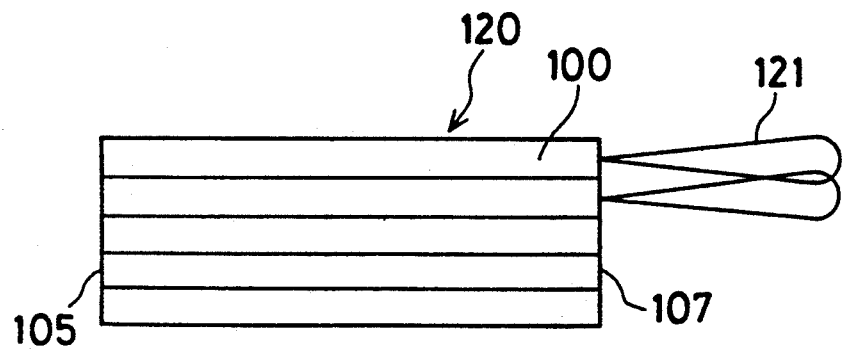
FIG. 37 shows an optical system which comprises a bundle of highly directional optical systems of the type shown in FIG. 36.

FIG. 37 shows an embodiment which comprises a plurality of highly directional optical elements of the type shown in FIG. 36, which are bundled together in a circular cylinder shape. In the figure, reference numeral 120 denotes a highly directional optical system, and 121 a radiation directional pattern. The radiation directivity is determined by the wavelength λ of the incident light and the diameter D of the optical element 100: the smaller the diameter D, the closer to the spherical wave radiation.

If a plurality of highly directional optical elements 100 are bundled together in a circular cylindrical shape to form a highly directional optical system 120, as illustrated, emergent light, shown by the radiation directional pattern 121, can be obtained from each highly directional optical element. Therefore, if light that contains scattered rays and a plane wave is made incident on the emergence end face, the light becomes an approximately point-like source as a Fraunhofer diffraction image produced by the plane wave and emerges from the exit end face 107, and by detecting it, only the plane wave can be detected resultingly. Accordingly, if the light-receiving surface of the highly directional optical system 120 is arranged to have a predetermined size, light transmitted by a human body or the like can be simultaneously detected in a predetermined range, so that the optical system 120 can be used as a high-resolution detector for obtaining an optical sectional image.

Figure 38:
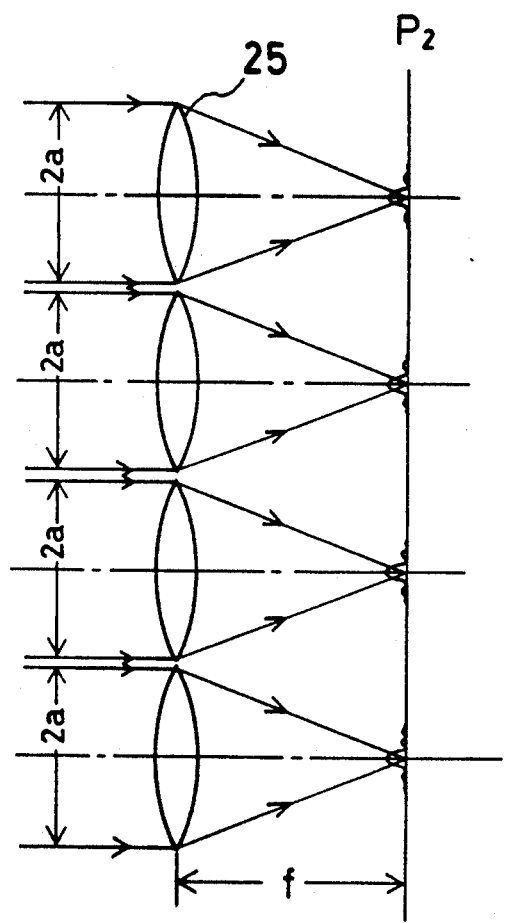
FIG. 38 shows an optical system which comprises a bundle of telescopes.

FIG. 38 shows an embodiment which comprises a bundle of optical elements each using the long focus lens shown in FIGS. 19 and 20 to form a Fraunhofer diffraction image on the focal plane, thereby shortening the length of the optical system. Thus, an optical sectional image can be obtained by use of a relatively short optical system.

Figure 39A:
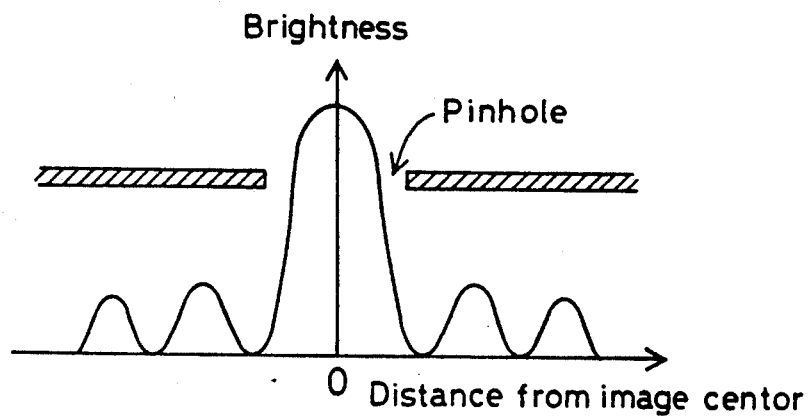
FIGS. 39(a-b) are views for explanation of a method of taking out a 0-order spectrum.
Figure 39B:
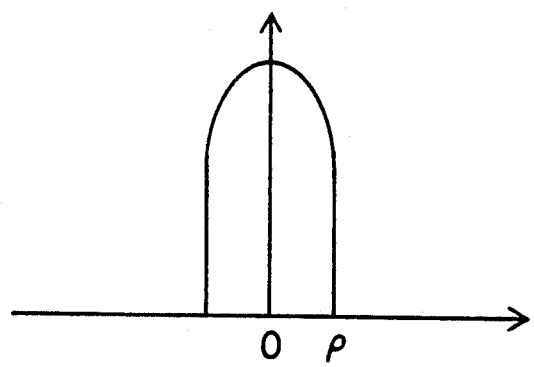
Figure 40:
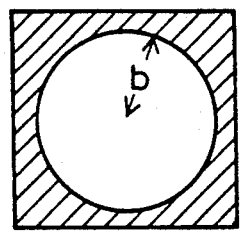
FIGS. 40(a-d) show various entrance aperture configurations and the corresponding Fraunhofer diffraction images.
Figure 40:
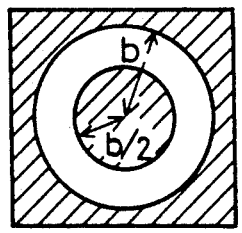
Figure 40:
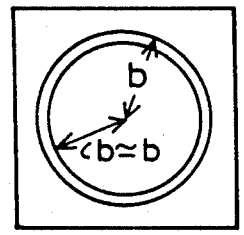

Incidentally, the above-described optical system is designed to cut higher-order components of a Fraunhofer diffraction image by use of a circular pinhole to detect the 0-order spectrum only, as shown in FIG. 39(a), and this system may be considered to be equivalent to a function such as that shown in FIG. 39(b). The illustrated pattern corresponds to the arrangement of the optical system in which the aperture at the entrance end has a circular configuration. When the configuration of the entrance aperture is varied, the Fraunhofer diffraction spectrum changes as shown in FIG. 40.

Figure 40D:
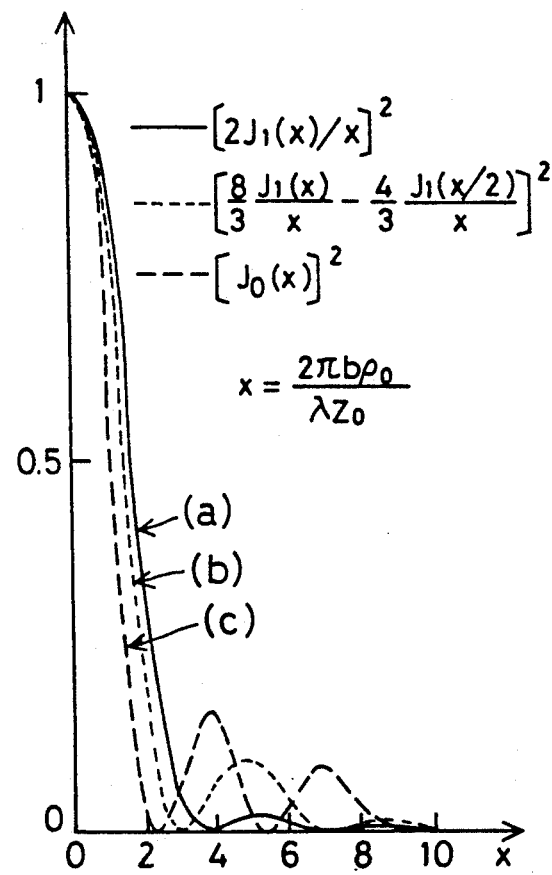

FIG. 40(a) shows a circular entrance aperture; FIG. 40(b) shows an annular entrance aperture; FIG. 40(c) shows a slit-shaped annular entrance aperture; and FIG. 40(d) shows Fraunhofer diffraction spectra corresponding to these entrance apertures. As will be clear from the figures, the three different entrance aperture configurations show similar Fraunhofer diffraction patterns, with a little difference in the width of the 0-order spectrum. In the case of a rectangular entrance aperture, a Fraunhofer diffraction image is formed in which circular patterns line up orthogonally about the optical axis. Any of the above-described configurations may be applied to the present invention as long as spectra other than the 0-order spectrum on the optical axis are cut off by a pinhole.

FIG. 41 is a view for explanation of Fraunhofer diffraction images produced when the transmittance of a pupil of a highly directional optical system is changed.

Figure 41A:
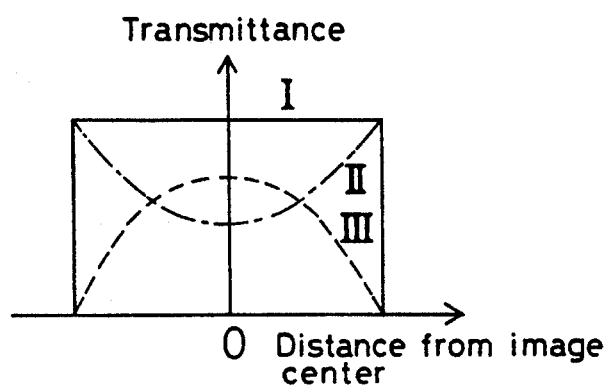
FIGS. 41(a-b) show the relationship between the transmittance distribution of the pupil function and the Fraunhofer diffraction image.
Figure 41B:
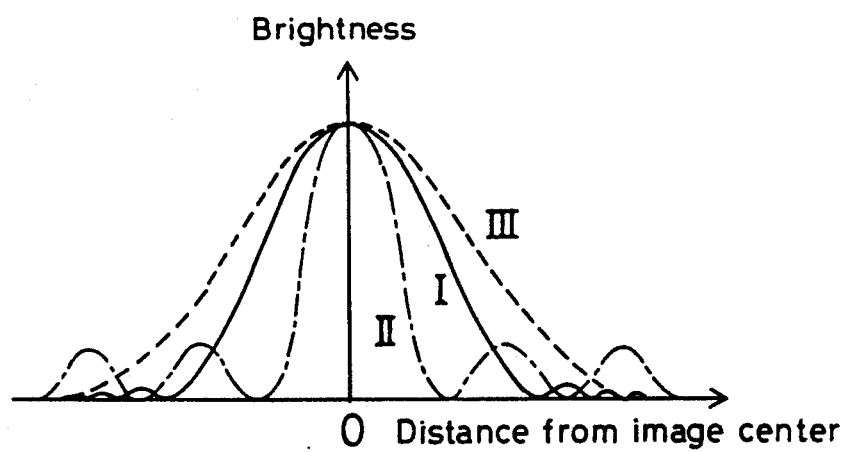

When the transmittance of the pupil is constant (I), as shown in FIG. 41(a), a Fraunhofer diffraction image I shown in FIG. 41(b) is formed. When the transmittance of the pupil changes along a square curve so that the transmittance at the center is the lowest (II), a Fraunhofer diffraction image II is formed, whereas, when the transmittance of the pupil changes along a square curve so that the transmittance at the center is the highest (III), a Fraunhofer diffraction image III is formed. The type II provides the narrowest width of the 0-order spectrum and hence enables an improvement in the spatial resolving power. In the case of the type III, the width of the 0-order spectrum is relatively wide, so that the spatial resolving power lowers. In both the type II and the type III, the energy loss of the received light is large in comparison to the type I, but the width of the 0-order Fraunhofer diffraction pattern is changed in compensation for the energy loss. Accordingly, when it is desired to change the 0-order Fraunhofer diffraction pattern at the exit of the highly directional optical element, the above-described apodization should be effected at the sacrifice of the received light energy.

Figure 42:
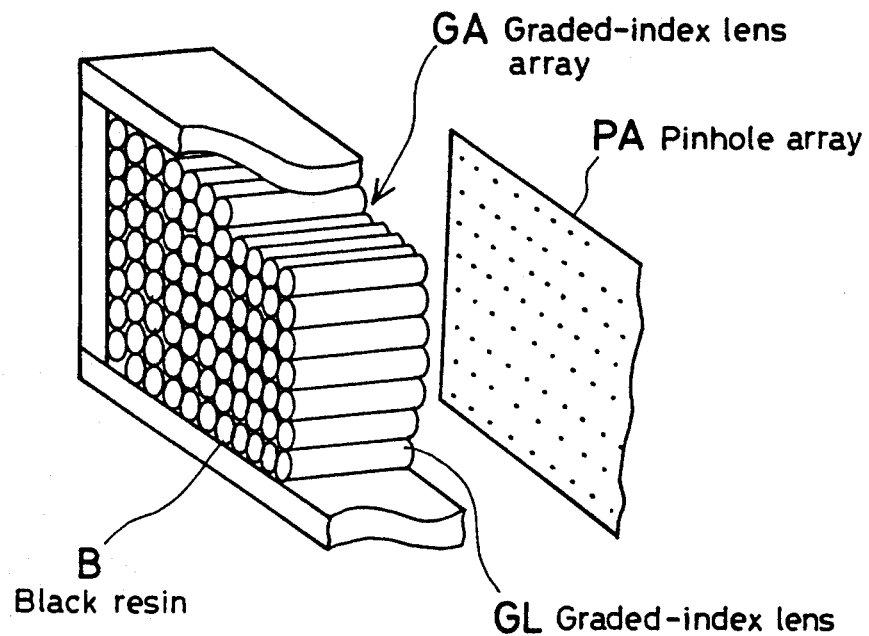
FIGS. 42 to 49 illustrate embodiments of a multiple beam highly directional optical system employed in the highly directional optical system according to the present invention.
Figure 43:
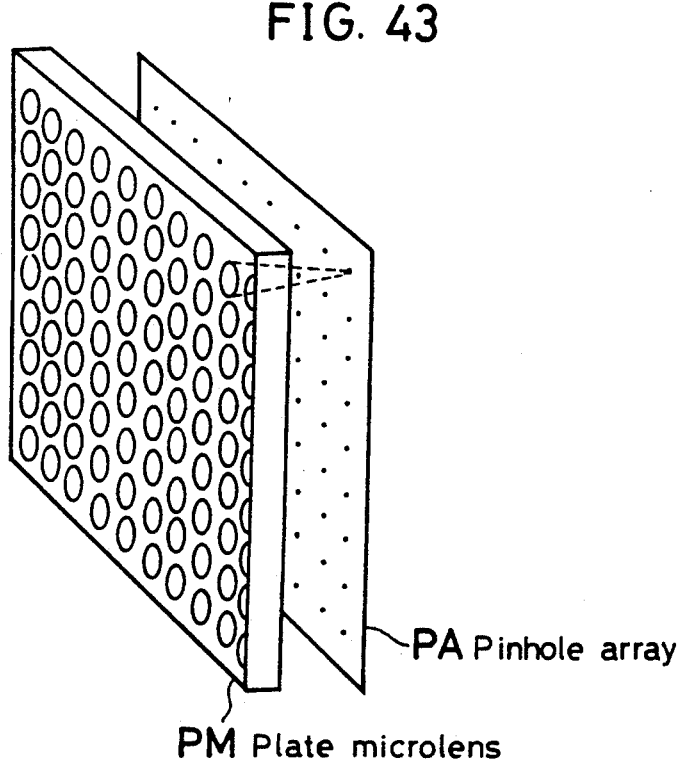
Figure 44:
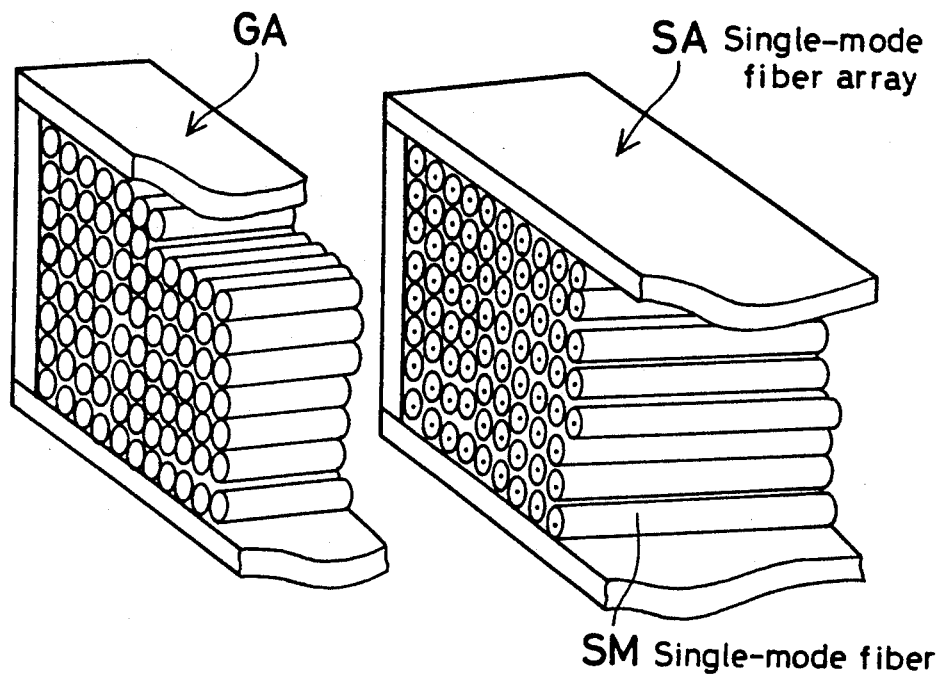
Figure 45:
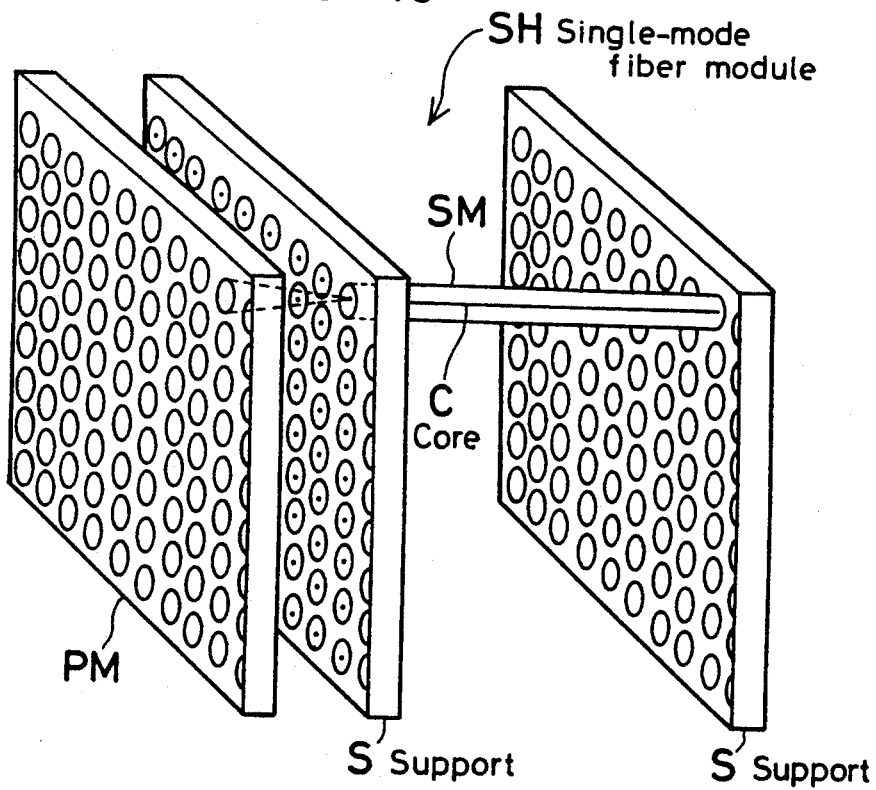

Next, embodiments of the multiple beam highly directional optical system in which the emergent light is scattered light will be explained with reference to FIGS. 42 to 45. The multiple beam highly directional optical system shown in FIG. 42 is equivalent to an arrangement which comprises a large number of highly directional optical elements of the type shown in FIG. 23(a), which are arranged side by side with each other. First, a large number of similar graded-index lenses GL are stacked up regularly and bonded to each other by means of an adhesive B comprising, for example, a black silicone resin material, so that no light will leak to the back through gaps which would otherwise be present, thereby forming a graded-index lens aray GA. A pinhole array PA is brought into close contact with the back surface of the graded-index lens array GA. Each pinhole in the pinhole array PA is provided to coincide with the axis of the corresponding graded-index lens GL. Accordingly, when a plane wave having a two-dimensional intensity distribution enters the graded-index lens aray GA from the front thereof, the intensities of light rays passing through the pinholes in the pinhole array PA differ from each other according to the intensity distribution. It is therefore possible to measure the two-dimensional intensity distribution of the plane wave by disposing discrete photodetectors in the rear of the respective pinholes, or disposing a two-dimensional photodetector in the rear of the pinhole array PA. The multiple beam highly directional optical system that is shown in FIG. 43 is equivalent to an arrangement in which a large number of highly directional optical elements of the type shown in FIG. 22 are arranged side by side with each other. In this case, however, a plate microlens PM is employed in place of an array of objective lenses. The plate microlens PM may be produced by regularly forming minute lenses in the form of an array on a transparent plate by use, for example, of a photolithographic technique, or by regularly forming graded-index lenses in the form of an array by a technique, for example, ion exchange, ion implantation, etc. Then, a pinhole array PA having pinholes at respective positions corresponding to the focal points of the minute lenses is disposed on the focal plane of the plate microlen PM, thereby making it possible to form a multiple beam highly directional optical system similar to that shown in FIG. 42. The multiple beam highly directional optical system that is shown in FIG. 44 is equivalent to an arrangement in which a large number of highly directional optical elements of the type shown in FIG. 27 are arranged side by side with each other. More specifically, a single-mode fiber array SA, which is formed by arranging a large number of single-mode fibers SM in correspondence to the respective axes of the graded-index lenses of the graded-index lens array GA shown in FIG. 42, is brought into close contact with the back surface of the lens array GA. That is, the single-mode fiber array SA is employed in place of the pinhole array PA shown in FIG. 42 to form an optical system that performs a similar function. The multiple beam highly directional optical system that is shown in FIG. 45 employs a single-mode fiber module SH, which is similar to the single-mode fiber array SA, in place of the pinhole array PA shown in FIG. 43. The module SH comprises supports S, each having a large number of apertures each of which is centered at the focal point of the corresponding minute lens of the plate microlens PM and which has a diameter equal to that of a single-mode fiber SM, and single-mode fibers SM which are regularly arranged with the entrance and exit ends of each single-mode fiber SM being inserted into the corresponding openings.

Figure 29:
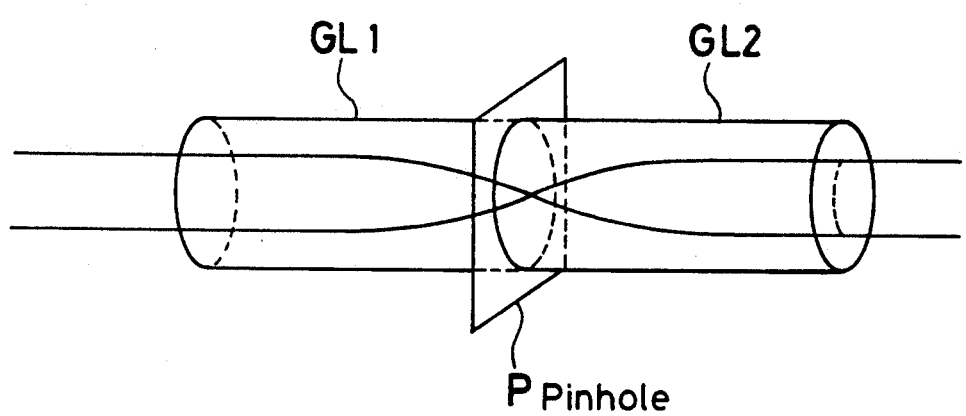
Figure 30A:
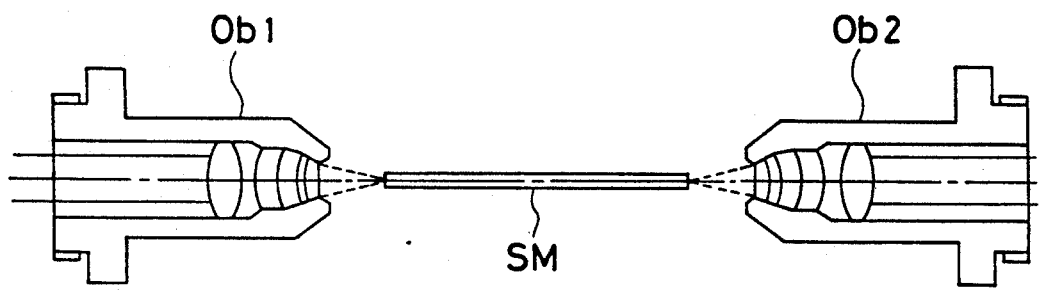
Figure 30B:
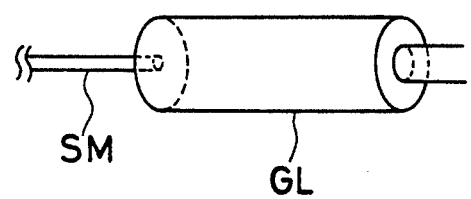
Figure 31:
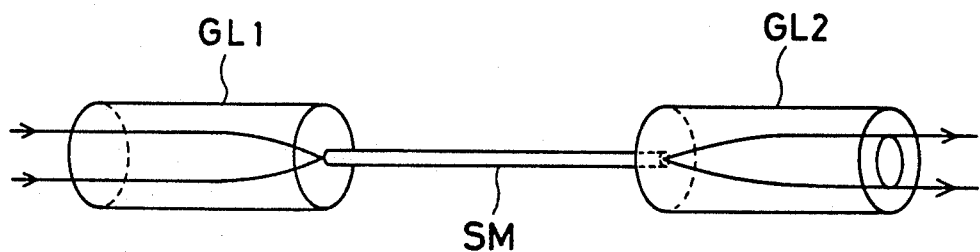
Figure 46:
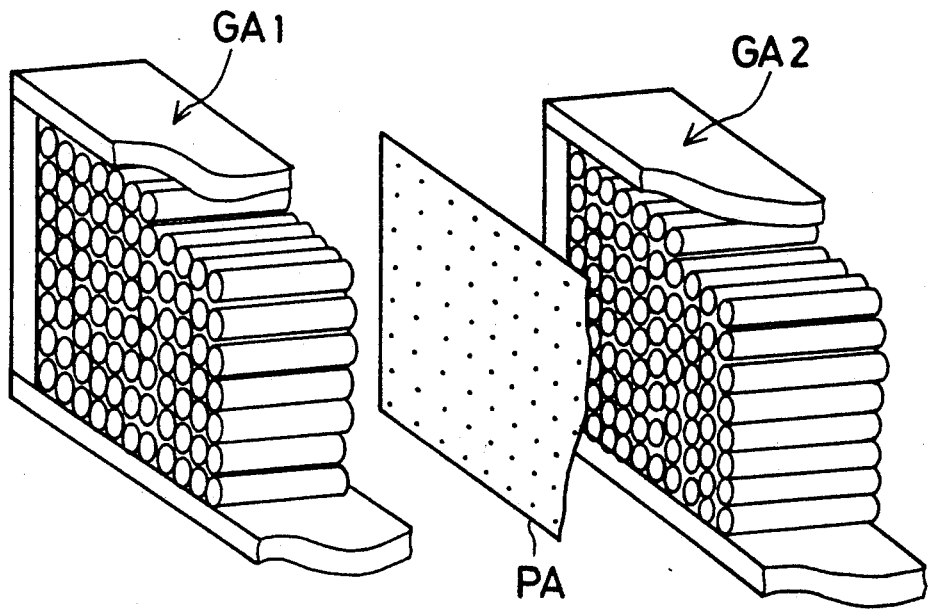
Figure 47:
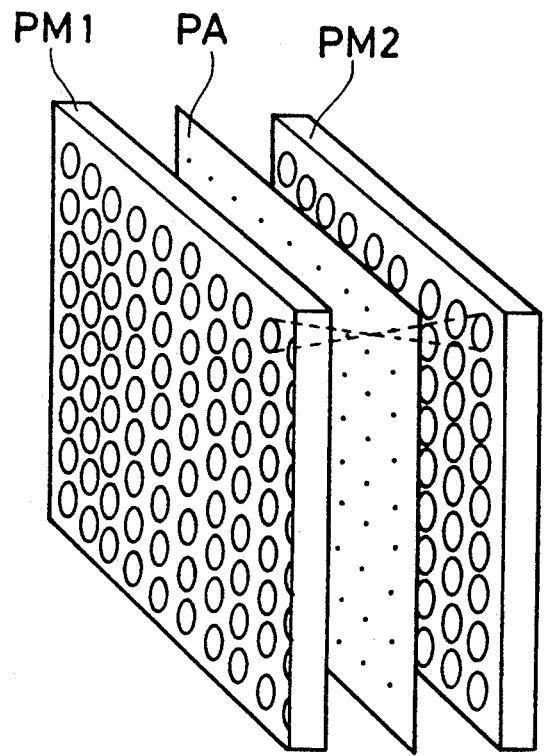
Figure 48:
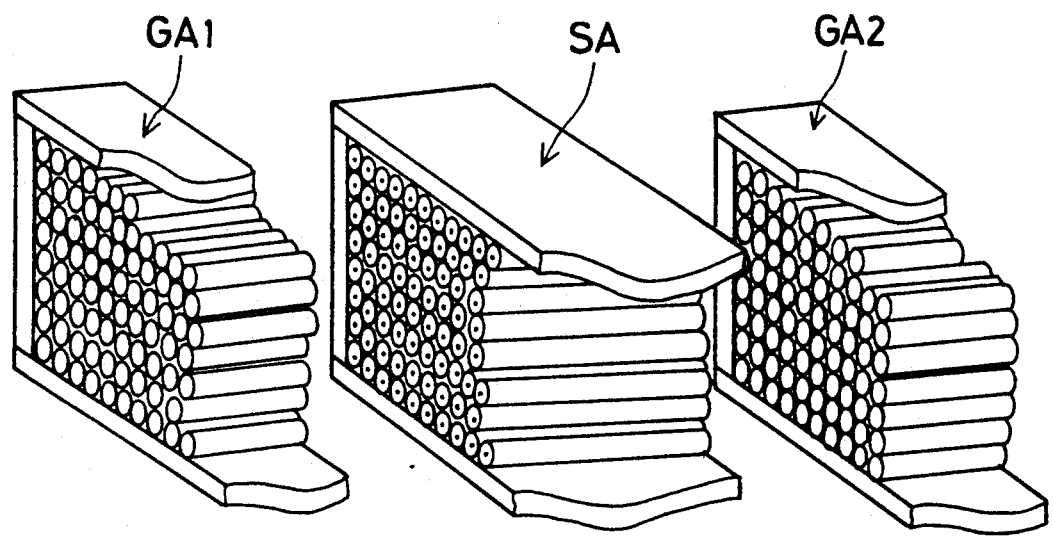
Figure 49:
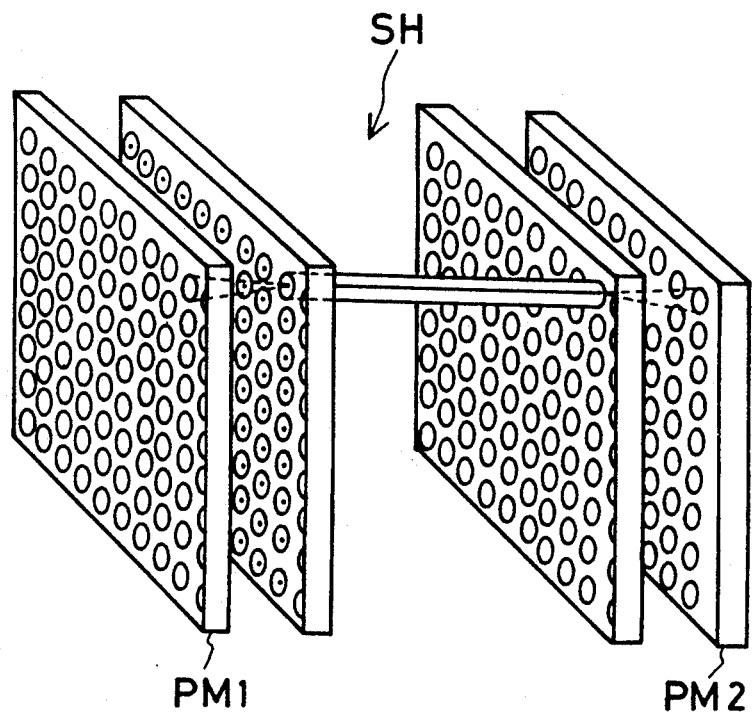

The multiple beam highly directional optical systems shown in FIGS. 42 to 45 are arranged such that the emergent light is divergent light, as stated above. When the emergent light comes out in the form of divergent light from the exit point on the back surface of the pinhole array PA or the like, a detector such as a two-dimensional photodetector cannot be disposed at a long distance from the ponhole array PA or the like (i.e., if the former is a long distance apart from the latter, adjacent channels interfere with each other, so that the intensity distribution cannot be measured). Embodiments of multiple beam highly directional optical systems which are capable of outputting emergent light in the form of a plane wave having a similar distribution to that of the incident light will next be explained with reference to FIGS. 46 and 47. The multiple beam highly directional optical system that is shown in FIG. 46 is equivalent to an arrangement in which a large number of highly directional optical elements of the type shown in FIG. 29 are arranged side by side with each other. This optical system is formed by disposing a pinhole array PA in between two graded-index lens arrays GA1 and GA2 explained in conjunction with FIG. 42 and bringing these three members into close contact with each other with the axis of each graded-index lens being aligned with the corresponding pinhole in the pinhole array PA. With this arrangement, an incident plane wave having a two-dimensional intensity distribution emerges in the form of a plane wave having a similar two-dimensional intensity distribution, with scattered light eliminated by the multiple beam highly directional optical system. Accordingly, even if a detector, for example, a two-dimensional photodetector, is disposed at a certain distance from the multiple beam highly directional optical system, a two-dimensional intensity distribution can be measured. The multiple beam highly directional optical system that is shown in FIG. 47 is formed by disposing a second plate microlens PM2 in the rear of the multiple beam highly directional optical system shown in FIG. 43 in a confocal manner. The multiple beam highly directional optical system that is shown in FIG. 48 is equivalent to an arrangement in which a large number of highly directional optical elements of the type shown in FIG. 31 are arranged side by side with each other. No detailed description will be needed. The multiple beam highly directional optical system that is shown in FIG. 49 is formed by disposing a second plate microlens PM2 in the rear of the multiple beam highly directional optical system shown in FIG. 45 such that the front focal point of each lens of the second plate microlens PM2 is coincident with the core at the exit end of the corresponding single-mode fiber of the module SH.

By combining together a multiple beam highly directional optical system such as those shown in FIGS. 42 to 49 and a two-dimensional photodetector, it is possible to form a highly directional optical system which is capable of detecting with high sensitivity a plane wave with a two-dimensional intensity distribution that enters from a predetermined direction while separating it from the background light such as scattered light.

Figure 50:
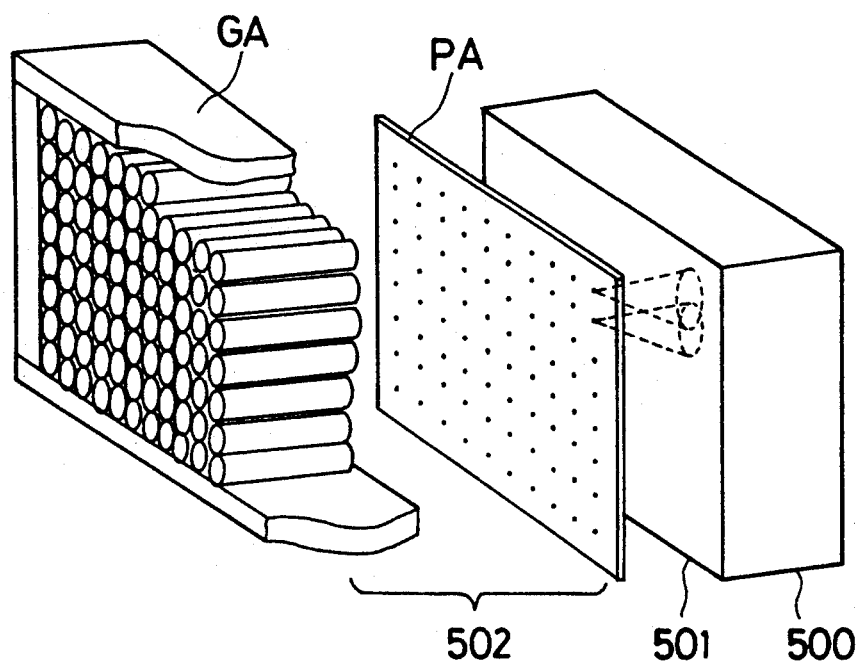
FIGS. 50 to 53 illustrate other embodiments of the highly directional optical system according to the present invention.
Figure 51:
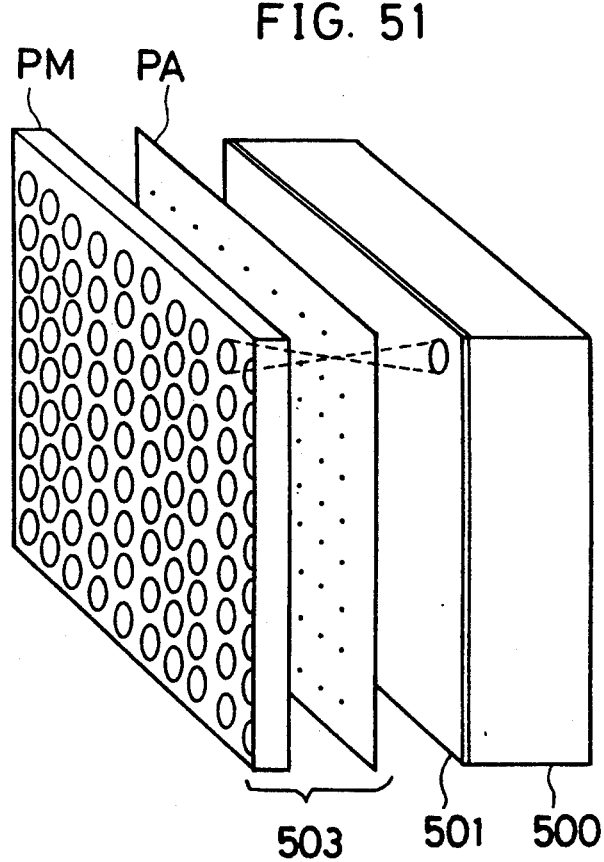
Figure 52:
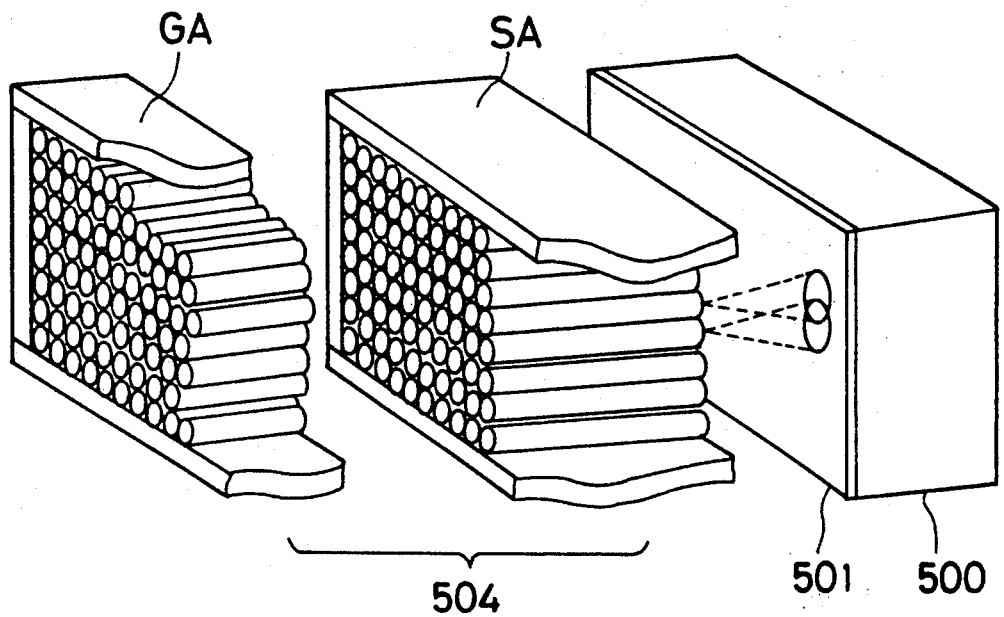
Figure 53:
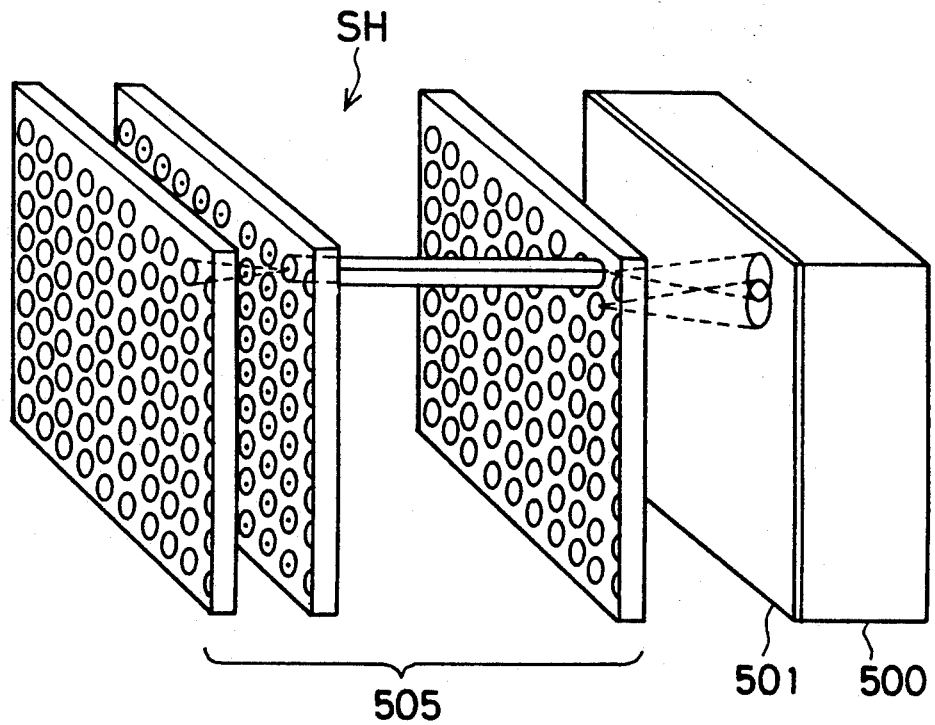
Figure 54:
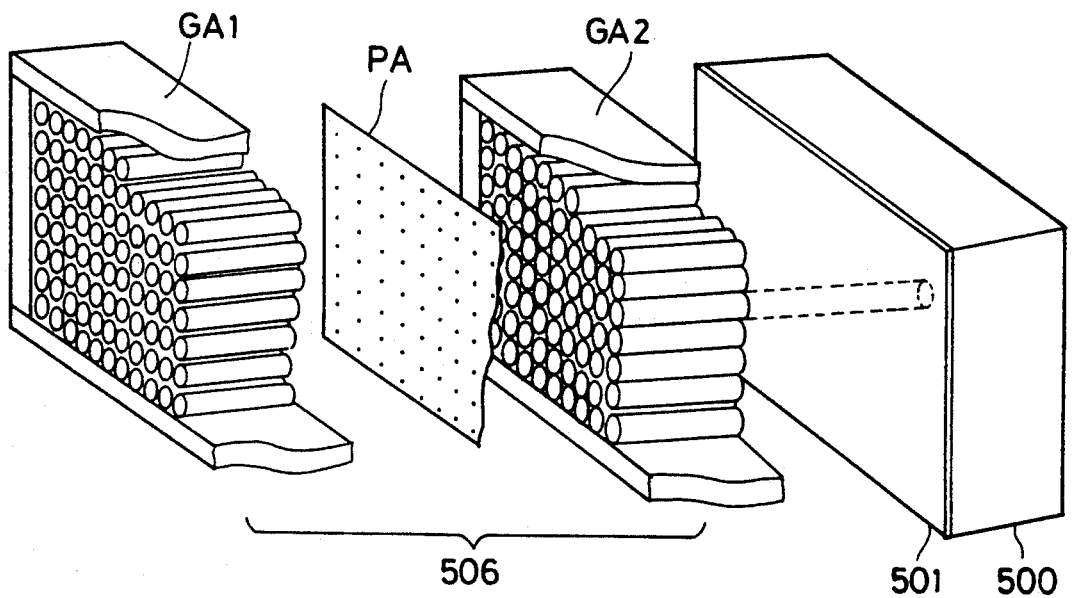
FIGS. 54 to 57 illustrate other embodiments of the highly directional optical system according to the present invention.
Figure 55:
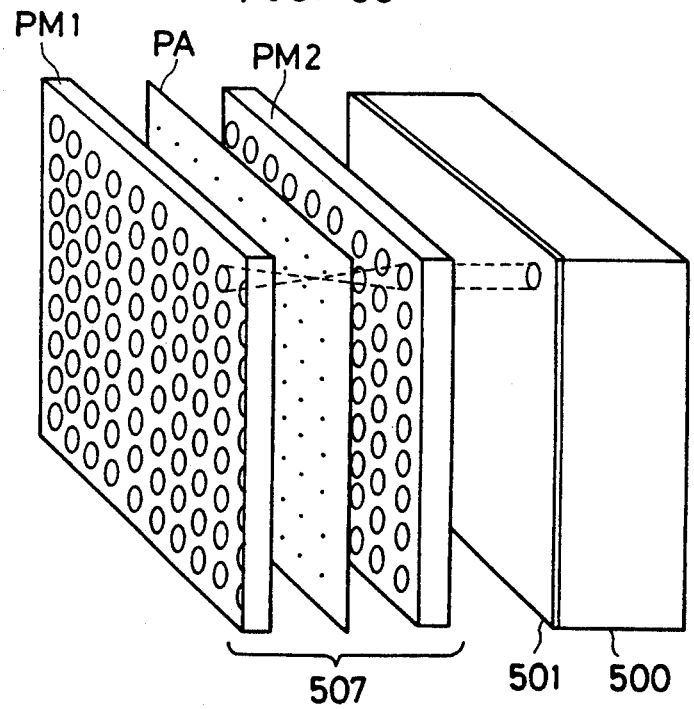
Figure 56:
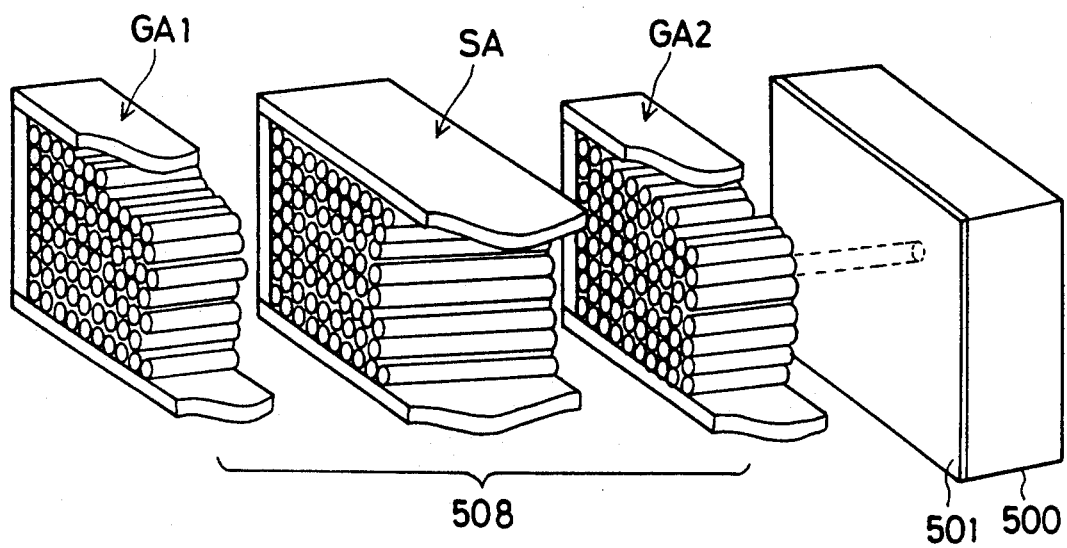
Figure 57:
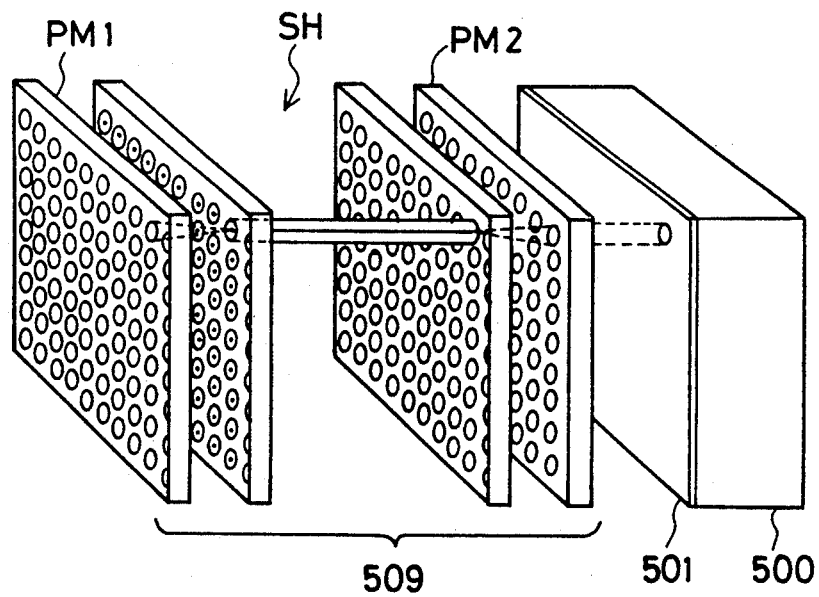

FIG. 50 shows a highly directional optical system that comprises the multiple beam highly directional optical system 502 shown in FIG. 42 and a two-dimensional photodetector 500 which is disposed at the exit side of the optical system 502. FIG. 51 shows a highly directional optical system that comprises the multiple beam highly directional optical system shown in FIG. 43 and a two-dimensional photodetector 500 which is disposed at the exit side of the optical system 503. FIG. 52 shows a highly directional optical system that comprises the multiple beam highly directional optical system 504 shown in FIG. 44 and a two-dimensional photodetector 500 which is disposed at the exit side of the optical system 504. FIG. 53 shows a highly directional optical system that comprises the multiple beam highly directional optical system 505 shown in FIG. 45 and a two-dimensional photodetector 500 which is disposed at the exit side of the optical system 505. In the highly directional optical systems shown in FIGS. 50 to 53, light that emerges from the multiple beam highly directional optical systems 502 to 504 is light that diverges from each pinhole in the pinhole array PA or from the exit end of each single-mode fiber, as illustrated. Therefore, if the photoelectric conversion surface 501 of the two-dimensional photodetector 500 is disposed at a long distance from the exit end face of each of the multiple beam highly directional optical systems 502 to 504, adjacent channels interfere with each other, so that the intensity distribution cannot be measured accurately. Accordingly, the two-dimensional photodetector 500, which is employed in combination with the multiple beam highly directional optical systems 502 to 504, must be designed so that the photoelectric conversion surface 501 can be brought into close contact with the optical systems 502 to 504. As for the method of reading out light intensities at two-dimensional positions by the two-dimensional photodetector 500, if an intensity that is detected at a position corresponding to the center of the exit end of each highly directional optical element alone is read out, a plane wave from a predetermined direction can be separated from the other scattered light with high resolving power.

FIGS. 54 to 57 respectively show highly directional optical systems comprising the multiple beam highly directional optical systems 506 to 509 shown in FIGS.

46 to 49 and a two-dimensional photodetector 500 which is disposed at the exit side of each of the optical systems 506 to 509. In these multiple beam highly directional optical systems 506 to 509, an incident plane wave having a two-dimensional intensity distribution emerges in the form of a plane wave having a similar two-dimensional intensity distribution, wit scattered light eliminated by the multiple beam highly directional optical systems, as stated above. Accordingly, even if the photoelectric conversion surface 501 of the two-dimensional photodetector 500 is disposed at a certain distance from the exit end surface of the multiple beam highly directional optical systems 506 to 509, a two-dimensional intensity distribution can be measured accurately.

Figure 58:
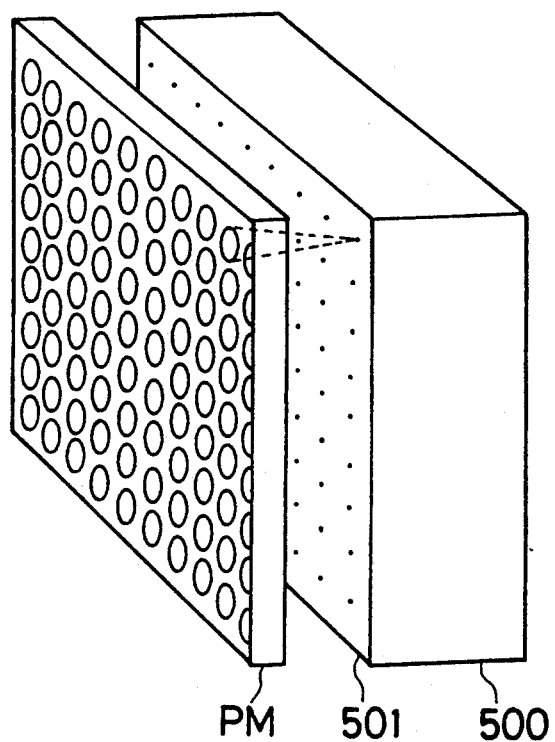
FIGS. 58 and 59 illustrate other embodiments of the highly directional optical system according to the present invention.
Figure 59:
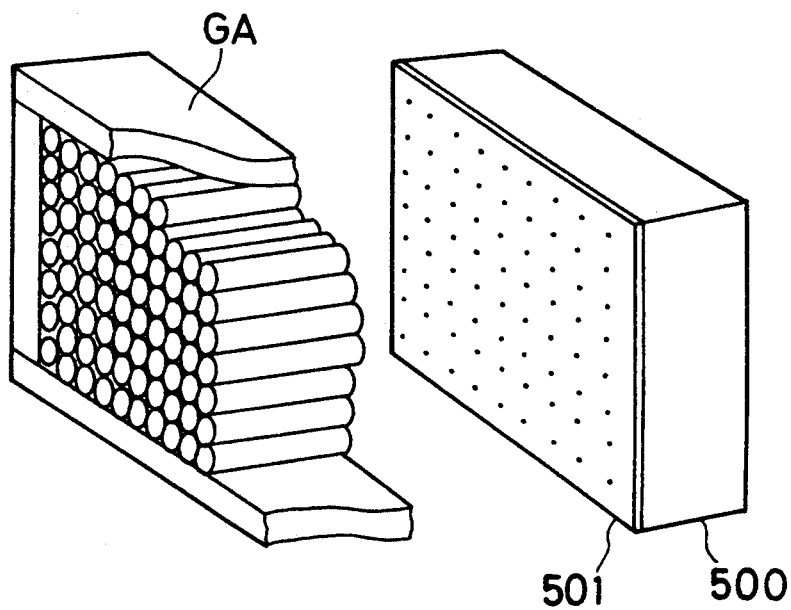
Figure 60A:
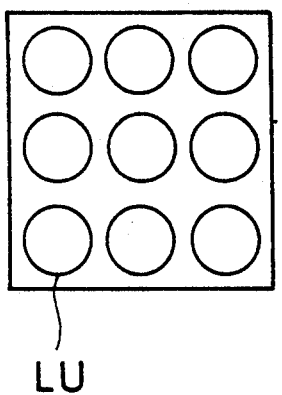
FIGS. 60(a-c) illustrate the function of the highly directional optical system according to the present invention.
Figure 60B:
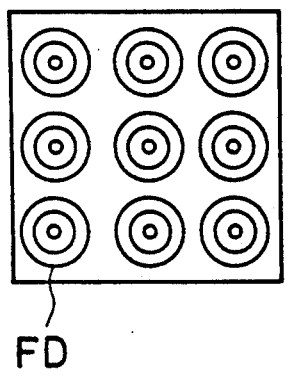
Figure 60C:
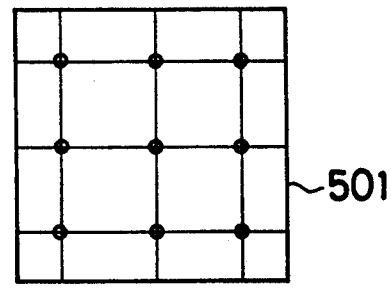

Incidentally, the above-described highly directional optical systems that are shown in FIGS. 50 to 57 employ the multiple beam highly directional optical systems 502 to 509. However, the function of the pinhole array PA, single-mode fiber array SA or single-mode fiber module SH of the multiple beam highly directional optical systems 502 to 505, that is, the function of taking out only a zero-order diffraction pattern of a Fraunhofer diffraction image produced by each objective lens or graded-index lens, may be assigned to the two-dimensional photodetector 500 that performs an intensity image reading operation, and the pinhole array PA, single-mode fiber array SA or single-mode fiber module SH may be omitted. More specifically, as shown in FIGS. 58 and 59, a highly directional optical system may be comprised of either a plate microlens PM or a convex lens array, e.g., a graded-index lens array GA, and a two-dimensional photodetector 500 whose photoelectric conversion surface 501 is disposed on a focal plane of the plate microlens PM or the lens array GA. With this arrangement, when a plane wave enters such a highly directional optical system, a Fraunhofer diffraction image FD such as that shown in FIG. 60(b) is formed on the focal plane of each unit convex lens LU of a lens array such as that shown in FIG. 60(a) by the lens function, and in order to read out only a zero-order diffraction pattern of each Fraunhofer diffraction image FD, intensities only at the positions indicated by the mark ○ in FIG. 60(c) are read out by sampling. By doing so, the sampling operation realizes the same function as that of the pinhole array PA shown in FIG. 50 or 51. Accordingly, the highly directional optical system of the present invention can also be formed from only a convex lens array and a two-dimensional photodetector which is disposed on a focal plane thereof, without a pinhole array PA.

There is no particular restriction on the type of two-dimensional photodetector that is employed in combination with the multiple beam highly directional optical systems 502 to 509, or the plate microlens PM, or the graded-index lens array GA or other convex lens array. Any type of existing two-dimensional photodetector can be employed. Examples of two dimensional photodetectors usable in the present invention will be shown below.

Two-dimensional photodetectors, which convert two-dimensional light intensity distributions into electrical image signals, may be roughly classifed into solid-state image sensors and photoelectric conversion image sensors. Examples of solid-state image sensors include a parallel independent processing photodiode array shown in FIG. 61, a charge-coupled device (CCD) type image sensor shown in FIG. 62, and a field-effect transistor (MOS) type image sensor shown in FIG. 63.

Figure 61:
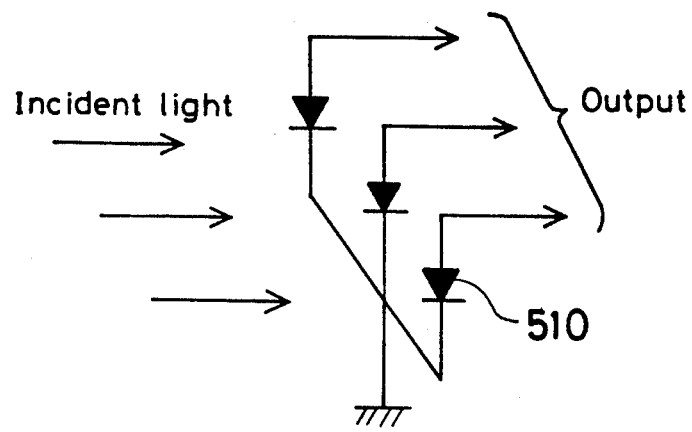
FIGS. 61 to 69 illustrate examples of two-dimensional photodetectors.

The parallel independent processing photodiode array is arranged such that photodiodes 510 with photovoltaic effect are arranged in the form of an array and wired, as shown in FIG. 61, so that an output of each photodiode can be taken out directly. Since a signal can be independently extracted from each photodiode, it is possible to access a specific photodiode according to need and perform parallel independent processing of signals from the photodiodes, for example, processing of changing over a signal having the background light removed therefrom (i.e., AC component signal) and a signal having the background light left therein (i.e., DC component signal) from one to the other.

Figure 62:
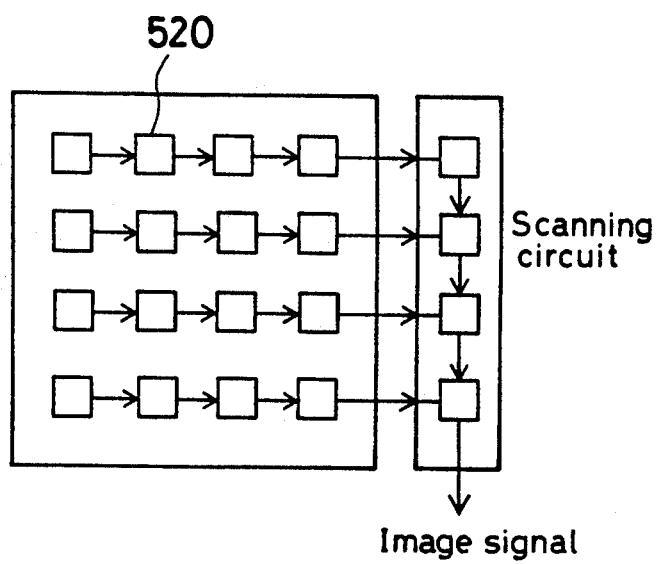

The CCD type image sensor is arranged such that a p-type layer is formed on, for example, an n-type silicon wafer by diffusion or or epitaxial growth and then electrodes are provided thereon in such a manner that picture elements 520 each comprising three electrodes are arranged in a matrix, as shown in FIG. 62. By sequentially and selectively switching the voltage applied to three electrodes constituting each picture element, a signal charge (e.g., holes) generated by the incident light is sequentially transferred, thereby taking out an image signal. By cooling CCD, it is possible to reduce the dark current and fixed noise, which are generated at ordinary temperatures.

Figure 63:
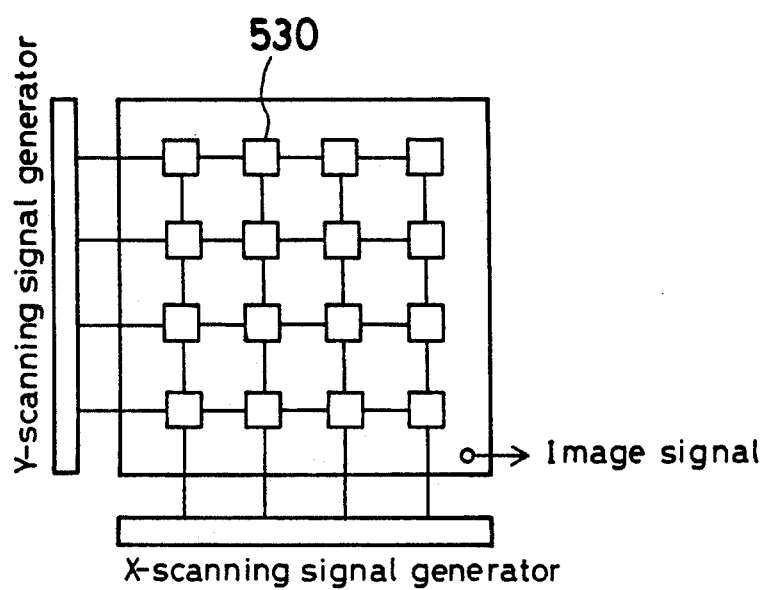

The MOS type image sensor is arranged such that picture elements 530 each comprising two electrodes which correspond respectively to X- and Y-coordinates are arranged in a matrix, as shown in FIG. 63, and each picture element constitutes a switching circuit together with a scanning circuit formed from MOS type field-effect transistor. To take out an image signal from the sensor, scanning pulses are applied to the picture elements from X- and Y-axis scanning signal generators shown in FIG. 63, and signal charges that are generated in the picture elements in response to the incident light are taken out as a signal current from picture elements whose electrodes corresponding to the X- and Y-axes are 0 in voltage.

Figure 64:
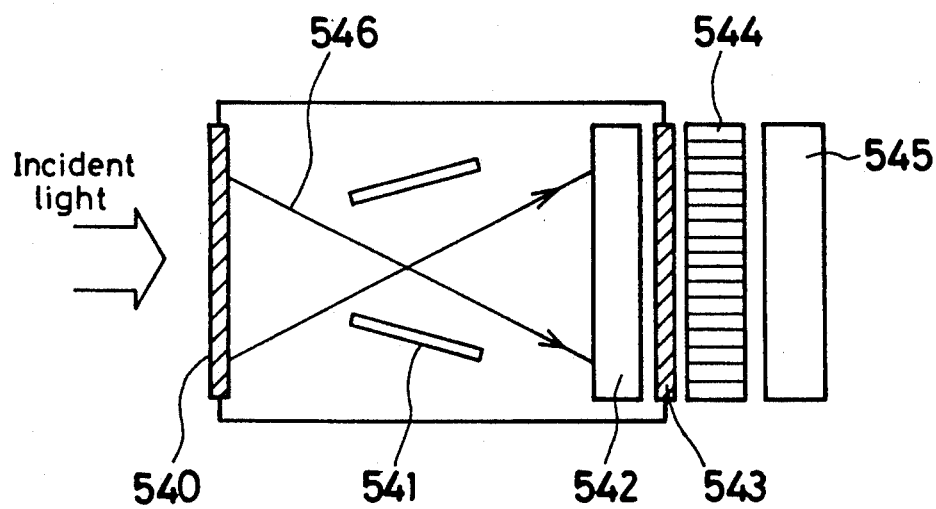
Figure 65:
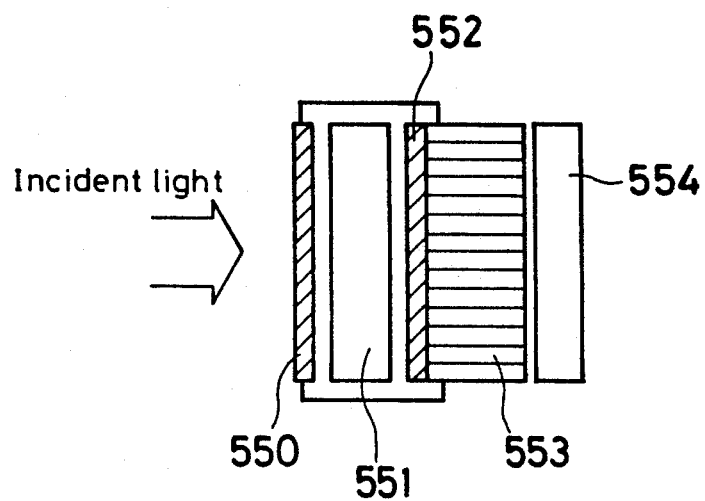
Figure 66:
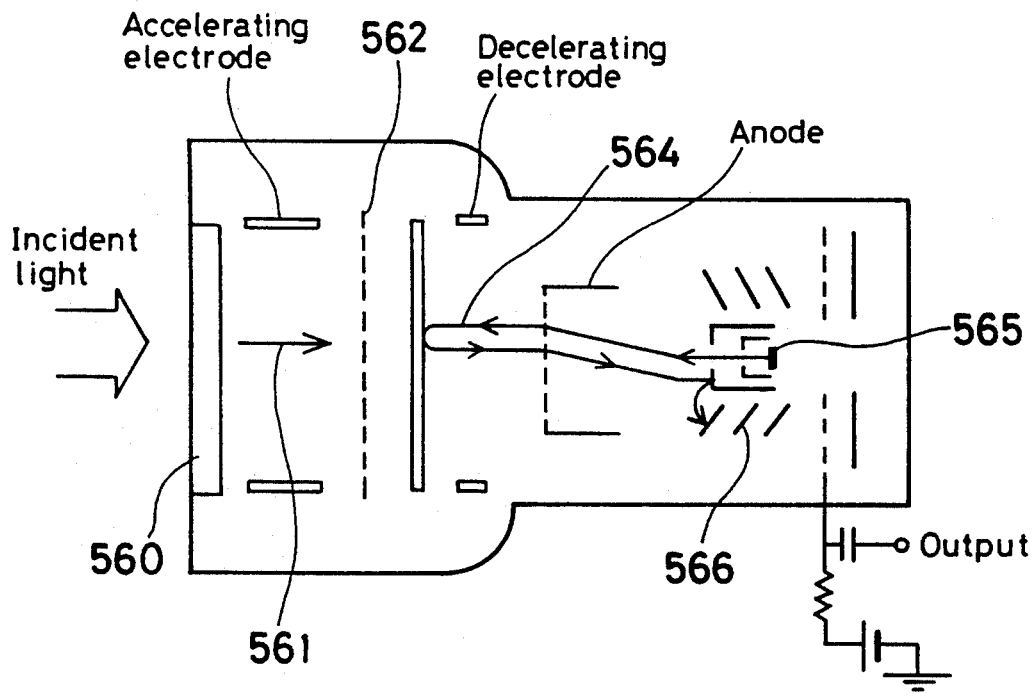
Figure 67:
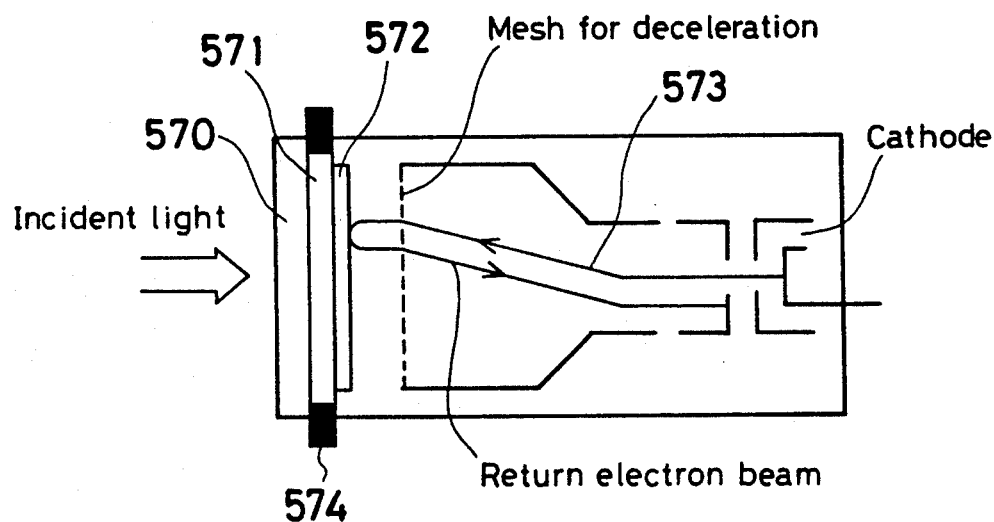
Figure 68:
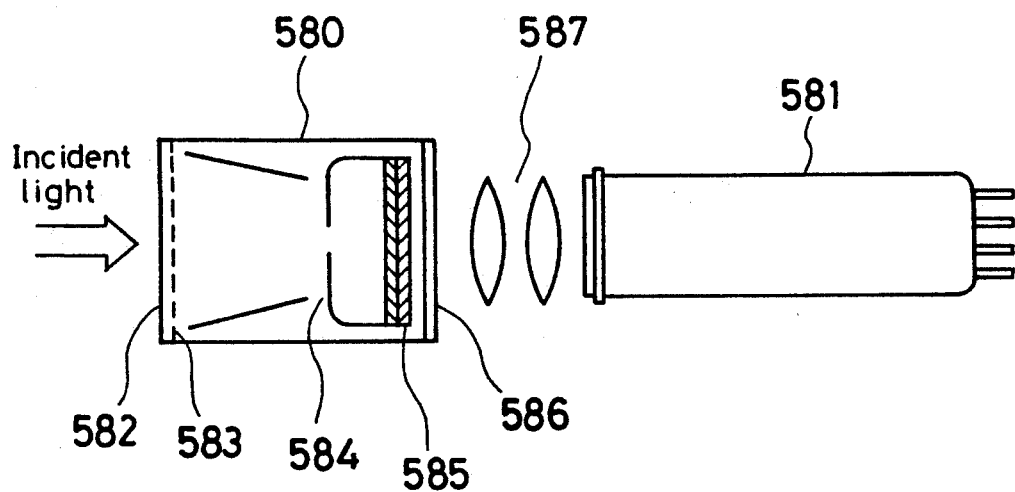
Figure 69:
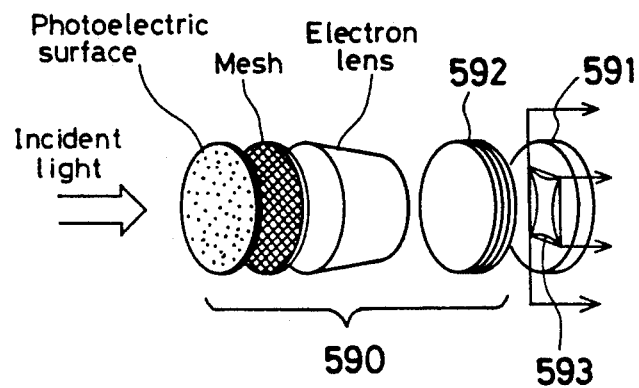

Examples of photoelectric conversion image sensors include a static focus MCP diode array which comprises a combination of a microchannel plate (MCP) and a diode array, as shown in FIG. 64, a proximity MCP diode array such as that shown in FIG. 65, an image orthicon shown in FIG. 66, a vidicon shown in FIG. 67, a photonic microscope system (VIM system) which comprises a combination of a MCP and a vidicon, as shown in FIG. 68, and a photocounting image acquisition system (PIAS) which comprises a combination of a MCP and a semiconductor position detecting element, as shown in FIG. 69.

In the static focus MCP diode array, as shown in FIG. 64, incident light causes emission of photoelectrons on a photoelectric surface 540, and the photoelectrons are accelerated and focused by an electron lens system 541 to enter a MCP 542. The electrons are multiplied in the MCP 542 and made incident on a fluorescent screen 543 to emit light. The light emitted from the fluorescent screen 543 enters a diode array 545 through optical fibers 544 to output an image signal.

In the proximity MCP diode array, as shown in FIG. 65, incident light causes emission of photoelectrons on a photoelectric surface 550, and the photoelectrons enter a MCP 551 directly. The electrons are multiplied in the MCP 551 and made incident on a fluorescent screen 552 to emit light. The light from the fluorescent screen 552 enters a diode array 554 through optical fibers 553 to output an image signal.

In the image orthicon, as shown in FIG. 66, photoelectrons 561 are emitted from a photoelectric cathode 560 in accordance with the incident light, and the photoelectrons 561 are accelerated to pass through a target mesh 562 and collide against a target (low-resistance glass plate with a thickness of several $\mu$m) 563. As a result, secondary electrons are emitted from the target 563 and these electrons are collected on a target mesh, so that a positive charge image corresponding to the incident light is formed on the target. When the target surface is scanned with an electron beam 564 in this state, the positive charge on the target surface is neutralized since a retarding field is formed near the target surface. The electrons left after the neutralization have been density-modulated by the positive charge on the target. The electron beam arrives near an electron gun 565 through substantially the same orbit as the previous electron orbit. The return electron beam is amplified by a secondary-electron multiplier 566 that is disposed near the electron gun 565, thereby outputting an image signal.

In the vidicon, a target has a structure in which a transparent conductive film 571 and a photoconductive film 572 with a high resistivity are stacked up on a transparent faceplate 570, as shown in FIG. 67. If there is incident light after scanning with an electron beam 573, electron-hole pairs are generated. The electrons flow through the transparent conductive film 571 to a signal electrode 574, whereas the holes move to the scanned surface of the photoconductuve film 572. When the surface of the photoconductive film 572 is scanned again with the electron beam 573, the electron beam flows into the target in accordance with the size of surface potential built up by the holes and comes out through the signal electrode 574 in the form of an image signal.

The VIM system comprises a combination of a two-dimensional photon counting tube 580 and a low-visual persistence vidicon 581, as shown in FIG. 68. Light that enters the two-dimensional photon counting tube 581 generates photoelectrons on a photoelectric surface 582, and the photoelectrons pass through a mesh 583 and an electron lens 584 to enter a MCP (a two-stage MCP in the example shown in FIG. 68) 585 where the photoelectrons are amplified and then strike on a fluorescent screen 586 as a plane of emergence to form bright dots, which are focused on a photoelectric surface of the low-visual persistance vidicon 581 through a lens system 587, thereby obtaining an image signal corresponding to the incident light from the output of the vidicon 581.

The PIAS system comprises a combination of a two-dimensional photon counting tube 590 similar to that employed in the VIM system (however, the photon counting tube 590 has a three-stage MCP) and a silicon semiconductor detecting element 591, as shown in FIG. 69. Photoelectrons from the MCP 592, which have been multiplied and accelerated, enter the semiconductor position detecting element 591 where they are further multiplied by the electron bombardment effect produced when entering the detector 591, and are then output in the form of currrent from four electrodes 593 around the detector 591 through a resistance layer of the detecting element 591. By inputting the four outputs to a position computing unit (not shown), a position signal corresponding to the incident light is obtained.

Although some typical two-dimensional photodetectors have been described above, it should be noted that photodetectors which can be used in combination with the multiple beam highly directional optical systems in the present invention are not necessarily limited to those described above and that any type of detector which can detect light in a two- or one-dimensional pattern can be employed. To apply a multiple beam highly directional optical system of the pres net invention to a two-dimensional detector of the type described above, light that has passed through the multiple beam highly directional optical system is made incident on the detector in place of the incident light to the above-described two-dimensional photodetectors. Although the conventional two-dimensional photodetectors shown in FIGS. 61 to 69 employ an optical fiber plate for the plane of incidence to light up and level out the screen, it should be noted that a multiple beam highly directional optical system of the present invention may be employed in place of the optical fiber plate, as a matter of course.

Application examples of such a highly directional optical system will be explained below.

Figure 70:
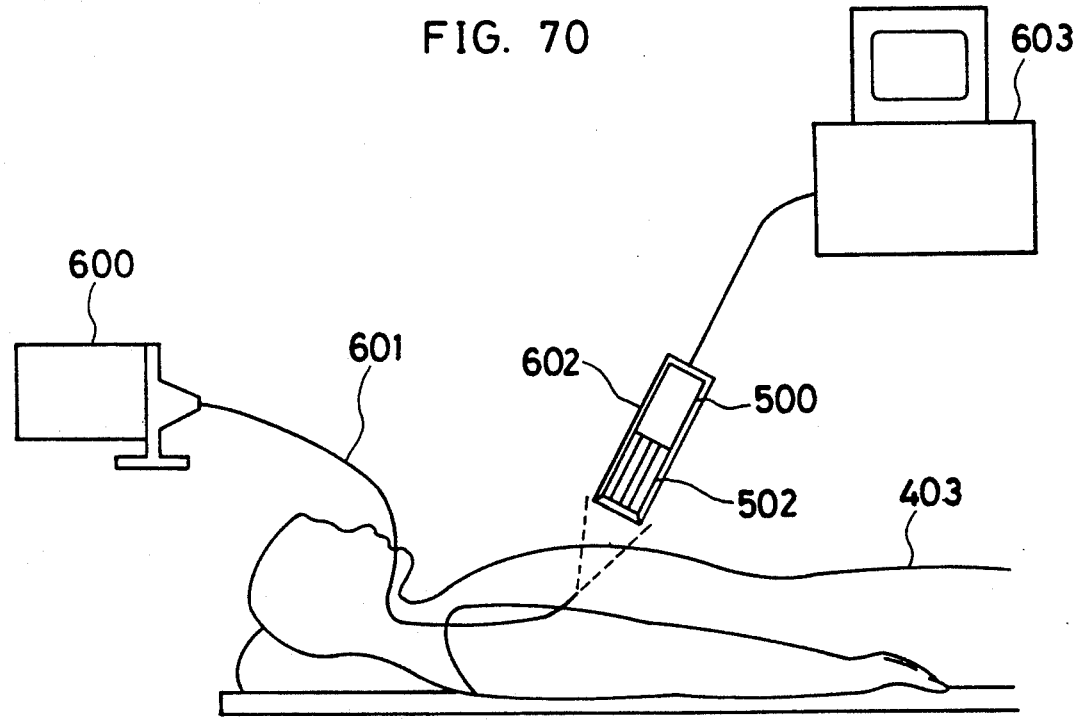
FIGS. 70 and 71 are conceptual views showing application examples in which the highly directional optical system according to the present invention is applied to biological laser sensing tomography.
Figure 71:
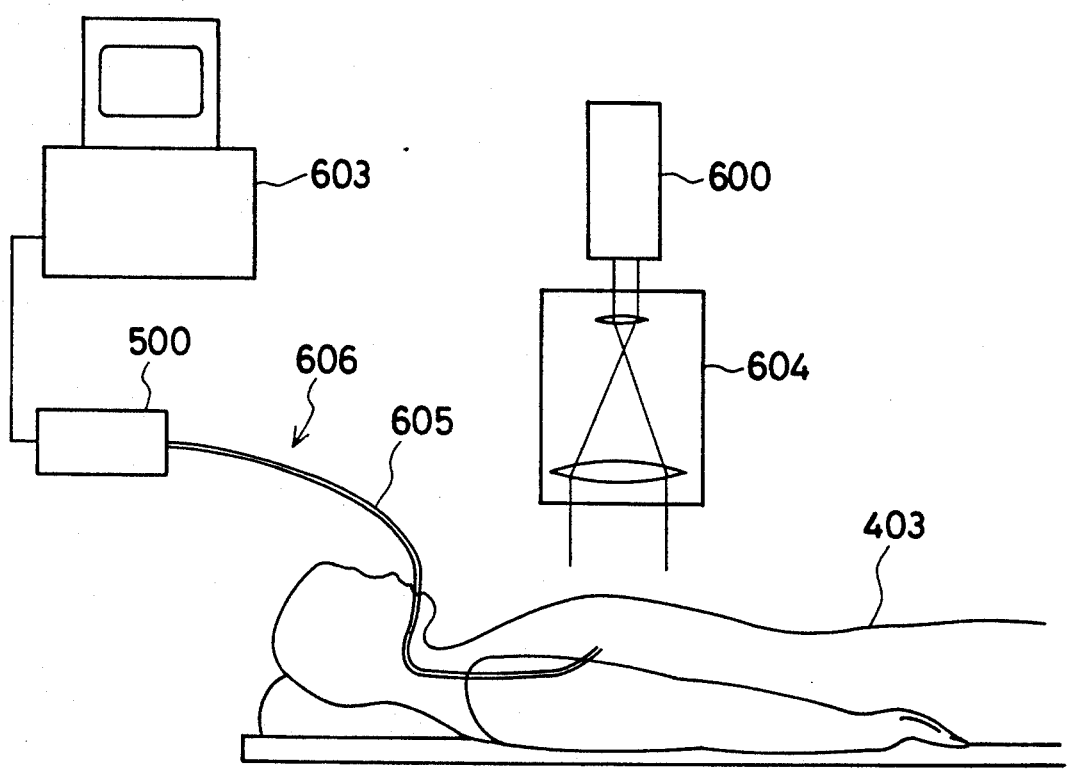

FIGS. 70 and 71 are conceptional views showing examples of the application of the highly directional optical system to biological laser sensing tomography. In the application example shown in FIG. 70, highly directional light form a laser 600 is introduced into a living body 403 through a highly directional optical element 601 such as that shown in FIG. 31, for example, to apply the highly directional light from the inside of the body 403 (although) the light is introduced from the mount in case of FIG. 70, it may be introduced from other part, for example, the anus). The light that is transmitted through the living body 403 without being absorbed or scattered is detected by a highly directional optical system 602 according to the present invention to obtain an optical sectional image of the living body 403. The image is displayed on a monitor 603, for example. In the case of FIG. 71, contrary to the arrangement shown in FIG. 70, highly directional light is applied from the outside the living body 403 and detected inside the body 403. More specifically, highly directional light from the laster 600 is expanded by a beam expander 604 and externally applied to the living body 403. Inside the body 403, a highly directional optical system 605 such as that shown in FIG. 45, for example, is inserted, the distal end of the optical system 605 being capable of being controlled from the outside of the body 403. A two-dimensional photodetector 500 is brought into close contact with the rear end of the highly directional optical system 606 such as that shown in FIG. 53. Thus, an optical sectional image of the living body 403 is obtained in vivo, and the image is displayed on the monitor 603, for example. In this case, it is also possible to employ a highly directional optical element such as that shown in FIG. 31, for example, in place of the highly directional optical system 605, and employ a single photodetector in place of the two-dimensional photodetector 500. In this way, an optical CT image of the living body 403 can be obtained by use of the highly directional optical system of the present invention.

Figure 72:
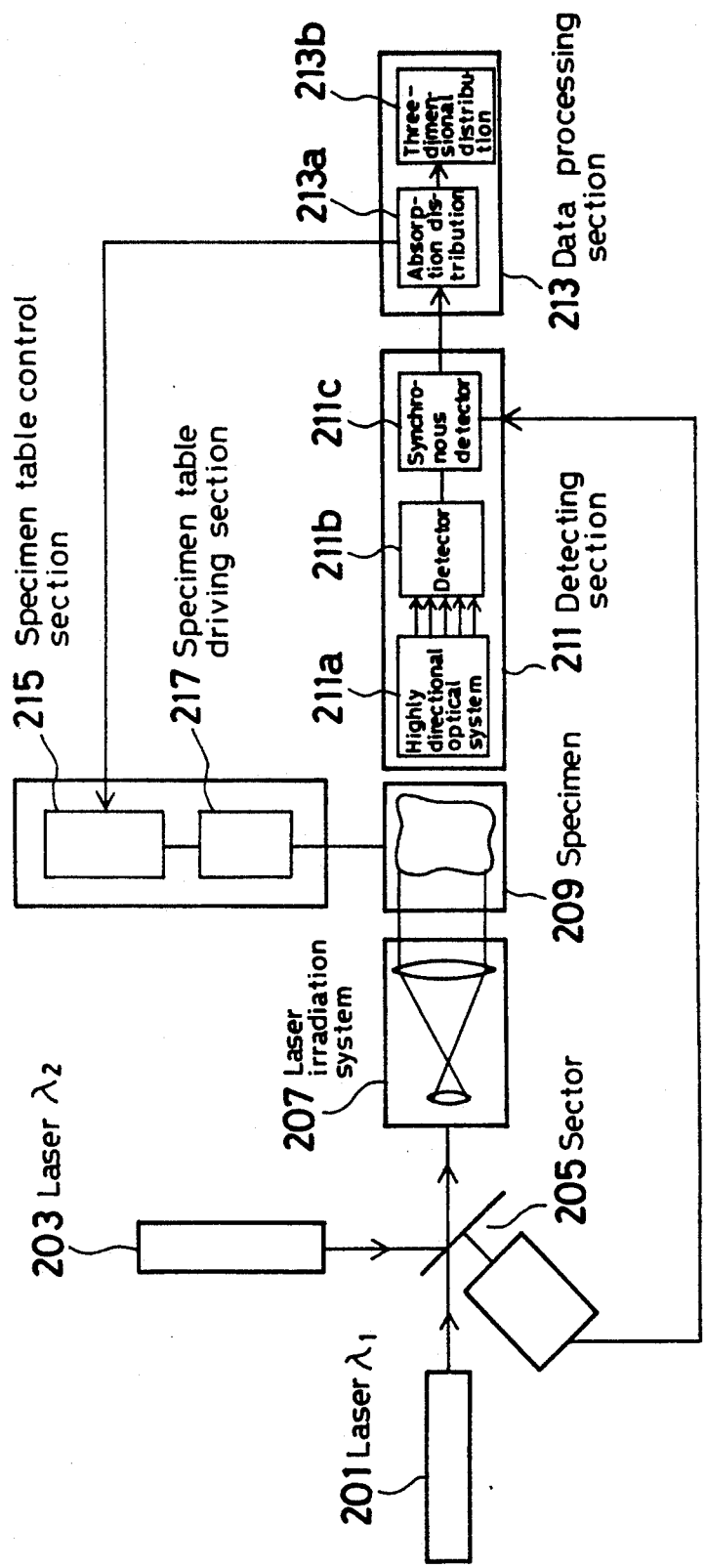
FIG. 72 shows the general arrangement of an optical sectional image forming apparatus according to the present invention.

FIG. 72 shows the general arrangement of an optical sectional image forming apparatus according to the present invention. In the figure, reference numerals 201 and 203 denote lasers, 205 a sector, 207 a laser irradiation system, 209 a specimen, 211 a detecting section, 211a a highly directional optical system, 211b a detector, 211c a synchronous detector, 213 a data processing section, 213a an absorption distribution computing section, 213b a three-dimensional distribution computing section, 215 a specimen table control section, and 217 a specimen able driving section.

Referring to FIG. 72, laser light with wavelengths $\lambda_1$ and $\lambda_2$ from the lasers 201 and 203 are alternately applied by the sector 205 to the specimen 209 through the laser irradiation system 207. The transmitted light from the specimen 209 is detected by the detector 211b through the highly directional optical system 21a of the present invention, such as that described above. The detected signal is subjected to synchronous detection in response to a driving signal for the sector 205, and an absorption distribution is measured in the data processing section 213. At the same time, the specimen 209 is rotated or moved by the data processing section 213 through the specimen table control section 215 and the specimen table driving section 217, thereby detecting transmitted light which has undergone absorption in each region of the specimen 209 and obtaining a three-dimensional absorption distribution image in the data processing section, and thus obtaining an optical sectional image. It should be noted that the transmitted light from the specimen generally contains scattering and absorption components which are mixed with each other. If the scattered light from the specimen attenuates satisfactorily in the highly directional optical system, laser of a single wavelength will suffice. In such a case, the sector 205 functions as a chopper that interrupts the laser light.

Figure 73:
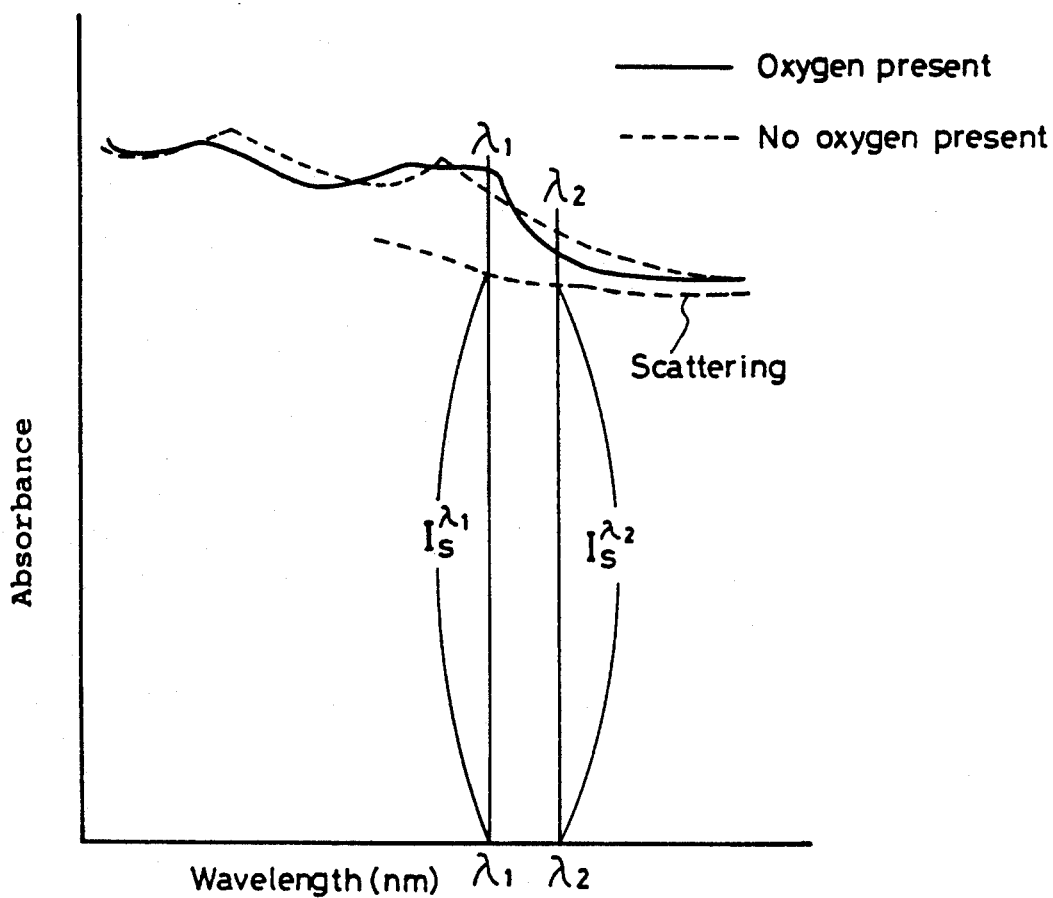
FIG. 73 is a graph showing the absorbance characteristics of oxymyoglobin and deoxymyoglobin with respect to wavelength.

FIG. 73 exemplarily shows the absorbance characteristics of oxymyoglobin and deoxymyoglobin with respect to wavelength. As will be clear from the figure, the scattering component shows a little wavelength dependence and has a wavelength region where it takes a substantially constant value. Therefore, two wavelengths $\lambda_1$ and $\lambda_2$ at which the scattering component is substantially constant are used, and the absorbances at these wavelengths are subjected to subtraction, thereby enabling removal of the scattering component. Thus, if scattered light cannot sufficiently be attenuated in the highly directional light-receiving system of the present invention, the two-wavelength method is used in combination therewith, thereby enabling the scattering component to be removed even more effectively. In addition, the two-wavelength method enables the change with time of the absorbance at a certain wavelength to be recorded by comparison with the absorbance at another wavelength. The two-wavelength method also has the advantage that the change of the absorbance with time can be detected more accurately than in the case of the single-wavelength method, by selecting a wavelength at which a particular target object shows no change of absorbance with time and a wavelength at which the object shows changes of absorbance with time.

Figure 74A:
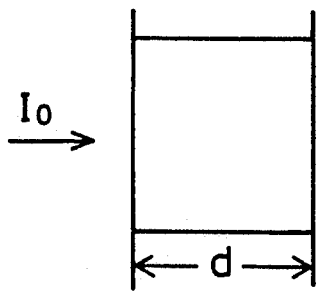
FIGS. 74(a-b) is a view for explanation of the two-wavelength method and the difference spectrum method.

In general, spectrometry for biological tissues is carried out essentially in inhomogeneous systems containing scattering particles. In such a case, Beer-Lambert law, which holds for transparent specimens, is not always valid. Measuring methods which are effectively employed for such cloudy specimens involve the two-wavelength method and the difference spectrum method. Consider a specimen which has a low concentration so that Beer-Lamber law holds, and assuming that the quantity of illuminating light is $I_0$ and the quantity of transmitted light is I, as shown in FIG. 74(a), the following relationship holds:

$$log I_0/I = \epsilon c d$$

where $\epsilon$ is extinction coefficient, c is concentration, and d is optical path length.

With regard to two different wavelengths $\lambda_1$ and $\lambda_2$, the following relationships similarly hold:

$$log I_0(\lambda_1)/I(\lambda_1) = \epsilon(\lambda_1)cd$$

$$log I_0(\lambda_2)/I(\lambda_2) = \epsilon(\lambda_2)cd$$

Hence, $$log I(\lambda_2)/I(\lambda_1) - log I_0(\lambda_2)/I_0(\lambda_1) = \epsilon(\lambda_1) - \epsilon(\lambda_2)cd$$

Figure 74B:
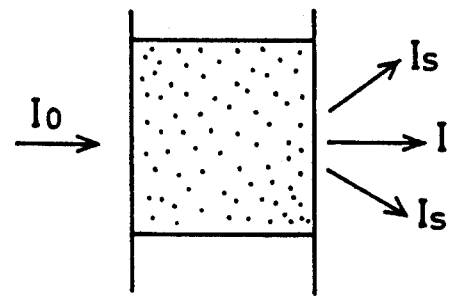

In other words, the difference in absorbance between the two wavelengths is proportional to the concentration. When light $I_0$ is made incident on a suspension specimen, as shown in FIG. 74(b), scattering and reflection components $I_s$ are generated in addition to the transmitted light. Accordingly, the following relationship holds:

$$log I_0/I = \epsilon cd + I_s$$

where $I_s$ represents attenuation by scattering. Hence, the following relationship similarly holds:

$$log I(\lambda_2)/I(\lambda_1)$$
$$= \epsilon(\lambda_1) - \epsilon(\lambda_2)cd - log I_0(\lambda_2)/I_0(\lambda_1) + (I_s(\lambda_1) - I_s(\lambda_2))$$

Accordingly, if $I_s(\lambda_1)$ is equal to $I_s(\lambda_2)$, the concentration of the specimen can be measured by obtaining an absorbance difference, with the effect of scattering eliminated. If $\lambda_1$ and $\lambda_2$ are made close to each other, it is possible to suppose that the effect of scattering and the like at each of the two wavelengths is substantially the same, and it is therefore possible to obtain the concentration of the specimen on the basis of the absorbance difference. Thus, if the highly directional optical element of the present invention and the two-wavelength method are used jointly, separation of scattered light can be attained even more effectively. Moreover, it is also possible to observe changes of the target object with time by selecting two wavelengths $\lambda_1$ and $\lambda_2$ such that at one wavelength the object shows changes of absorbance with time and at the other wavelength it shows no absorbance change with time.

Figure 75:
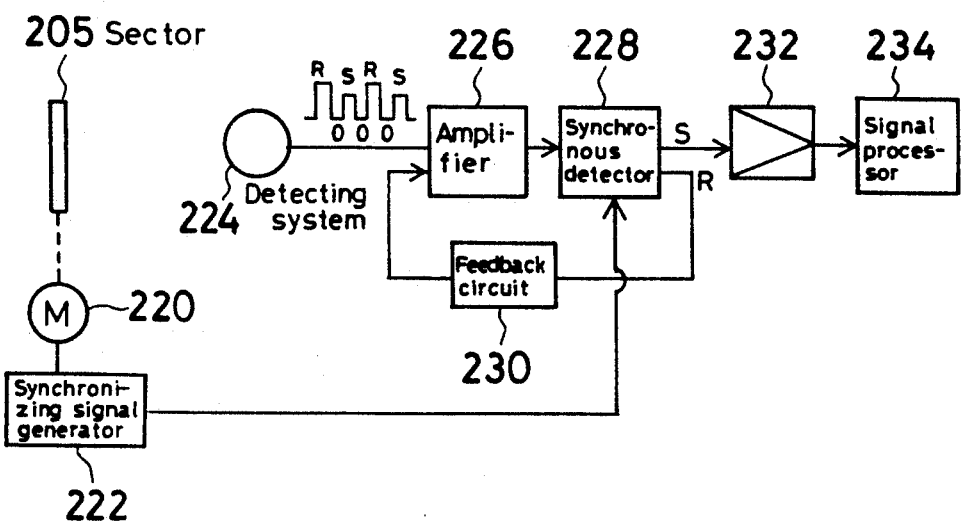
FIG. 75 is a block diagram showing automatic gain control for the two-wavelength detection method.

FIG. 75 is a block diagram showing automatic gain control for the two-wavelength detection method. In the figure, reference numeral 205 denotes a section, 220 a motor, 222 a synchronizing signal generator, 224 a detecting system, 226 an amplifier, 228 a synchronous detector, 230 a feedback circuit, 232 an amplifier, and 234 a signal processor.

Referring to FIG. 75, with the sector 205 being rotated by the motor 220, a reference signal R and a detected signal S are alternately taken out by the detecting system 224 and input to the amplifier 226. Meantime, the synchronizing signal generator 222 generates a signal synchronized with the rotation of the motor 220. With this synchronizing signal, the output of the amplifier 226 is synchronously detected to thereby separate the detected signal S and the reference signal R from each other. The separated reference signal R is negatively fed back to the input of the amplifier 226 through the feedback circuit 230 to control the gain.

In the state where the gain control is effected so that the reference signal R is constant, the signal S is taken out and this is processed in the signal processor 234, thereby obtaining information about the absorption of the specimen.

Figure 76:
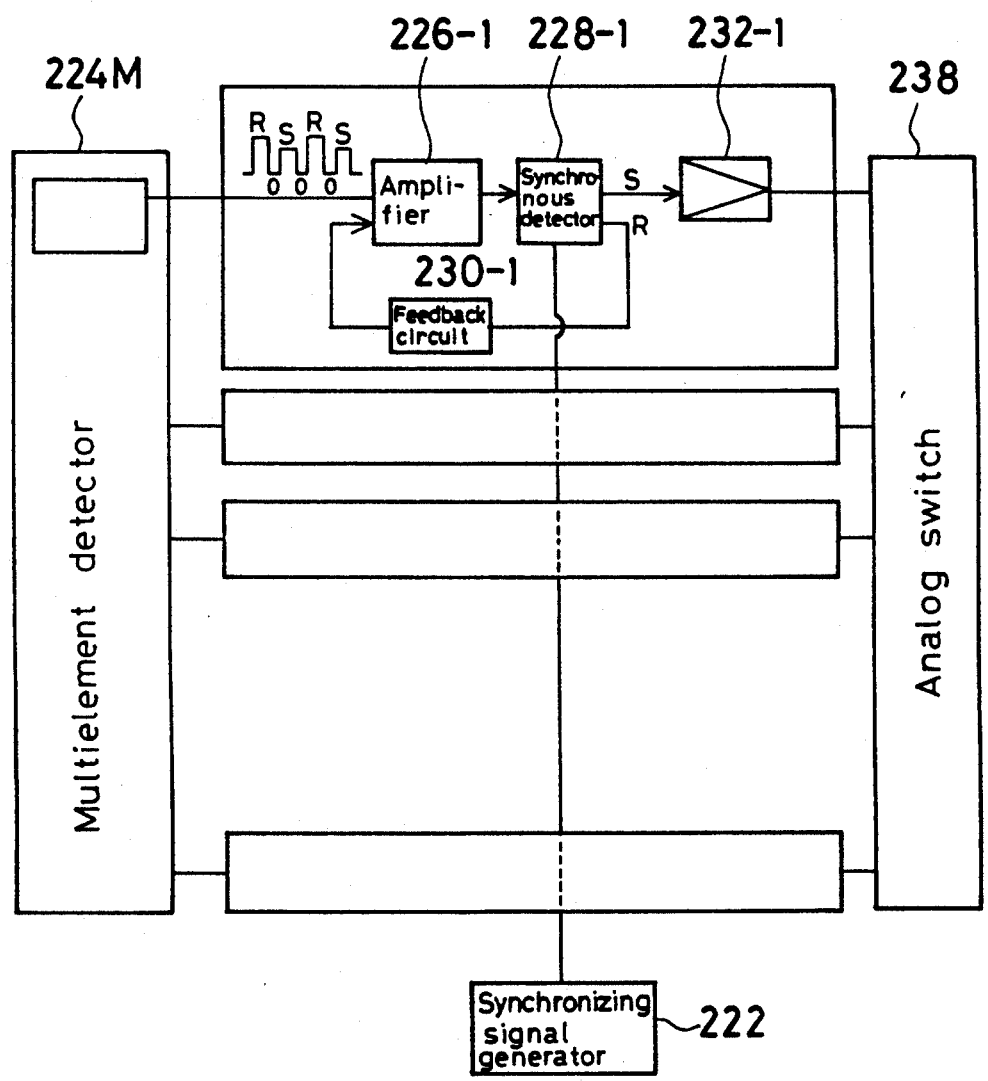
FIG. 76 is a block diagram showing an application of the automatic gain control system to a multielement detecting system.

FIG. 76 is a block diagram showing an application of the automatic gain control system shown in FIG. 75 to a multielement detecting system.

The automatic gain control system shown in FIG. 75 is provided to correspond to each detector element of a multielement detector 224M, and outputs from the control systems are taken out through an analog switch 238, thereby enabling the gain control of the signal corresponding to each detector element.

Figure 77:
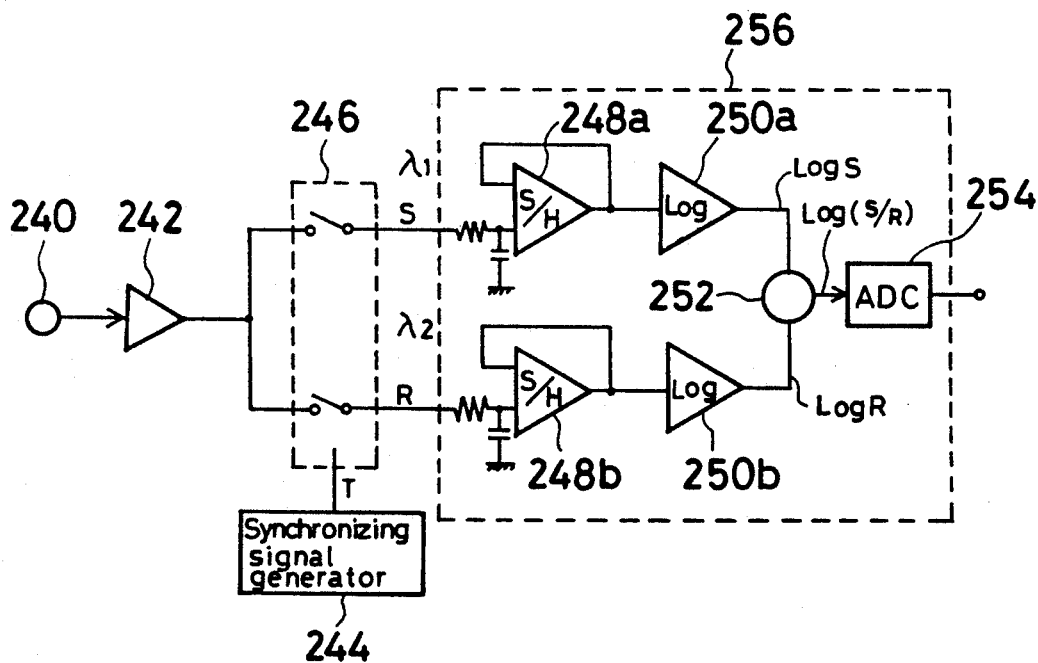
FIG. 77 is a block diagram showing an absorbance difference detecting system by a sample-and-hold method.

FIG. 77 is a block diagram showing an absorbance difference detecting system by a sample-and-hold method. In the figure, reference numeral 240 denotes a detecting system, 242 an amplifier, 244 a synchronizing signal generator, 246 a synchronous detector, 248a and 248b sample-and-hold circuits, 250a and 250b logarithmic amplifiers, 252 a synthesizer, and 254 an A/D converter.

A signal that is detected by the detecting system 240 is amplified and then separated in the synchronous detector 246 into two wavelengths, e.g., $\lambda_1$ and $\lambda_2$, which are each subjected to sample-and-hold process and then logarithmic amplification and are then subjected to subtraction in the subtracter 252, thereby obtaining a logarithmic value of an output ratio with respect to the wavelengths $\lambda_1$ and $\lambda_2$. The logarithmic value, which represents the absorbance difference, that is, the concentration of the specimen, as stated above, is converted in the A/D converter 254 into a digital quantity, which is then subjected to data processing in a computer or the like.

Figure 78:
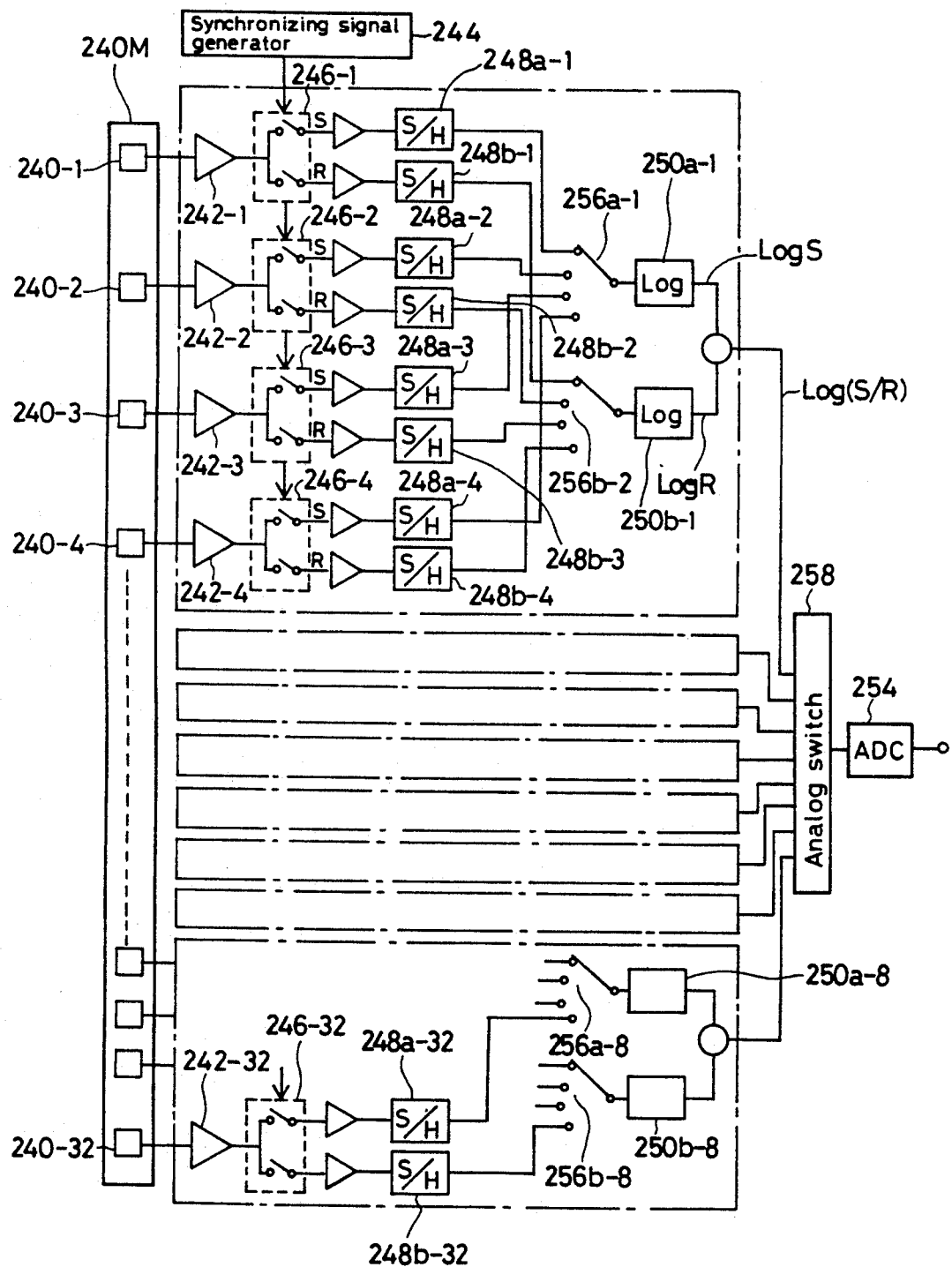
FIG. 78 is a block diagram showing an example in which the sample-and-hold method shown in FIG. 77 is applied to a multielement detecting system.

FIG. 78 is a block diagram showing an example in which the sample-and-hold method shown in FIG. 77 is applied to a multielement detecting system to detect an absorbance difference on the basis of a signal from each of a plurality of detectors.

In the arrangement shown in FIG. 78, a pair of logarithmic amplifiers and one subtracter are provided to correspond to every four detectors, which are switched over by use of changeover switches 256a and 256b so as to share the two logarithmic amplifiers, and an output that is obtained from each subtracter is taken out through an analog switch 258 and then supplied to an A/D converter 254 to obtain a digital output.

Figure 79:
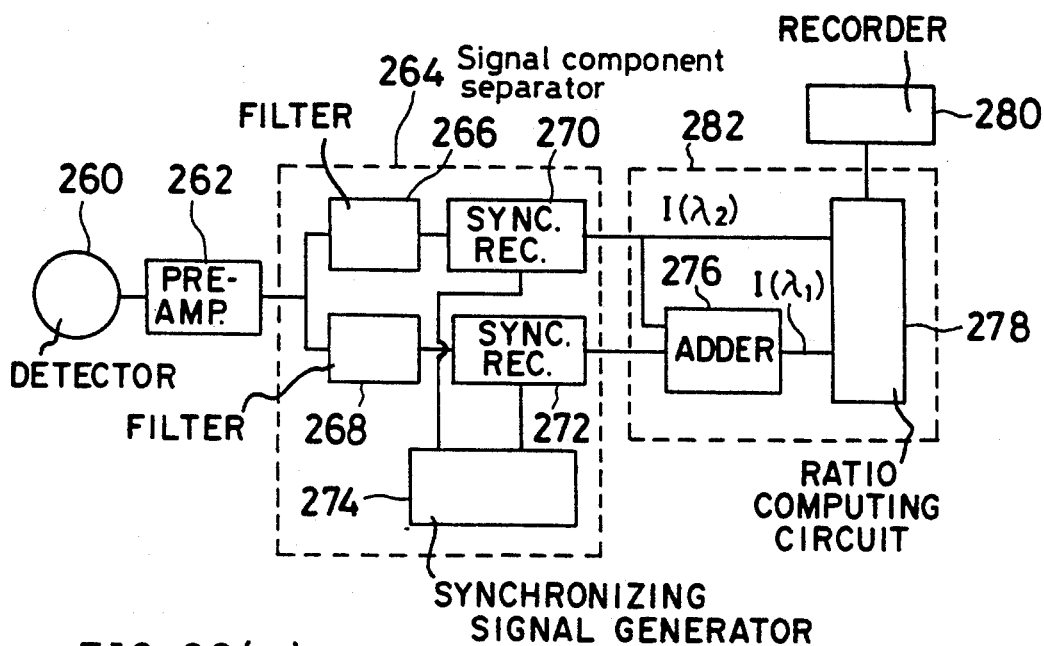
FIGS. 79 and 80(a–c) are views for explanation of an electrical system for directly detecting a ratio by detection of frequency components.

FIGS. 79 and 80 are views for explanation of an electrical system for directly detecting a ratio by detection of frequency components. In the figures, reference numeral 260 denotes a detector, 262 a pre-amplifier, 264 a signal component separator, 266 and 268 filters, 270 and 272 synchronous rectifiers, 274 a synchronizing signal generator, 276 an adder, 278 a ratio computing circuit, 280 a recorder, 282 an arithmetic circuit, and 284 a sector.

Figure 80A:
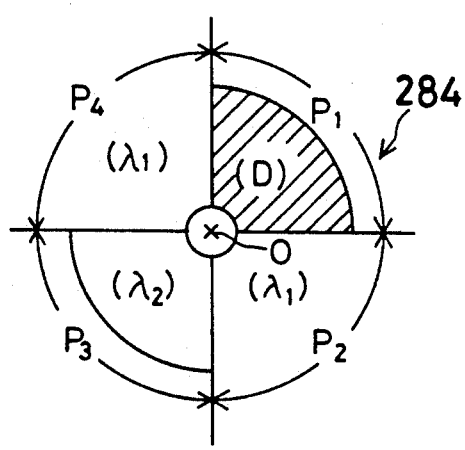
Figure 80B:
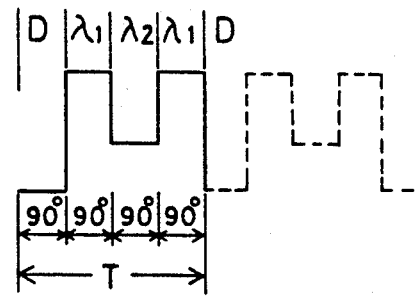

In this system the sector 284 is divided into four regions, as shown in FIG. 80(a), i.e., a region $P_1$, which is a dark region that passes no signal, regions $P_2$ and $P_4$, which pass a signal of wavelength $\lambda_1$, and a region $P_3$, which passes a signal of wavelength $\lambda_2$. By rotating the sector 284, a signal with the sequence of D, $\lambda_1$, $\lambda_2$, D . . . is taken out, as shown in FIG. 80(b).

Figure 80C:
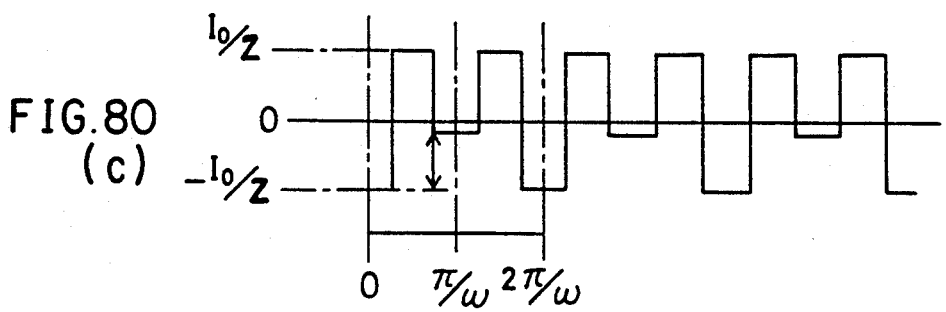

This signal can be detected by blocking the DC component as being an AC signal in which the frequency of the signal of $\lambda_1$ is defined as f and the frequency of the signal of $\lambda_2$ is defined as 2f. More specifically, a signal such as that shown in FIG. 80(c) is detected by the detector 260 shown in FIG. 79, amplified in the pre-amplifier 262 and then filtered in the filters 266 and 268 which pass signals of frequencies f and 2f, respectively, thereby extracting signals of $\lambda_1$ and $\lambda_2$. These signals are subjected to synchronous detection in the synchronous rectifiers 270 and 272, thereby extracting signals corresponding to the wavelengths $\lambda_1$ and $\lambda_2$.

Incidentally, the signal of wavelength $\lambda_2$, that is, frequency 2f, has the signal of frequency f, that is, $\lambda_1$, superposed thereon; therefore, the component of wavelength $\lambda_1$ is removed by subtraction in the adder 276, thereby enabling signals $I(\lambda_1)$ and $I(\lambda_2)$ to be separatively taken out. Then, the ratio of these signals is computed in the ratio computing circuit 278, thereby taking out a signal corresponding to the absorbance difference, which is then recorded by the recorder 280.

Thus, signals of two wavelengths are arranged as signals of frequencies f and 2f, and these frequency components are detected. By so doing, an absorbance difference can be detected as a signal which is independent of noise.

Figure 81:
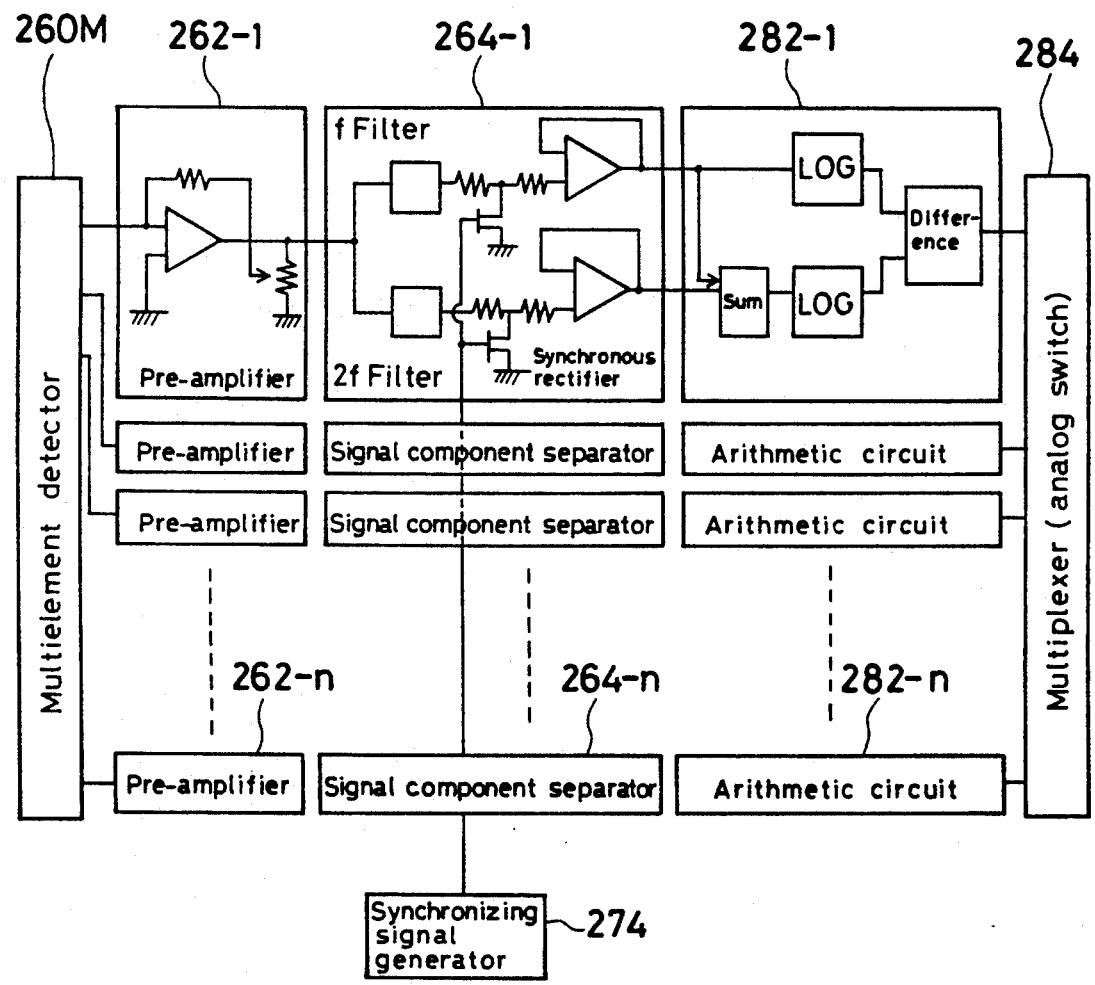
FIG. 81 is a block diagram showing an example in which the detecting system shown in FIG. 79 is applied to a multielement detecting system.

FIG. 81 is a block diagram showing an example in which the detecting system shown in FIG. 79 is applied to a multielement detecting system. In the illustrated example, a number of pre-amplifiers, signal component separators and arithmetic circuits, which corresponds to the number of detector elements that constitute a multielement detector 260M, are connected to the detector elements, respectively, and sequentially switched over by a multiplexer 284 to take out signals.

The above examples apply in cases where the detected light intensity is relatively strong and a continuous output can be obtained. The following is a description of an extremely feeble light measuring method.

FIGS. 82 and 83 are views for explanation of an extremely feeble light measuring method. In FIG. 82, reference numeral 290 denotes a laser light source, 292 a chopper, 294 a photomultiplier (PM), 296 a pulse amplifier, 298 a pulse-height discriminator, 300 a gate, 302 a phase shifter, 304 a gate output generator, 306 an add-subtract counter, and 308 a recorder.

When light is detected by a PM, if the intensity of the light to be detected is strong, the output of the PM is continuous, and the incident light intensity can be measured from the DC component of the output. However, when the incident light intensity is extremely weak, the output of the PM is discrete, resulting in a discontinuous pulse output. In such a case, by counting these output pulses, extremely feeble incident light such as one consisting of a series of photons can be measured. However, when such extremely feeble light is to be measured, the background is inevitably detected because the PM itself emits noise pulses and it is therefore necessary to remove the background. For this reason, in the arrangement shown in FIG. 82, the signal light and the background are switched over from one to the other by a chopper, and outputs that are detected during the respective periods are subjected to subtraction by an add-subtract counter to remove the background, thereby measuring extremely feeble incident light.

Referring to FIG. 82, extremely feeble incident light is detected by the PM 294 through the chopper 292. At this time, with the switching frequency $f_0$ of the chopper 292 used as a reference signal, the add-subtract counter 306 is driven through the phase shifter 302 and the gate signal generator 304. The output of the PM 294 is amplified in the amplifier 296 and then supplied to the pulse-height discriminator 298, thereby adding a signal which exceeds a predetermined size, that is, a pulse output, to the add-subtract counter 306 through the gate 300. In the counter 306, the signal chopped by the chopper 292 and the background detecting output are subjected to addition and subtraction.

It is assumed that when the chopper 292 is open, an output of the sum total of the signal S and the noise N is obtained, whereas, when the chopper 292 is closed, the background noise N is obtained, as shown in FIG. 83(a). In synchronism with the chopper 292, the gate 300 controls the add-subtract counter 306 in such a way that when the chopper 292 is open, addition is performed, whereas, when the chopper 292 is closed, subtraction is conducted, as shown in FIGS. 83(b) and 83(c). Thus, since noise appears constantly over the whole period, the noise is removed from the output of the add-subtract counter 306 and only the signal S can be detected.

FIGS. 84 to 87 show one embodiment of a detector according to the present invention. In the figures, reference numeral 311 denotes a light-receiving element, 312 a reset FET, 313 a read FET, 314 a resistor, 315 a differential amplifier, 316 a zener diode, 317 a resistance element, 318 an operation amplifier, and 319 a low-pass filter.

The light-receiving element 311 comprises a semiconductor detecting element which is made, for example, of Si, Ge, In, GaAs, InGaAsP, etc., and which has a high internal impedance and extremely small dark current. The FETs 313 and 314 are cooled with liquid nitrogen and the light-receiving element 311 is also cooled with liquid nitrogen or liquid helium to achieve a reduction in the noise.

Figure 84:
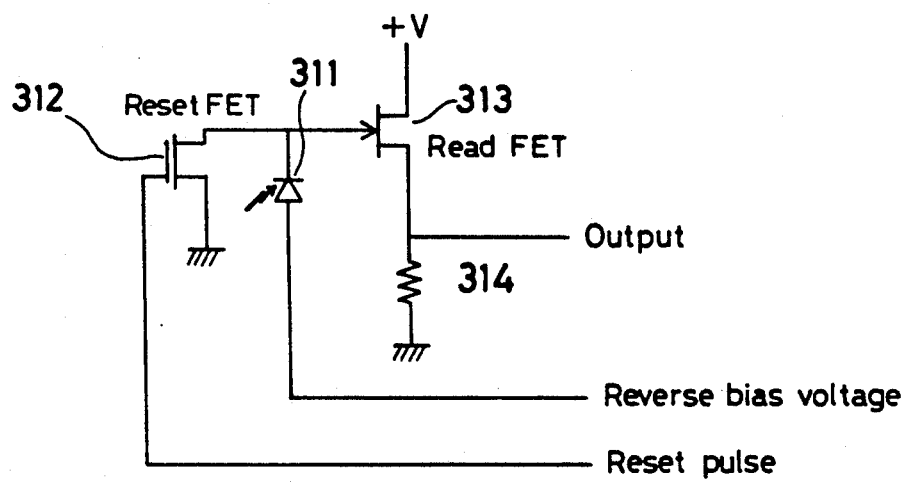
FIG. 84 shows the basic arrangement of a detector used in the present invention.

Referring to FIG. 84, the light-receiving element 311 comprises a photodiode which has a high internal impedance and extremely small dark current, and it has a reverse bias voltage applied thereto to be normally in an "off" state. The cathode terminal of the light-receiving element 311 is connected to the drain of the reset FET 312 and to the gate of the read FET 313.

Figure 85A:
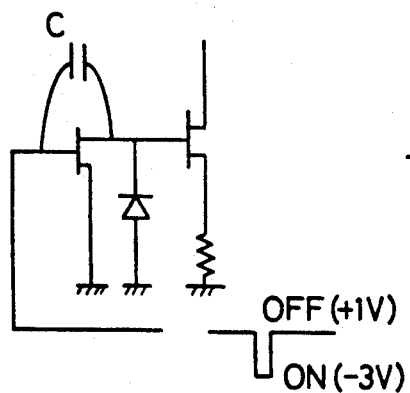
FIGS. 85(a–c) and 86 are views for explanation of the detection principle.
Figure 85B:
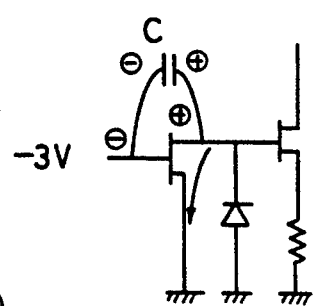

As shown in FIG. 85(a), +1 V and −3 V are alternatively applied to the gate of the FET 312 so that when +1 V is applied thereto, the FET 312 turns off, whereas, when −3 V is applied thereto, it turns on. A virtual capacitance C is present in between the gate and drain of the FET 312, so that when an "on" pulse (−3 V) is input, as shown in FIG. 85(b), a positive charge is accumulated in the capacitance C, causing the drain and source to conduct to each other. As a result, the charge stored in the stray capacitance of the light-receiving element 311 flows toward the ground.

Figure 85C:
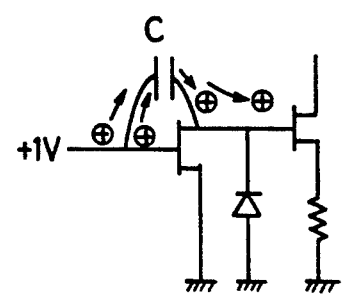
Figure 86:
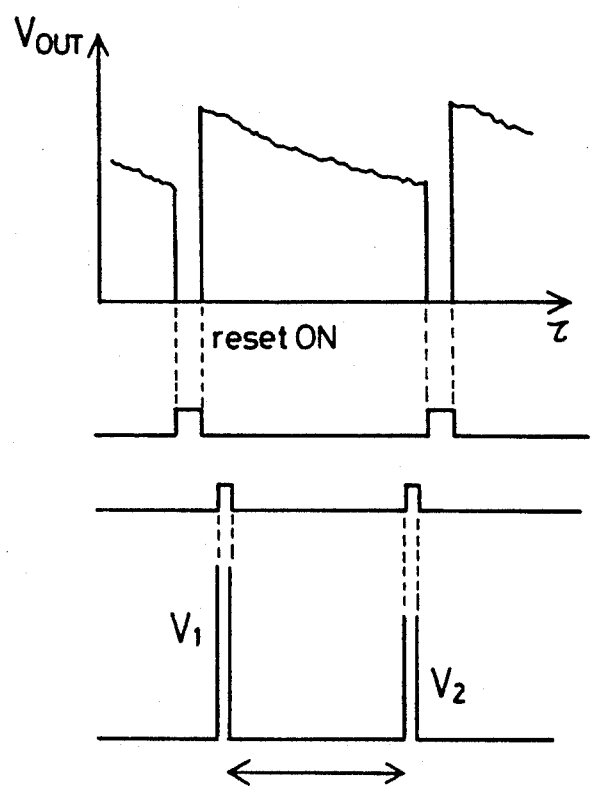

When an "off" pulse (+1 V) is input, as shown in FIG. 85(c), a positive voltage is applied to the capacitance C, and the positive charge stored therein is therefore discharged. As a result, the conduction between the drain and source is canceled and the FET 312 turns off. In the detector of the present invention, no load resistance is connected to the light-receiving element 311; therefore, Johnson noise is determined only by the internal resistance of the detector. In addition, since charge is accumulated unless a reset pulse is applied, the time for accumulation can be lengthened and it is therefore possible to realize detection of high sensitivity.

Referring to FIG. 84, when the FET 313 is operated as a source follower to read a signal, the output $V_{OUT}$ changes as shown in FIG. 86(a). At the first and last timings of the "on" period, sampling is made in response to samping pulses (FIG. 86(b)) to detect outputs $V_1$ and $V_2$ (FIG. 86(c)), and the received light quantity is obtained on the basis of the difference between $V_1$ and $V_2$.

Figure 87:
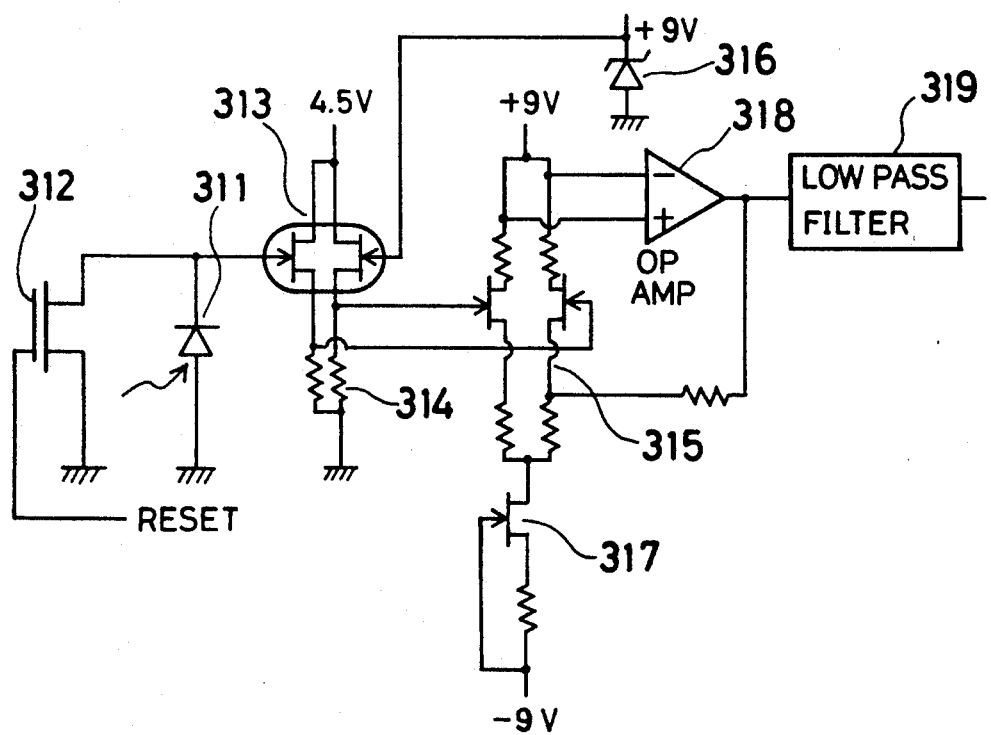
FIG. 87 is a diagram exemplarily showing a detection circuit.

FIG. 87 is a diagram exemplarily showing an actural circuit of the detector of the present invention shown in FIG. 84. A signal that is read by the source follower 313, which is supplied at one input terminal with a constant voltage from the zener diode 316 and at the other input terminal with the voltage accumulated in the light-receiving element 311, is amplified in the differential amplifier 315 and the operational amplifier 318 to detect a signal of a predetermined band in the low-pass filter 319.

Figure 88:
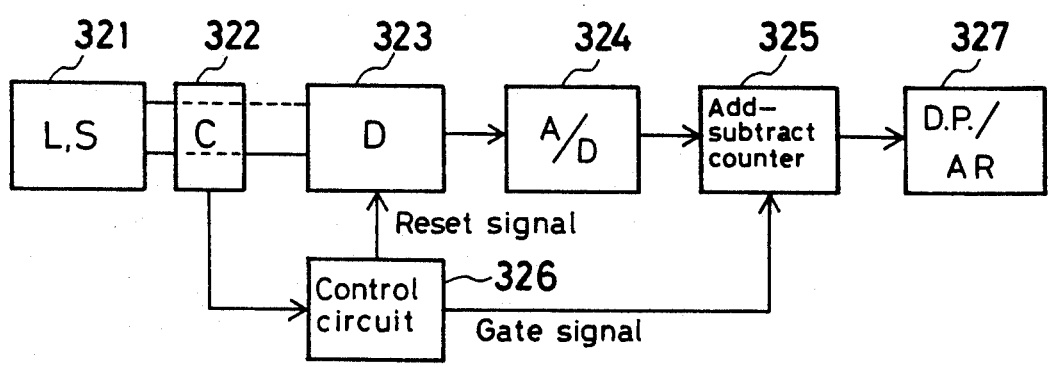
FIG. 88 is a block diagram showing the arrangement of detector designed to diminish noise by a chopper method.
Figure 89:
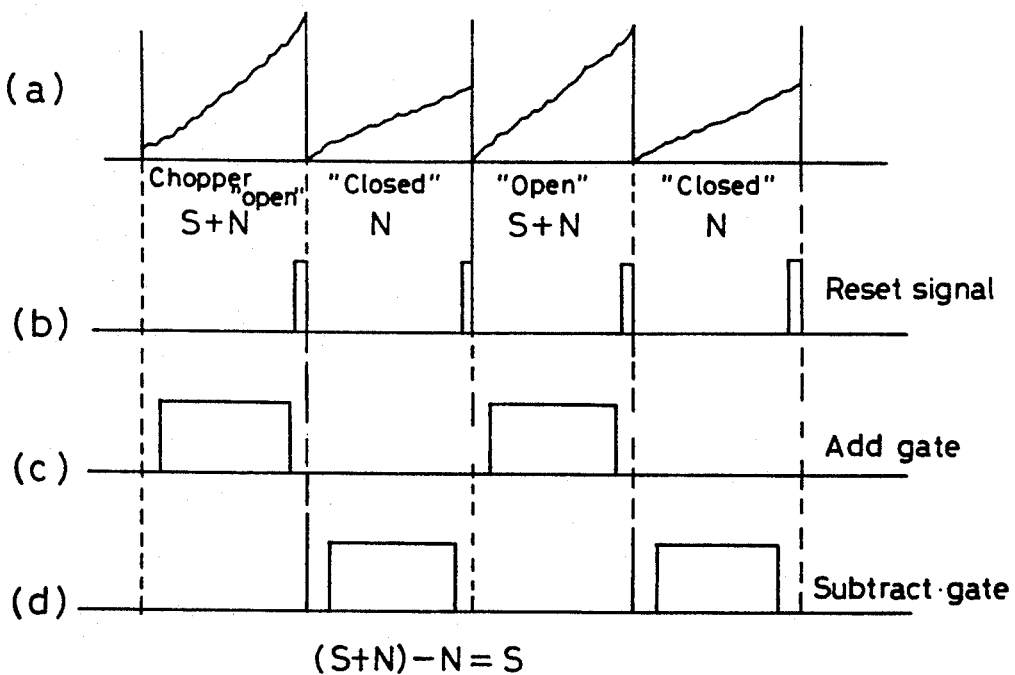
FIGS. 89(a–d) are waveform charts.

FIG. 88 is a block diagram showing one embodiment a detecting apparatus that employs the detector shown in FIG. 84, and FIG. 89 is a waveform chart thereof.

Referring to these figures, extremely feeble incident light from a light source 321 is detected by a detector 323 of the present invention through a chopper 322. At this time, a control circuit 326 outputs a reset signal to reset the detector 323 in synchronism with a switching signal for the chopper 322. At the same time, an add-subtract counter 325 is controlled in response to a gate control signal that is output from the control circuit 326 in synchronism with the switching signal for the chopper 322 such that when the light source 321 is on, the detected and A/D converted signal and the dark current are added together, whereas, when the light source 321 is off, the dark current is subtracted from the sum, and the result is output to a digital printer/analog recorder 327.

It is assumed that when the chopper 322 is open, an output representative of the sum total of the signal S and the noise N is obtained, whereas, when the chopper 322 is closed, the background noise N is obtained, as shown in FIG. 89(a). The signal S+N and the signal N are each integrated over the application period of the reset signal shown in FIG. 89(b), and the add-subtract counter 325 is controlled such that when the chopper 322 is open, the signals S and N are added together in response to an add gate signal, as shown in FIG. 89(c), whereas, when the chopper 322 is closed, the signal N is subtracted from the sum S+N in response to a subtract gate signal, as shown in FIG. 89(d). As a result, since noise appears constantly over the whole period, the noise is removed and only the signal S can be detected from the output of the add-subtract counter 325.

Figure 90:
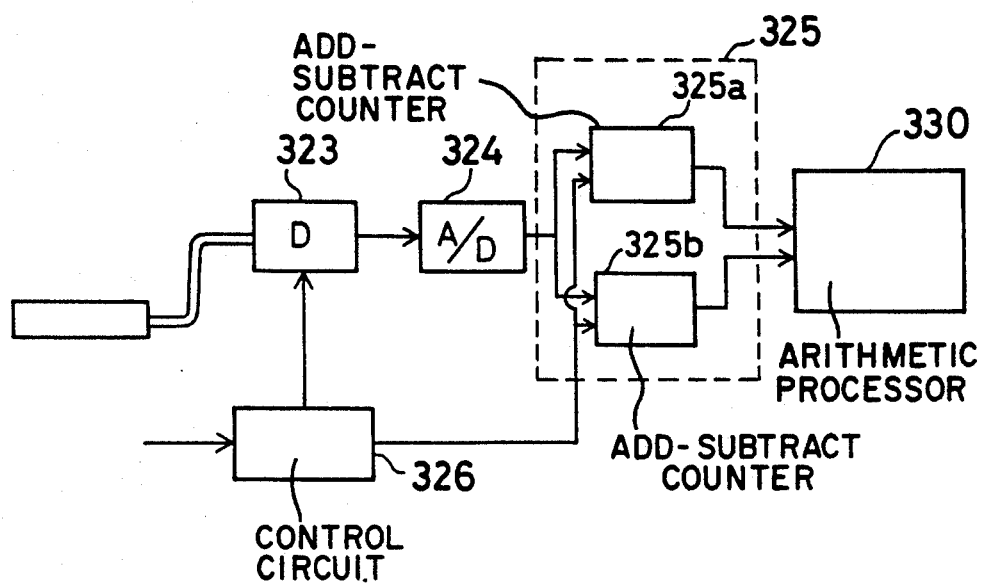
FIGS. 90 and 91(a–e) illustrate an example in which the detection method shown in FIG. 82 is applied to the two-wavelength detection method.
Figure 91:
Figure 91:
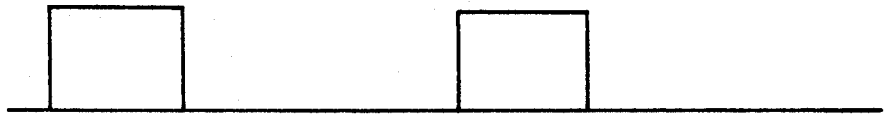
Figure 91:
Figure 91:
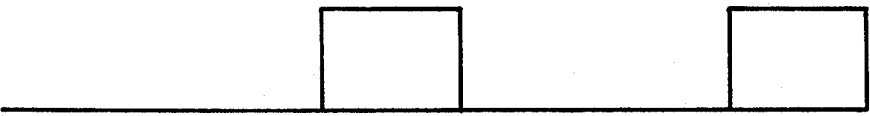
Figure 91:
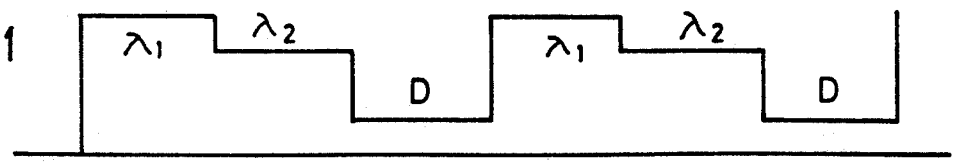

FIGS. 90 and 91 illustrate an example in which the detection method shown in FIG. 88 is applied to the two-wavelength detection method. In FIG. 90, the same reference numerals as those in FIG. 88 denote the same contents, and counters 325a and 325b constitute add-subtract circuits for wavelengths $\lambda_1$ and $\lambda_2$, respectively.

A reset signal that is shown in FIG. 91(a) and gate signals, shown in FIGS. 91(b), 91(c) and 91(d), which have a gate interval defined by the reset period, are output from the control circuit 326 synchronously with the chopper signal to reset the detector 323 periodically and control the add-subtract counters 325a and 325b. During the period of the gate signal shown in FIG. 91(b), signals of wavelength $\lambda_1$ are added together in the add-subtract counter 325a; during the period of the gate signal shown in FIG. 91(c), signals of wavelength $\lambda_2$ are added together in the add-subtract counter 325b; and during the period of the gate signal shown in FIG. 91(d), the background signal is subtracted from the sum in each of the add-subtract counters 325a and 325b. As a result, signal outputs for the wavelengths $\lambda_1$ and $\lambda_2$ are obtained from the add-subtract counters 325a and 325b, respectively, and a ratio of these signals is computed in the arithmetic processor 330, thereby detecting an absorbance difference.

Figure 92:
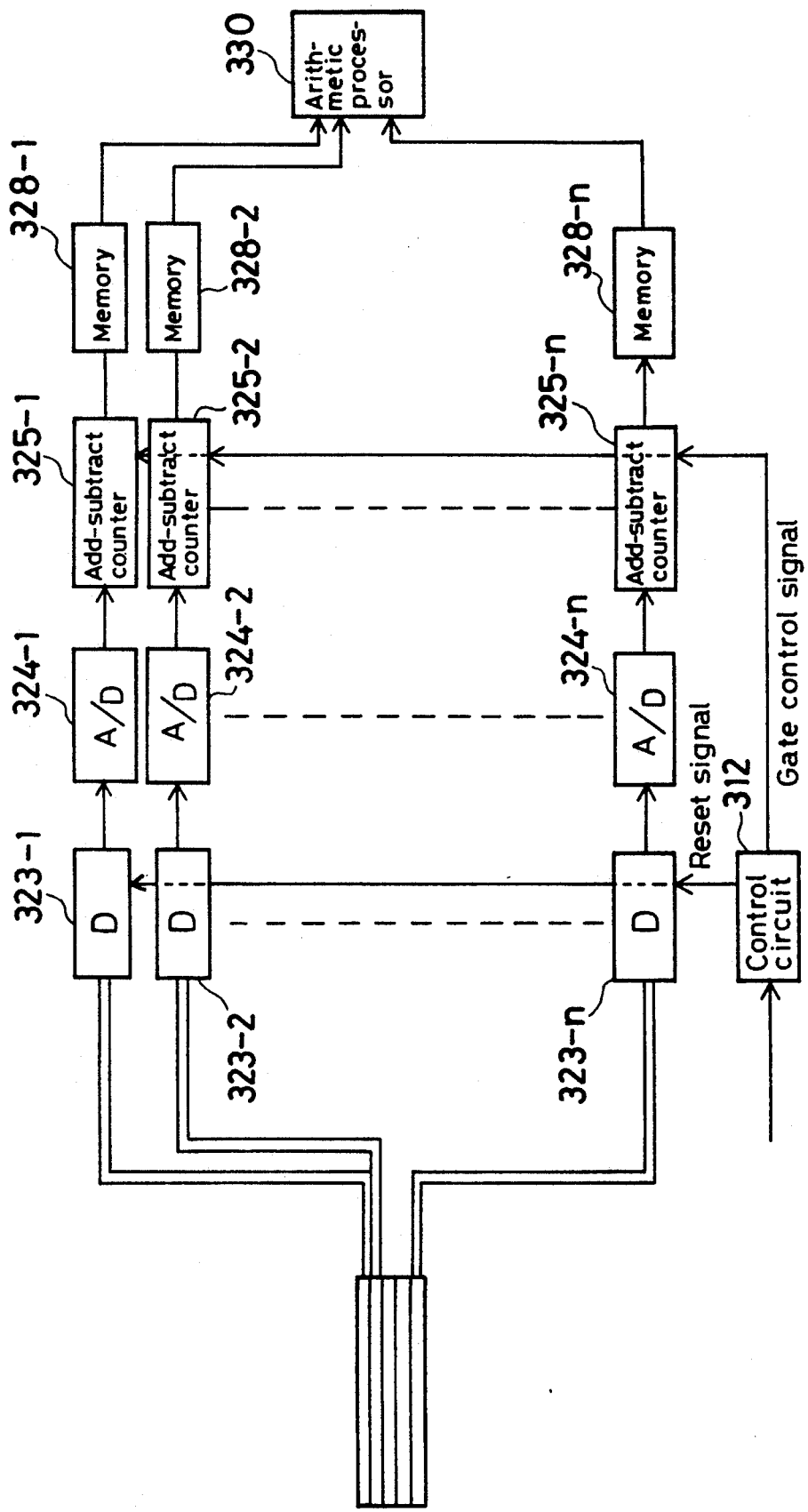
FIG. 92 shows an example in which the method shown in FIG. 88 is applied to a multielement detecting system.

FIG. 92 shows an example in which the method shown in FIG. 88 is applied to a multielement detecting system. In this arrangement, the outputs of add-subtract counters 325-1 to 325-n are stored in respective memories 328-1 to 328-n and these outputs are sequentially fetched into the arithmetic processor 330 to compute a ratio of two wavelengths, thereby enabling measurement of a difference between the absorbances obtained by the detectors.

Figure 93:
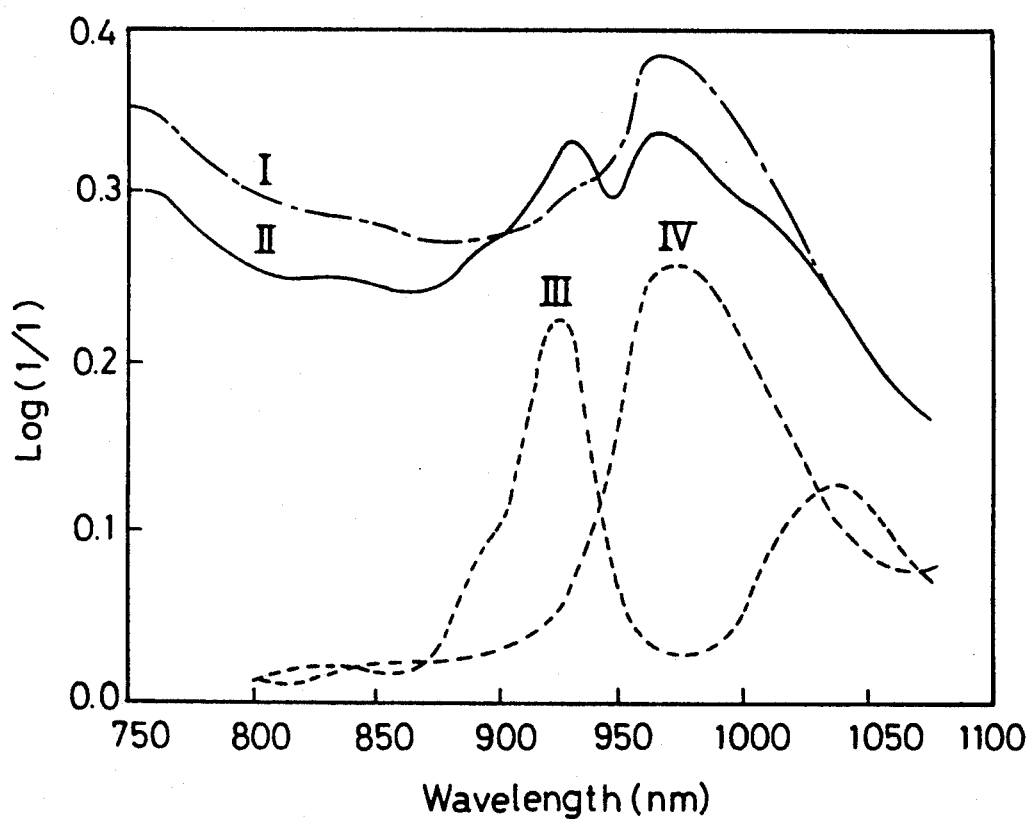
FIG. 93 shows near infrared absorption spectra of the upper arms.

FIG. 93 is a graph showing near infrared absorption spectra of the upper arms, in which I shows the near infrared absorption spectrum of the upper arm of a man with less fat; II shows that of the upper arm of a woman with much fat; III shows that of fat only; and IV shows that of water.

In the spectrum of the upper arm of the woman with much fat are clearly discerned a peak of absorption at 970 nm due to water and a peak of absorption at 930 nm due to fat. On the other hand, in the spectrum of the upper arm of the man with less fat, the absorption at 930 nm is discerned only as a small shoulder. From such a spectrum difference, a relative fat content can be computed, and the value thus obtained shows a good correlation with the one that is obtained by actual analysis.

Incidentally, the supply of oxygen is the most essential factor for a living body to function normally. For example, myocardial infarction, cerebral thrombosis or the like is necrosis of some or all of the cells in a tissue, caused by interference with the oxygen supply to the tissue as a result of interruption of its blood supply due to a blood vessel being partially clogged. In the measurement of the oxygen concentration in a biological tissue, optical biometry was first applied historically, and up to now, the most successful results have been obtained thereby. In short, optical biometry is none other than biologically following the absorbances and fluorescence intensities of four chromoproteins (chromophores), that is, cytochrome oxidase, myoglobin (Mb), hemoglobin (Hb), and pyridine nucleotide (NADH).

The absorbances and fluorescence intensities of four chromoproteins, i.e., cytochrome oxidase, myoglobin (Mb), hemoglobin (Hb), and pyridine nucleotide (NADH), will be roughly explained below.

Figure 94A:
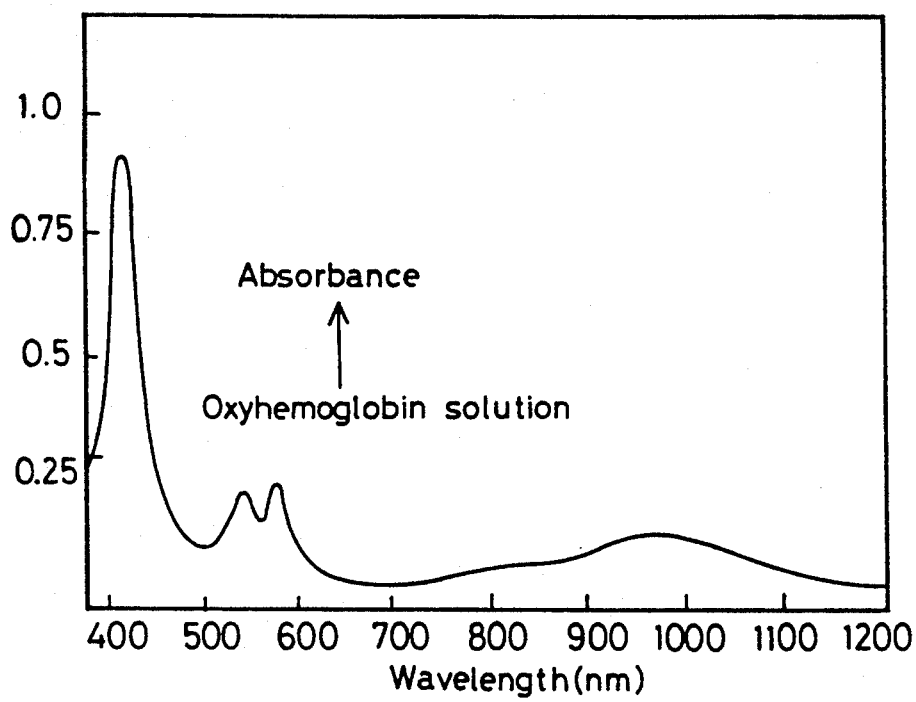
FIG. 94(a) shows a visible and near infrared absorption spectrum of an oxyhemogrobin solution.

FIG. 94(a) shows a visible and near infrared absorption spectrum of an oxyhemoglobin solution.

The most familiar "spectroscopic oxygen concentration indicator substance" is the blood. The arterial blood (containing sufficient oxygen) looks bright red, whereas, the venous blood, which contains little oxygen, looks dark red. This reflects the fact that there is a difference in color between Hb, which is contained in the red blood cells, when combining with oxygen and Hb when combining with no oxygen. The spectrum of an oxyhemoglobin solution is such as that shown in FIG. 94(a). If this is detected by use of the highly directional optical system according to the present invention and the color change (absorption change) is followed optically, the oxygen concentration in the blood can be known.

Figure 94B:
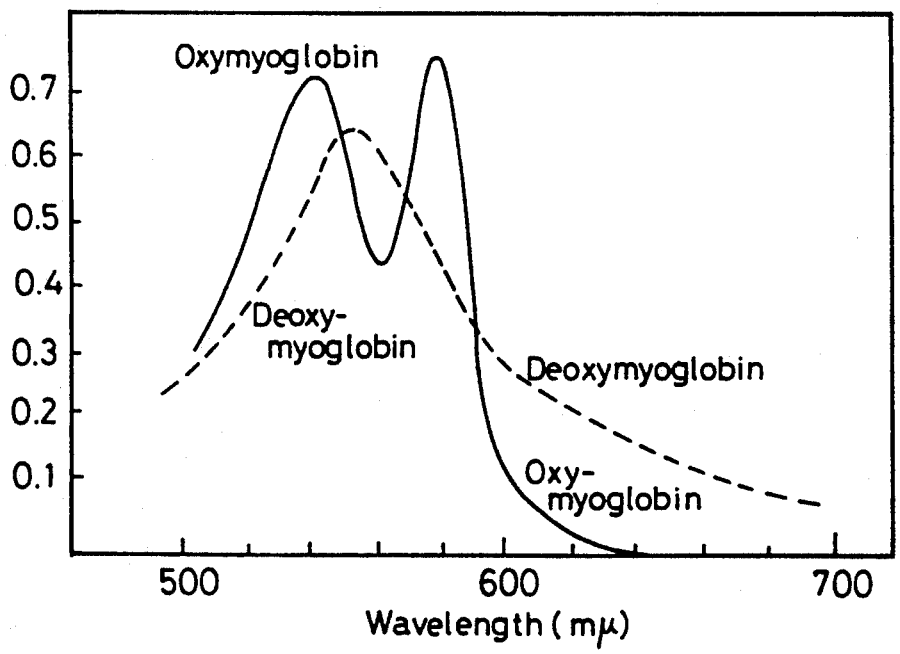
FIG. 94(b) shows an absorption spectrum of myoglobin in the visible region.

FIG. 94(b) shows an absorption spectrum of myoglobin in the visible region.

Myoglobin is mainly present in the muscle tissues of the mammals in large amounts and has iron porphyrin in the same way as hemoglobin in the blood. The reason why fresh pork and beef look bright red is due to the color of this protein. Since this protein is contained in an amount which is about 5 to 10 times that of the above-described cytochrome, when the muscle is illuminated with light, the myoglobin absorbs light in the greater part of the visible region.

When the muscle begins to contract, myoglobin first shifts from a state (oxymyoglobin) where it is combined with oxygen to a state (deoxymyoglobin) where it is not combined with oxygen. In this case, the longer the time that the muscle is contracted, the higher the degree of deoxygenation occurring. At this time, the blood flows normally through the muscle. When the muscle is contracted with the blood flow stopped (i.e., with the artery bound), the speed of deoxygenation of myoglobin increases. Even when the contraction of the muscle is canceled, the deoxygenated myoglobin is not restored to the previous state because there is no oxygen supply from the blood. This reveals that when we suddenly use strength or do exercise, the consumption of oxygen in the muscle increases, so that the oxygen supply from the blood vessel becomes short, resulting in a shortage of oxygen in the cells. When similar measurement is actually conducted with respect to the human arm, it is found that the behavior of the muscle on exertion greatly differs depending upon the age and according to whether or not the training has been made. Accordingly, detailed behavior of the muscle can be known by measuring the light absorption with the highly directional optical system of the present invention.

Figure 95A:
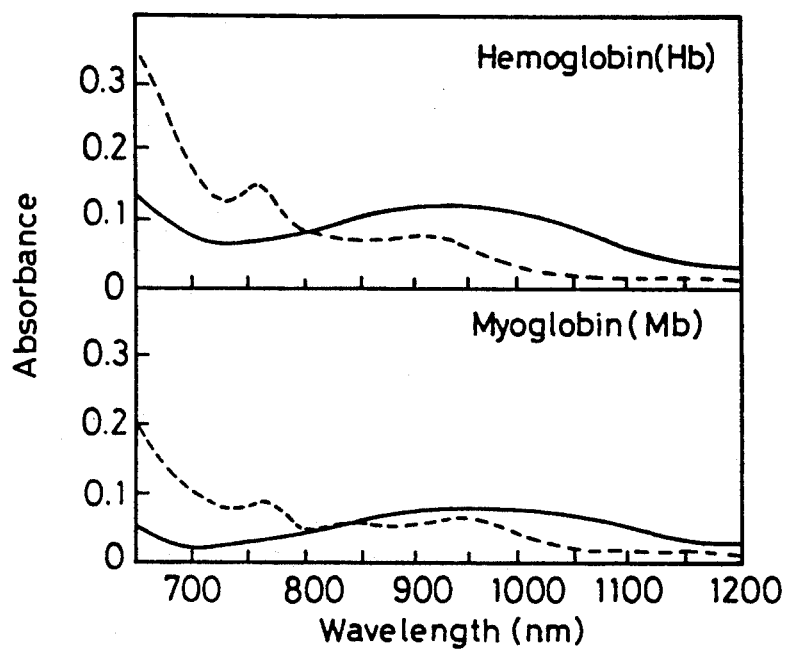
FIGS. 95(a–b) show the near infrared absorption spectra and absorbance differences of Hb and Mb.
Figure 95B:
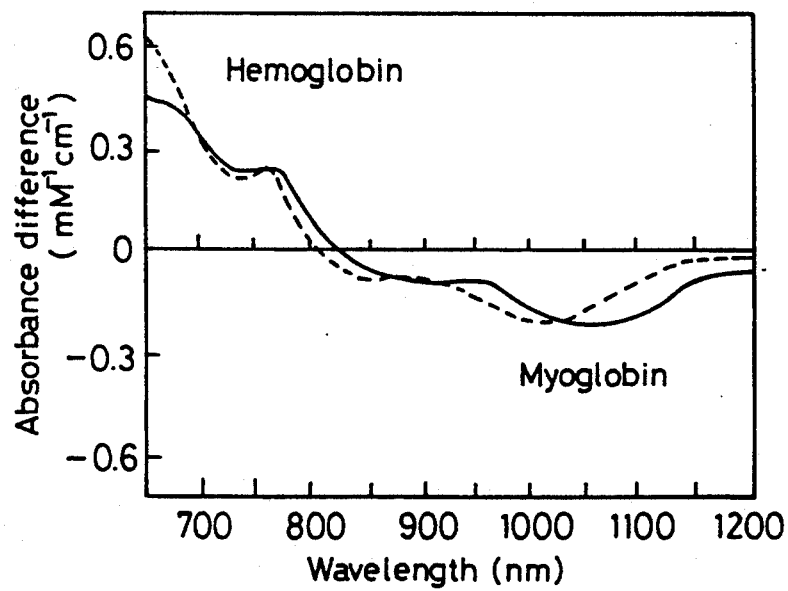

FIG. 95 shows the absorption spectra and absorbance differences of Hb and Mb in a region (near infrared region) of 700 to 1200 nm. In FIG. 95(a), the solid lines represent oxyhemoglobin and oxymyoglobin, while the chain lines represent deoxymyoglobin and deoxymyoglobin.

There is substantially no absorbance difference between Hb and Mb. Oxygenated Hb has an absorption peak at 930 nm. This absorption intensity is less than 1/40 of the absorption at 578 nm in the visible region. Deoxygenated Hb has absorption peaks at 760 nm and 905 nm. The isosbestic point in oxygenation and deoxygenation is at 805 nm, and since the absorption intensity at this wavelength is independent of the oxygen saturation, it can be employed to measure the total hemoglobin quantity. Accordingly, by obtaining these absorption spectra by use of the highly directional optical system of the present invention, the total hemoglobin quantity or the like can be obtained accurately.

Figure 96:
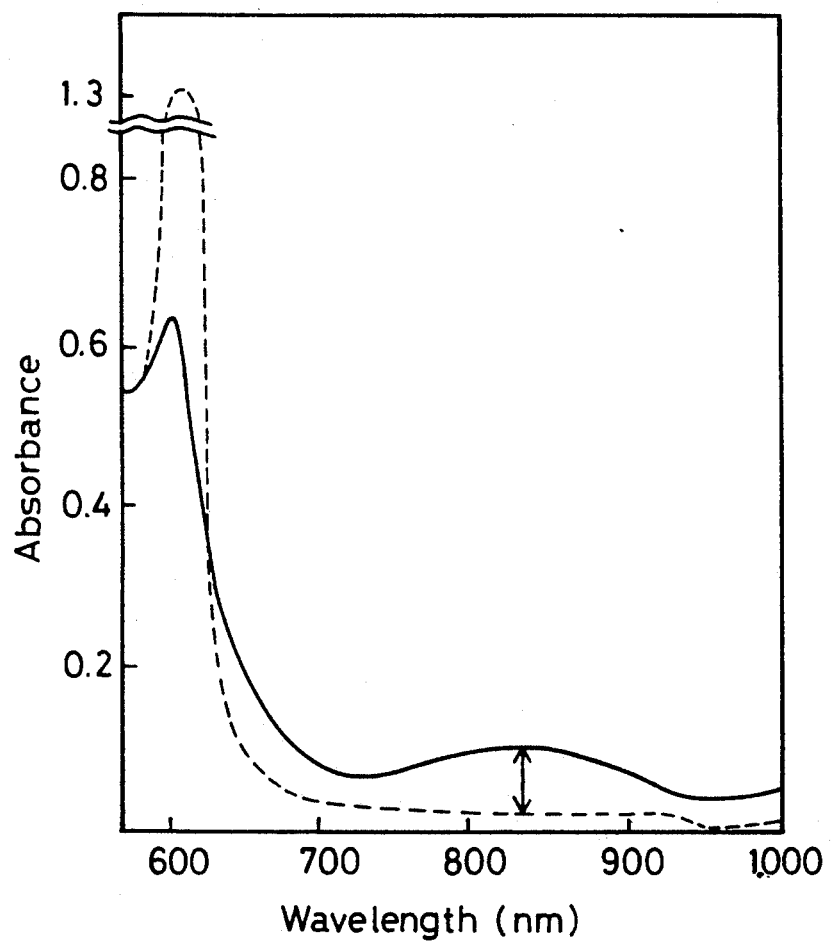
FIG. 96 shows the absorbance spectrum of purified cytochrome oxidase.

FIG. 96 shows the absorbance spectrum of purified cytochrome oxidase. In the figure, the solid line represents oxygenated cytochrome, while the chain line represents reduced cytochrome.

The change in the light absorption of cytochrome indicates whether oxygen is sufficiently present in the cells at a particular time or short in supply. Cytochrome is present all biological tissues including human beings. Actually, intracellular microgranules, known as mitochondria, which contain cytochrome, are present in all living organisms. Accordingly, if the change in absorption of cytochrome, mainly in the visible region, is measured optically by use of the highly directional optical system of the present invention, whether oxygen is sufficiently present in a particular tissue (cells) or short in supply can be known in an on-destructive manner and the spectrum can be recorded with ease.

Figure 97:
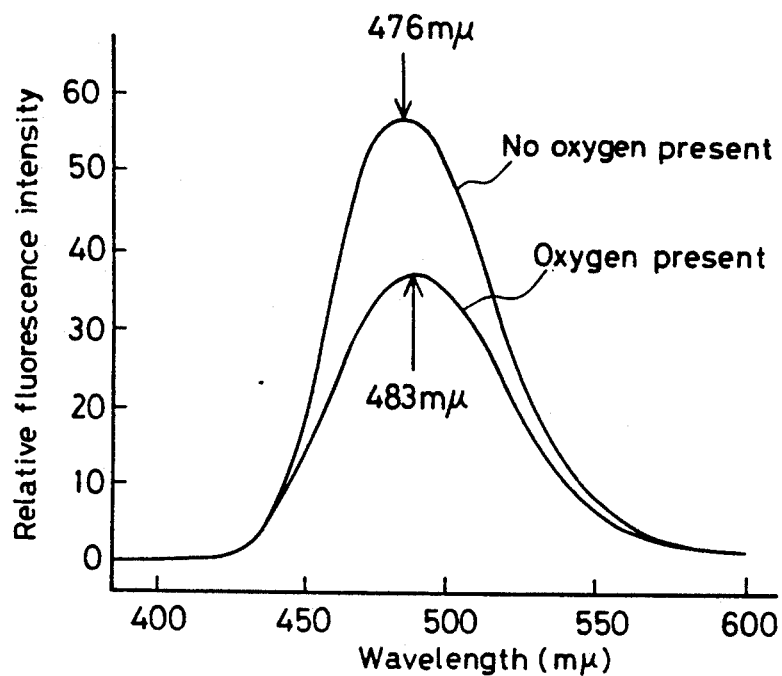
FIG. 97 shows the spectrum of the relative fluorescence intensity of pyridine nucleotide (NADH)

FIG. 97 shows the spectrum of the relative fluorescence intensity of pyridine nucleotide (NADH).

When exposed to ultraviolet rays, our body (tissue) emits relatively strong light (fluorescence) in the visible region. The fluorescence intensity also reflects sensitively the oxygen concentration in the cells.

FIG. 97 shows spectra of fluorescence caused when the heart of a live mouse was illuminated with ultraviolet rays, i.e., light of 340 nm in this case. Fluorescence at 450 to 480 nm is caused by the reduced low-molecular compound pyridine nucleotide contained in biological tissues. The pyridine nucleotide is also present in all the tissues. As the amount of oxygen in a tissue becomes short, the fluorescence intensity increases. Accordingly, by measuring a change in the fluorescence intensity of this substance by use of the highly directional optical system of the present invention, variations in the oxygen concentration can be estimated.

Figure 98:
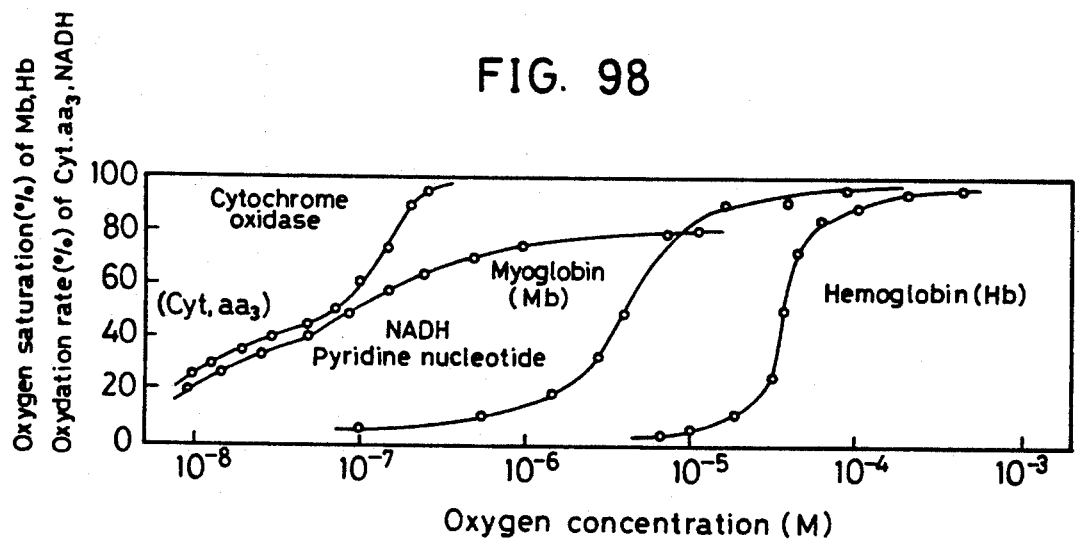
FIG. 98 shows the dependence of indicator substances on the oxygen concentration.

FIG. 98 shows the oxygen concentration dependence of the above-described indicator substances, that is, calibration curves.

As for hemoglobin and myoglobin, a state where these substances are totally combined with oxygen is defined as 100%, while a state where they are combined with no oxygen is defined as 0%, so that each curve expresses in % how much hemoglobin or myoglobin is combined with oxygen. As for cytochrome oxidase and NADH, the ratio of oxidation to reduction is graduated along the axis of ordinates. If it is possible to detect optically how much indicator substance, for example, myoglobin, is combined with oxygen from the calibration curve, it is possible to known the absolute value of the oxygen concentration in the tissue at that time. Similarly, if a change in the quantity of light absorbed by hemoglobin is detected by externally applying light to the human head, it is possible to know the oxygen concentration in the cerebral tissue without the need to open a bore in the skull.

Assuming that myoglobin is 100% oxygenated in the initial state and that a state where the oxygen supply is 0 and the light absorption change is constant is defined as a state where the whole myoglobin has been deoxygenated, changes in the absorption are determined on a full scale. By so doing, the rate of deoxygenation of myoglobin can be obtained at any point on the scale and it can be converted into an oxygen concentration on the basis of the calibration curve.

As has been described above, according to the present invention, a 0-order spectrum of a Fraunhofer diffraction image is taken, with the higher-order components cut off, thereby attenuating scattering components and detecting only information light, and thus enabling an optical CT image to be obtained with high resolution. In application to a human body, for example, an image of a human blood vessel alone can be observed by employing a wavelength corresponding to the absorption region of hemoglobin, for example. If light of a wavelength corresponding to the absorption wavelength of the nervous system, an image of the nervous system can be observed. If it is desired to observe an object having a predetermined absorption wavelength, for example, brain cells, bones, specific cells, etc., only the region that is desired to view can be clearly imaged and observed by illuminating the object with light of the particular absorption wavelength. Accordingly, the present invention is useful for great improvement in medical technology and so forth.

What we claim is:

1. A highly directional optical system comprising a light-receiving element having an interference means for dividing a light propagation region into a plurality of subregions so that a space region where an interference occurs between discrete points at the exit end of said light-receiving element is limited within a minimum spatial resolution unit by means for isolating substantially an 0-order diffraction pattern in a Fraunhofer diffraction image the exit end of said light-receiving unit, thereby enabling detection of information light that is wrapped obscurely in scattered light.

2. A highly directional optical system comprising a light-receiving element having an interference means for dividing a light propagation region into a plurality of subregions so that a space region where an interference pattern occurs between discrete points at the exit end of the light-receiving element is limited by a means for isolating a predetermined minimum spatial resolution unit as a function of a diffraction pattern of a Fraunhofer diffraction image at the exit end of the light-receiving element, whereby information light that is wrapped obscurely in scattered light may be detected.

3. A highly directional optical system according to claim 1 or 2, wherein said light-receiving element comprises a thin tube having a pinhole at each of the entrance and exit ends thereof.

4. A highly directional optical system according to claim 1 or 2, wherein said light-receiving element comprises a hollow thin tube having its wall surface coated with a light absorbing material.

5. A highly directional optical system according to claim 1 or 2, wherein said light-receiving element comprises an optical fiber in which the refractive index of the core portion is smaller than that of the cladding portion.

6. A highly directional optical system according to claim 1 or 2, wherein said light-receiving element has a long focus lens which has front and back focal points at the entrance and exit ends, respectively.

7. A highly directional optical system according to claim 1 or 2, wherein said light-receiving element has an objective lens whose front focal point is positioned at a specimen and an eyepiece whose front focal point is positioned at the back focal point of said objective lens.

8. A highly directional optical system comprising a convex lens and a pinhole which is disposed on a focal plane of said convex lens, said pinhole having a diameter which is not greater than the first dark ring of a Fraunhofer diffraction image produced by said convex lens, thereby taking out only a plane wave component that enters said convex lens from a predetermined direction.

9. A highly directional optical system according to claim 8, wherein a second convex lens, which is substantially the same as said convex lens, is disposed at the exit side of said pinhole such that the front focal plane of said second convex lens is coincident with the plane of said pinhole, whereby a light component passing through said pinhole is taken out after being converted into a plane wave.

10. A highly directional optical system comprising a bundle of highly directional optical systems as defined in claim 8 or 9, which are defined as unit optical elements.

11. A highly directional optical system comprising a convex lens and an optical fiber which is disposed on a focal plane of said convex lens, said optical fiber having a core with a diameter which is not greater than the first dark ring of a Fraunhofer diffraction image produced by said convex lens, thereby taking out only a plane wave component that enters said convex lens from a predetermined direction.

12. A highly directional optical system according to claim 11, wherein a second convex lens, which is substantially the same as said convex lens, is disposed at the exit side of said optical fiber such that the front focal plane of said second convex lens is coincident with the exit end face of said optical fiber, whereby a light component passing through said optical fiber is taken out after being converted into a plane wave.

13. A highly directional optical system comprising a bundle of highly directional optical systems as defined in claim 11 or 12, which are defined as unit optical elements.

14. A highly directional optical system according to any of claim 8 or 11, wherein said convex lens comprises an objective lens.

15. A highly directional optical system according to any of claim 8 or 11, wherein said convex lens comprises a graded-index lens.

16. A highly directional optical system according to claim 8 or 11, wherein said convex lens comprises a plate microlens.

17. A highly directional optical system comprising: a multiple beam highly directional optical system which comprises a bundle of highly directional optical elements each comprising a convex lens and a pinhole which is disposed on a focal plane of said convex lens, said pinhole having a diameter which is not greater than the first dark ring of a Fraunhofer diffraction image produced by said convex lens, thereby taking out only a plane wave component that enters said convex lens from a predetermined direction; and a one- or two-dimensional photodetector which is disposed at the exit side of said multiple beam highly directional optical system, thereby detecting only a plane wave with a one- or two-dimensional intensity distribution which enters from a predetermined direction.

18. A highly directional optical system according to claim 17, wherein each of said highly directional optical elements has a second convex lens, which is substantially the same as said convex lens, said second convex lens being disposed at the exit side of said pinhole such that the front focal plane of said second convex lens is coincident with the plane of said pinhole, whereby a light component passing through said pinhole is taken out after being converted into a plane wave.

19. A highly directional optical system comprising: a multiple beam highly directional optical system which comprises a bundle of highly directional optical elements each comprising a convex lens and an optical fiber which is disposed on a focal plane of said convex lens, said optical fiber having a core with a diameter which is not greater than the first dark ring of a Fraunhofer diffraction image produced by said convex lens, thereby taking out only a plane wave component that enters said convex lens from a predetermined direction; and a one- or two-dimensional photodetector which is disposed at the exit side of said multiple beam highly directional optical system, thereby detecting only a plane wave with a one- or two-dimensional intensity distribution which enters from a predetermined direction.

20. A highly directional optical system according to claim 19, wherein each of said highly directional optical elements has a second convex lens, which is substantially the same as said convex lens, said second convex lens being disposed at the exit side of said optical fiber such that the front focal plane of said second convex lens is coincident with the exit end face of said optical fiber, whereby a light component passing through said optical fiber is taken out after being converted into a plane wave.

21. A highly directional optical system comprising a one- or two-dimensional convex lens array and a one- or two-dimensional photodetector which is disposed on a focal plane of said lens array, said photodetector being arranged to sample and separatively read out only a zero-order diffraction pattern of a Fraunhofer diffraction image produced by each convex lens, thereby detecting only a plane wave with a one- or two-dimensional intensity distribution which enters from a predetermined direction.

22. A highly directional optical system according to any of claims 17 to 21, wherein said convex lens comprises an objective lens.

23. A highly directional optical system according to any of claims 17 to 21, wherein said convex lens comprises a graded-index lens.

24. A highly directional optical system according to any of claims 17 to 21, wherein said convex lens comprises a plate microlens.

25. An optical sectional image forming apparatus comprising: a laser light source for illuminating an object of measurement with laser light directly or through a lens system; a high resolution light-receiving system comprising a plurality of light-receiving elements each receiving the transmitted light from said object illuminated with the laser light and dividing a light propagation region into a plurality of subregions so that a space region where an interference occurs between discrete points at the exit end is limited within a minimum spatial resolution unit; photoelectric detecting means for detecting emergent light rays from said high resolution light-receiving system and converting them into electrical signals; and means for arithmetically processing the detected signals from said photoelectric detecting means, thereby determining a light absorption distribution of said object, and thus obtaining an optical sectional image.

26. An optical sectional image forming apparatus comprising: a laser light source for illuminating an object of measurement with laser light directly or through a lens system; a high resolution light-receiving system comprising a plurality of light-receiving elements each receiving the transmitted light from said object through a chopper and dividing a light propagation region into a plurality of subregions so that a space region where an interference occurs between discrete points at the exit end is limited within a minimum spatial resolution unit; photoelectric detecting means for detecting emergent light rays from said high resolution light-receiving system and converting them into electrical signals; means for synchronously detecting the detected signals from said photoelectric detecting means; means for determining the sum of and difference between a detected signal component obtained by said synchronous detection and a dark signal component; and means for arithmetically processing the result of said addition and subtraction, thereby determining a light absorption distribution of said object while removing the background component, and thus obtaining an optical sectional image.

27. An optical sectional image forming apparatus comprising: means for alternately illuminating an object of measurement with laser light of different wavelengths; a high resolution light-receiving system comprising a plurality of light-receiving elements each receiving the transmitted light from said object through a sector and dividing a light propagation region into a plurality of subregions so that a space region where an interference occurs between discrete points at the exit end is limited within a minimum spatial resolution unit; photoelectric detecting means for detecting emergent light rays from said high resolution light-receiving system and converting them into electrical signals; means for synchronously detecting the detected signals from said photoelectric detecting means; means for arithmetically processing the signals corresponding to each wavelength obtained by said synchronous detection, thereby determining a light absorption distribution of said object, and thus obtaining an optical sectional image.

28. An optical sectional image forming apparatus according to claim 27, which employs a sector capable of obtaining optical signals of two wavelengths and a dark signal to determine the sum of and difference between the detected signal for each wavelength and the dark signal, thereby removing the background component.

* * * * *